(12) United States Patent
Baba et al.

(10) Patent No.: US 12,004,872 B2
(45) Date of Patent: Jun. 11, 2024

(54) BIOLOGICAL INFORMATION MONITORING SYSTEM

(71) Applicant: Agama-X Co., Ltd., Tokyo (JP)

(72) Inventors: Motofumi Baba, Kanagawa (JP);
Masahiro Sato, Kanagawa (JP);
Kiichiro Arikawa, Kanagawa (JP);
Tadashi Suto, Kanagawa (JP); Kengo Tokuchi, Kanagawa (JP)

(73) Assignee: Agama-X Co., Ltd., Tokyo (JP)

( * ) Notice: Subject to any disclaimer, the term of this patent is extended or adjusted under 35 U.S.C. 154(b) by 711 days.

(21) Appl. No.: 17/131,761

(22) Filed: Dec. 23, 2020

(65) Prior Publication Data
US 2022/0104769 A1 Apr. 7, 2022

(30) Foreign Application Priority Data
Oct. 1, 2020 (JP) ................. 2020-166699

(51) Int. Cl.
*A61B 5/00* (2006.01)
*A61B 5/369* (2021.01)
*A61B 5/38* (2021.01)
*H02J 7/02* (2016.01)
*H04R 1/10* (2006.01)

(52) U.S. Cl.
CPC .............. *A61B 5/6803* (2013.01); *H02J 7/02* (2013.01); *H04R 1/1016* (2013.01); *H04R 1/1025* (2013.01); *A61B 2560/0214* (2013.01)

(58) Field of Classification Search
CPC ... A61B 2560/0214; A61B 5/369; A61B 5/38; A61B 5/6803; A61B 5/6815; H02J 7/02; H04R 1/1016; H04R 1/1025
See application file for complete search history.

(56) References Cited

U.S. PATENT DOCUMENTS

| 2018/0271428 A1* | 9/2018 | Takagi | ................. | A61B 5/6817 |
| 2022/0139366 A1* | 5/2022 | Asada | .................... | H04R 1/105 381/71.6 |

FOREIGN PATENT DOCUMENTS

| JP | 2008111111 | 5/2008 |
| JP | 2011217986 | 11/2011 |

OTHER PUBLICATIONS

European Search Report and the European Search Opinion dated May 27, 2021 From the European Patent Office Re. Application No. 20216394.5.

\* cited by examiner

*Primary Examiner* — Jonathan T Kuo
*Assistant Examiner* — Vynn V Huh

(57) ABSTRACT

A biological information monitoring system includes: a biological information monitoring apparatus that monitors biological information of an organism wearing the biological information monitoring apparatus on an ear; and a charger that charges the biological information monitoring apparatus in a non-contact manner. The charger charges the biological information monitoring apparatus when the biological information monitoring apparatus is not monitoring biological information.

9 Claims, 44 Drawing Sheets

BIOLOGICAL INFORMATION MONITORING SYSTEM

CROSS-REFERENCE TO RELATED APPLICATIONS

This application is based on and claims priority under 35 USC 119 from Japanese Patent Application No. 2020-166699 filed Oct. 1, 2020.

BACKGROUND

(i) Technical Field

The present disclosure relates to a biological information monitoring system.

(ii) Related Art

A technology for monitoring biological information, such as brain waves, is known.

Japanese Unexamined Patent Application Publication No. 2011-217986 discloses a technology for monitoring brain waves with a canal-type earphone including a conductive member.

SUMMARY

Aspects of non-limiting embodiments of the present disclosure relate to making it possible to charge a biological information monitoring apparatus while reducing the influence on biological information to be monitored.

Aspects of certain non-limiting embodiments of the present disclosure overcome the above disadvantages and/or other disadvantages not described above. However, aspects of the non-limiting embodiments are not required to overcome the disadvantages described above, and aspects of the non-limiting embodiments of the present disclosure may not overcome any of the disadvantages described above.

According to an aspect of the present disclosure, there is provided a biological information monitoring system including: a biological information monitoring apparatus that monitors biological information of an organism wearing the biological information monitoring apparatus on an ear; and a charger that charges the biological information monitoring apparatus in a non-contact manner. The charger charges the biological information monitoring apparatus when the biological information monitoring apparatus is not monitoring biological information.

BRIEF DESCRIPTION OF THE DRAWINGS

An exemplary embodiment of the present disclosure will be described in detail based on the following figures, wherein.

DETAILED DESCRIPTION

Figure 1:
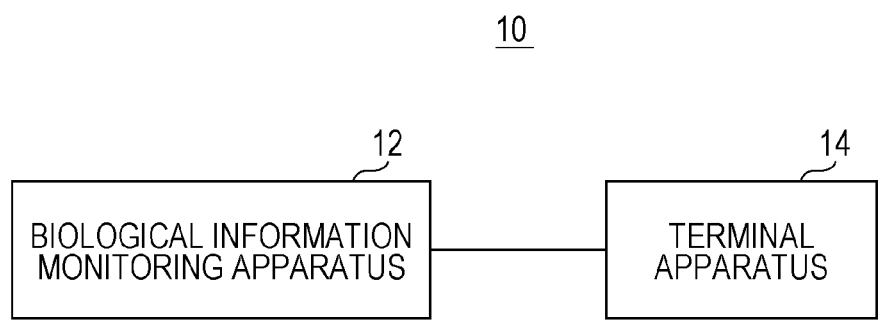
FIG. 1 is a block diagram of a biological information monitoring system according to the exemplary embodiment.

A biological information monitoring system 10 according to an exemplary embodiment will be described below with reference to FIG. 1. FIG. 1 illustrates an example of the configuration of the biological information monitoring system 10. The biological information monitoring system 10 includes a biological information monitoring apparatus 12 and a terminal apparatus 14.

The biological information monitoring apparatus 12 and the terminal apparatus 14 each have a function of communicating with another apparatus via a communication channel by using a wired medium, such as a cable, or a wireless medium. That is, the biological information monitoring apparatus 12 and the terminal apparatus 14 may be physically connected to another apparatus via a cable and send and receive information with this apparatus, or may send and receive information with another apparatus by wireless communication. Examples of wireless communication are short-range wireless communication, Wi-Fi (registered trademark), infrared communication, and visible light communication. Another wireless communication standard may be employed. Examples of short-range wireless communication are Bluetooth (registered trademark), radio frequency identifier (RFID), and near field communication (NFC). The biological information monitoring apparatus 12 and the terminal apparatus 14 may alternatively communicate with another apparatus, such as a server, via a communication channel, such as a local area network (LAN) or the Internet.

The biological information monitoring apparatus 12 monitors biological information concerning organisms, such as humans, animals other than humans, and plants.

Biological information include various types of information generated from organisms. The concept of biological information covers information concerning brain activities (such as brain waves, brain blood flow, and brain magnetic field signal), pulse rate, myoelectric information, such as myoelectric waveforms, saliva (such as the amount of saliva), pulse waves, blood pressure, blood flow, pulse, heart rate, electrocardiogram waveforms, eye movement, body temperature, amount of perspiration, gaze, voice, motion of an organism, and body fluids, such as blood. Information obtained by a biomarker may be used as biological information. Biological information may be information indicating potentials generated from an organism. For example, biological information may be brain waves, such as electroencephalograms (EEG), obtained by measuring minute electric currents generated by the brain activities, electrocardiograms created by measuring minute electric currents generated by the heart pulsating beats, electromyograms created by measuring minute electric currents generated by the muscle activities, and skin potentials obtained by measuring minute electric currents generated in the skin. The above-described items of information are only examples of biological information, and other items of biological information may be used. The biological information monitoring apparatus 12 monitors one or multiple types of biological information.

As a result of analyzing biological information, mental, emotional, or psychological information may be obtained. For example, as a result of analyzing biological information about a certain person, information indicating the mental state, the emotional state, or the psychological state of this person may be obtained. Biological information concerning an animal other than a human or a plant may be analyzed to obtain information indicating the state of the animal or the plant.

The biological information monitoring apparatus 12 may be a wearable device which can be worn by an organism and monitors biological information of the organism. The biological information monitoring apparatus 12 may be a device which monitors biological information of the organism without being worn by the organism.

Examples of a wearable device are a bearable device worn on an ear of an animal, a device worn on the head of an animal, a device worn around the wrist, arm, or finger of an animal (for example, a watch-type device, such as a smart watch), a device worn around the neck of an animal, a device worn on the torso of an animal (the abdomen or chest, for example), a device worn on the lower limb (the thigh, lower leg, knee, foot, or ankle of a human, for example), a pair-of-glasses-type device, and a contact-lens-type device. The biological information monitoring apparatus 12 may be a wearable device worn by a part of the body other than the above-described parts. The biological information monitoring apparatus 12 may be worn by multiple parts of the body.

A bearable device may be an earphone, a hearing aid, an earring-type device, a clip-type device, or a device with a band or a cable wound around the ear. A device worn on the head may be a headset with a band or a cable wound around the head. A device worn around the wrist, arm, or finger may be a device with a band or a cable wound around the wrist, arm, or finger. A device worn by another part of the body may have a band or a cable.

The biological information monitoring apparatus 12 may be a contact-type device that is brought into contact with an organism to monitor biological information of the organism or a non-contact-type device that is not brought into contact with an organism to monitor biological information of the organism. The biological information monitoring apparatus 12 may have both the functions as a contact-type device and a non-contact-type device. That is, the biological information monitoring apparatus 12 may monitor biological information in contact with an organism and also monitor biological information without contacting an organism. Biological information monitored by the contact-type device and that by the non-contact-type device may be the same type of biological information or different types of biological information.

The biological information monitoring apparatus 12 includes an electrode and a sensor for monitoring biological information. The electrode may detect potentials, which are an example of biological information, in contact with or without contacting an organism. The sensor may monitor biological information in contact with or without contacting an organism. For example, the electrode may be brought into contact with an animal to detect potentials representing brain waves of the animal. The sensor may monitor biological information indicating the body temperature of an animal without contacting it. These are only example of biological information, and other biological information may be monitored.

For example, the biological information monitoring apparatus 12 includes one or multiple electrodes. Multiple electrodes may be applied to an organism so as to detect potentials of the organism. The detected potentials include bioelectric potentials, which are an example of biological information of this organism. As a result of processing the detected potentials, the bioelectric potentials can be extracted from the detected potentials. For example, the detected potentials may include noise which does not originate from the bioelectric potentials of an organism, and as a result of executing processing, such as noise cancelling, the bioelectric potentials free from noise can be obtained. Potentials that can be identified as noise are potentials generated by the motion of an organism, potentials transmitted from the outside of an organism, potentials generated due to global environments, potentials representing biological information other than biological information to be monitored. Potentials generated from devices, such as a personal computer (PC) and a smartphone, may be an example of noise. Among the multiple electrodes, the electrode for detecting potentials may be switched in accordance with the detection sensitivity or the monitoring situation, such as the occurrence of noise. If various types of bioelectric potentials are detected together, they may be separated into individual types of potentials from each other according to the frequency. Alternatively, on the monitoring time axis, mixed different types of bioelectric potentials are divided into portions strongly related to each other and portions only sparsely related to each other, thereby separating the mixed bioelectric potentials into individual types of potentials. For example, in the above-described bearable device, information indicating the brain activities, information indicating the pulse rate, myoelectric information originating from the motion of muscles, and information originating from the blood flow, such as the pulse and the heart rate, may be monitored in a mixed manner. For these different types of information, the frequency or the absolute value of the output level is usually different. As a result of conducting the frequency analysis on a monitoring signal or based on the difference in the level of the output value of the monitoring signal, these types of information can be separated from each other. For example, brain waves can be separated into α waves, β waves, θ waves, δ waves, and γ waves according to the frequency. A different approach may be taken. For example, biological information is monitored in a hearable device under certain conditions. Then, under the same conditions, commercially available measuring devices, each of which is specially used for a specific type of biological information, such as an electroencephalograph, an electromyograph, and a blood flow measuring device, are used to monitor the corresponding types of biological information multiple times. Then, a monitoring signal representing multiple types of biological information obtained by the hearable device is analyzed by using a frequency analysis technique, such as Fourier transform or wavelet transform, and then, statistical processing is also executed on the analysis result and monitoring signals obtained by the individual measuring devices. As a result, the monitoring signal can be separated into individual types of biological information.

In one example, one or plural electrodes are used as electrodes for detecting potentials including bioelectric potentials (such an electrode will be called a sensor electrode). Another one or plural electrodes are used as electrodes for grounding (such an electrode will be called a ground electrode). Another one or plural electrodes are used as electrodes for detecting potentials to be compared with potentials detected by the sensor electrodes (such an electrode will be called a reference electrode).

Hereinafter, potentials detected by the sensor electrodes will be called sensor potentials, potentials detected by the reference electrodes will be called reference potentials, and potentials detected by the ground electrodes will be called ground potentials.

In another example, the biological information monitoring apparatus 12 includes one or multiple sensors. For example, multiple sensors are applied to an organism so as to monitor biological information of the organism. The monitored biological information may contain noise. Among the multiple sensors, the sensor to be used for monitoring biological information may be switched in accordance with the detection sensitivity or the monitoring situation, such as the occurrence of noise.

In another example, the biological information monitoring apparatus 12 may include one or multiple electrodes and one or multiple sensors.

Plural biological information monitoring apparatuses 12, each of which includes at least one of at least one electrode and at least one sensor, may be used, and may monitor the same type or different types of biological information.

The biological information monitoring apparatus 12 may send biological information, such as a potential signal indicating potentials detected by the electrode, information monitored by the sensor, and analysis information, to the terminal apparatus 14. The biological information monitoring apparatus 12 may send biological information to a device, such as a server, other than the terminal apparatus 14. In addition to or instead of sending biological information to another device, the biological information monitoring apparatus 12 may store the biological information therein.

The terminal apparatus 14 is a PC, a mobile terminal (such as a smartphone, a tablet PC, or a cellular phone), or another device, such as a music player. The terminal apparatus 14 may receive biological information from the biological information monitoring apparatus 12 and store, analyze, or send the received biological information to another device. For example, the terminal apparatus 14 may extract biological information from the potentials detected from an organism.

In one example, the biological information monitoring apparatus 12 is a hearable device, which is used by being inserted into the ear canal of a human. The biological information monitoring apparatus 12 may be a device including a canal-type earphone. As a function of the earphone, the biological information monitoring apparatus 12 converts an electric signal output from a playback device into sound waves by using a speaker. The playback device may be the terminal apparatus 14. For example, the biological information monitoring apparatus 12 receives a sound signal, such as an audio signal, from the terminal apparatus 14 by wired or wireless communication and generates sound in accordance with the sound signal.

The configuration of the biological information monitoring apparatus 12 will be described below in detail with reference to FIGS. 2 through 10. The biological information monitoring apparatus 12 will be discussed through illustration of earphones worn on the ears of a human. However, it may be a hearable device other than earphones.

Figure 2:
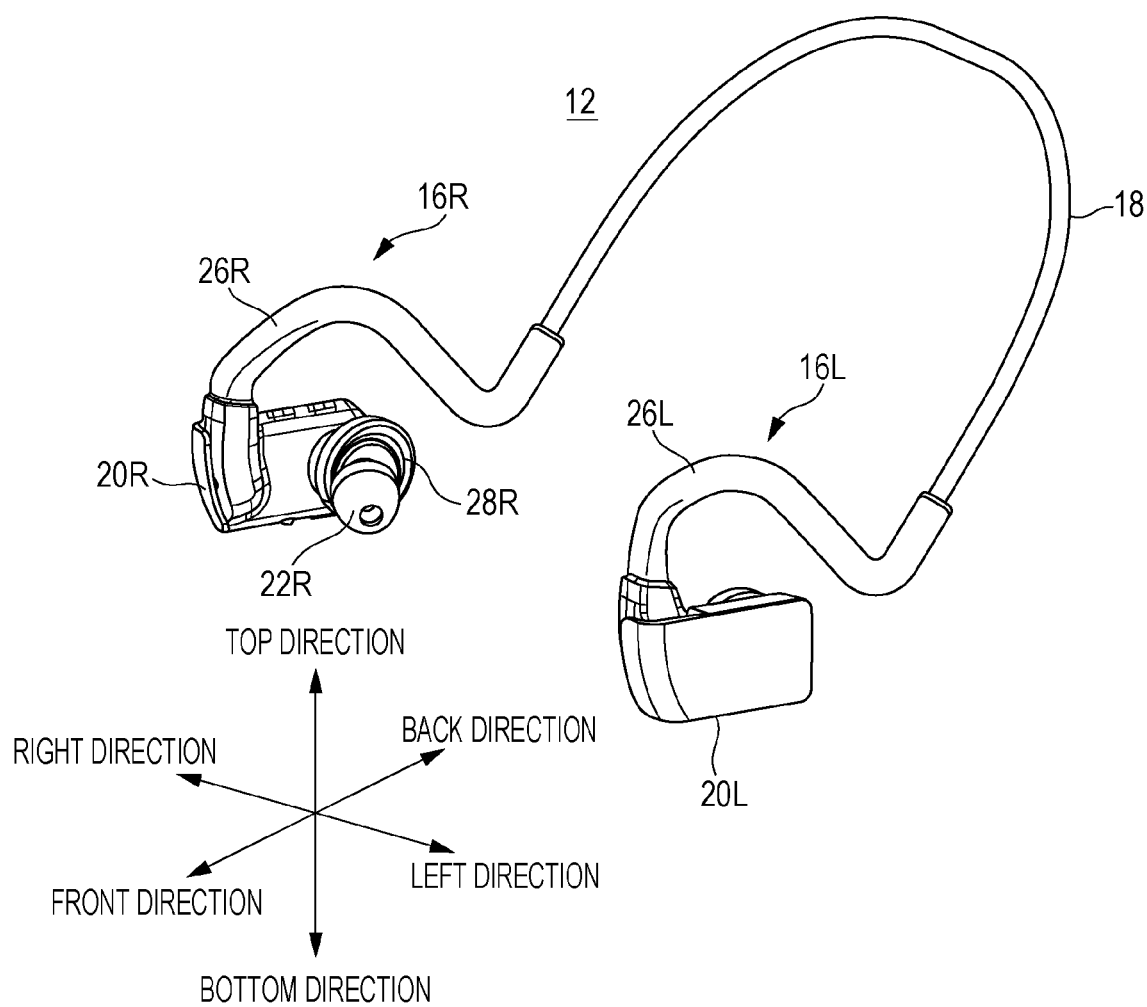
FIG. 2 is a perspective view illustrating the overall configuration of a biological information monitoring apparatus.
Figure 3:
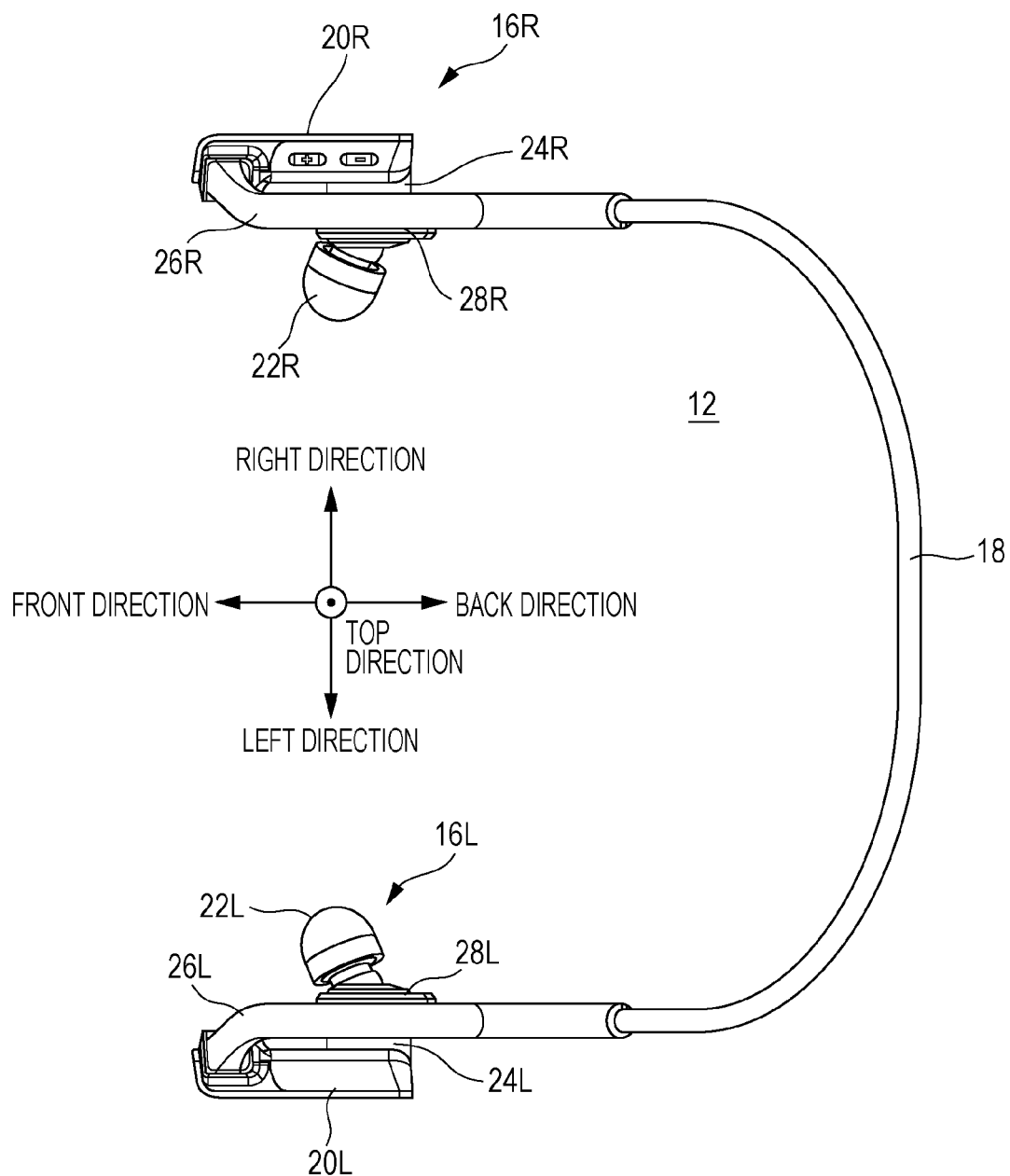
FIG. 3 illustrates the biological information monitoring apparatus as viewed from above.
Figure 4:
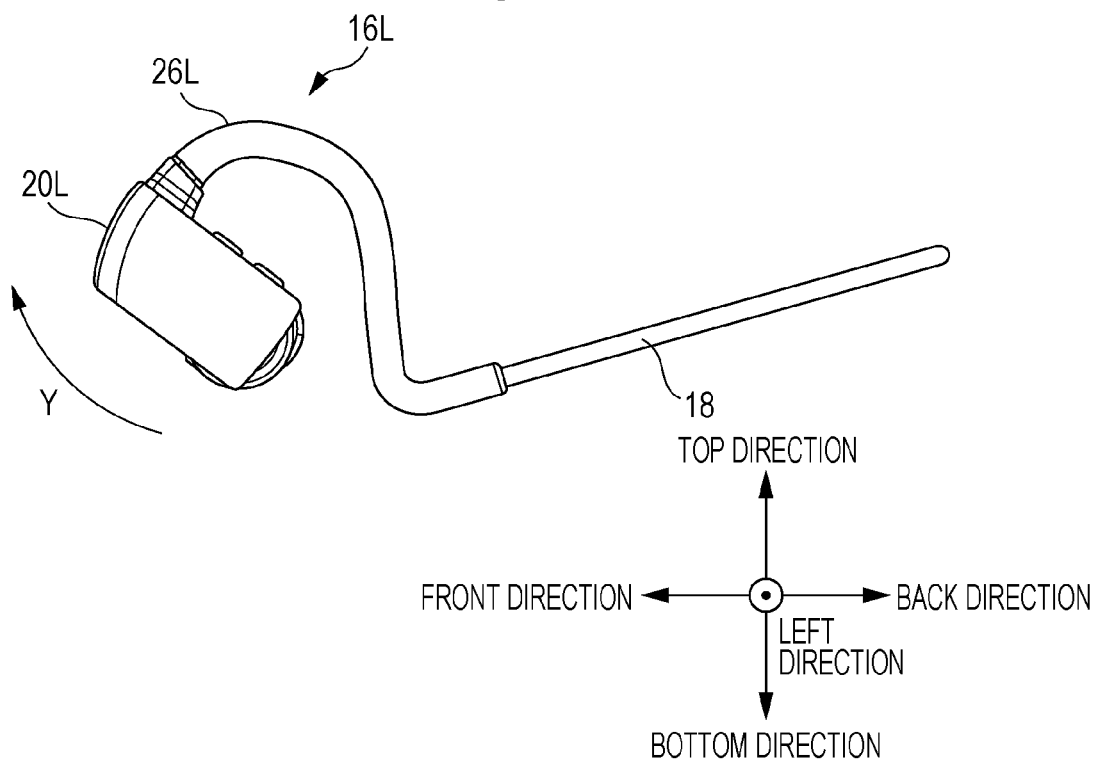
FIG. 4 illustrates a left-side earphone as viewed from the left side.
Figure 5:
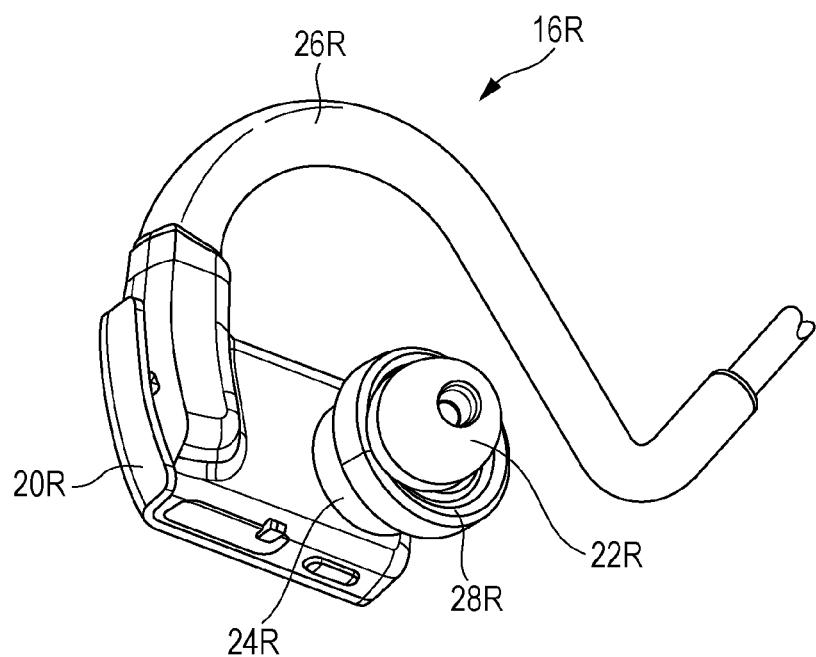
FIG. 5 is a perspective view of a right-side earphone.
Figure 6:
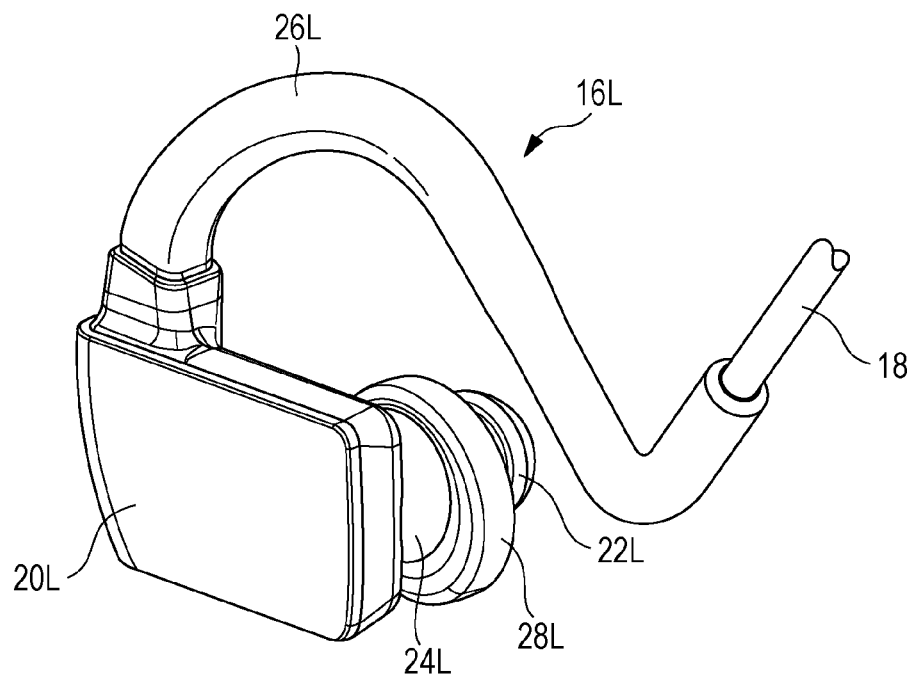
FIG. 6 is a perspective view of the left-side earphone.
Figure 7:
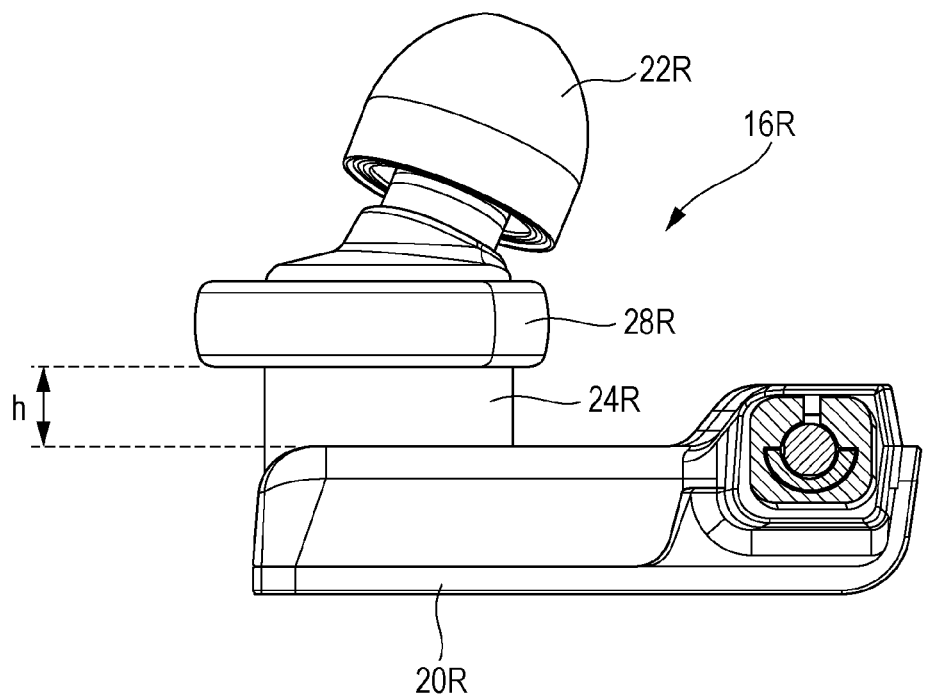
FIG. 7 illustrates the right-side earphone as viewed from above.
Figure 8:
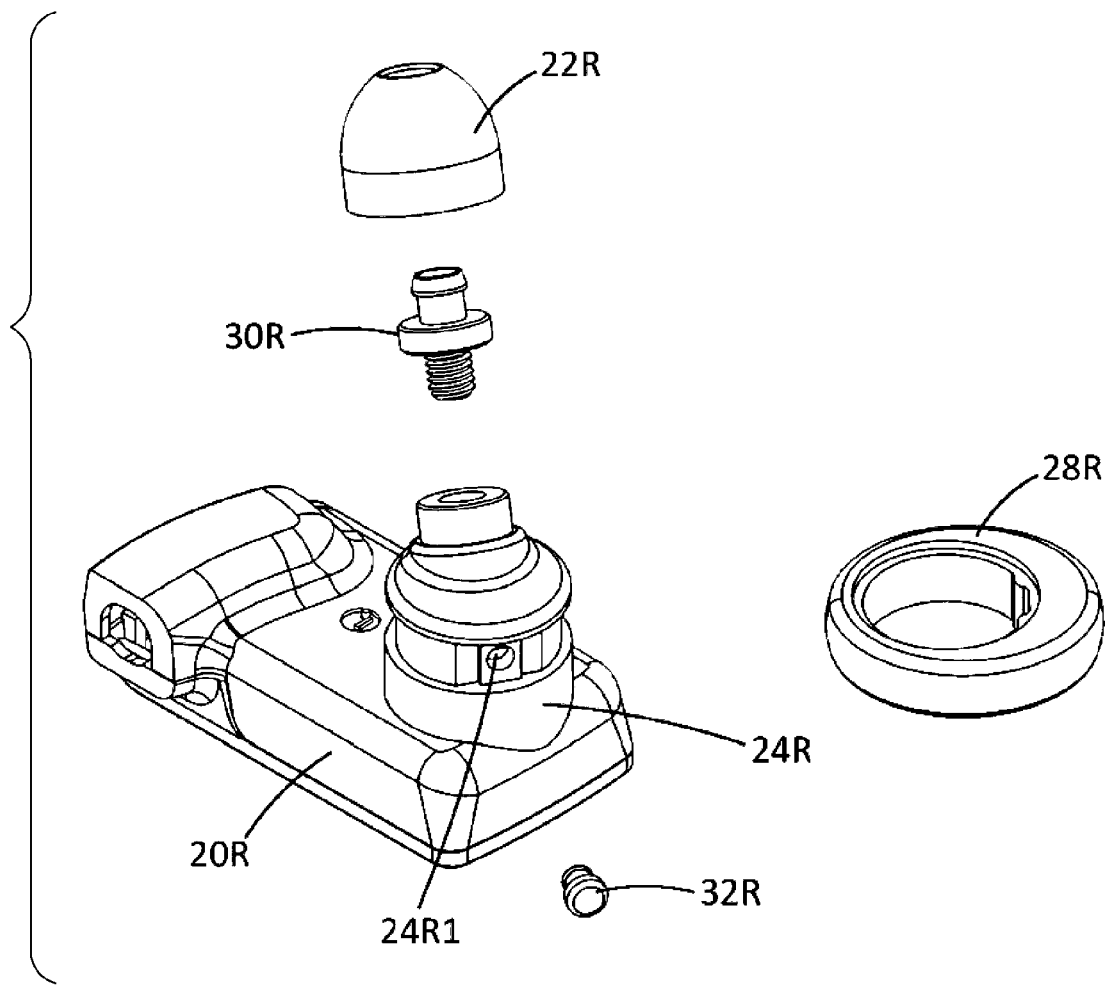
FIG. 8 is an exploded perspective view of the right-side earphone.
Figure 9:
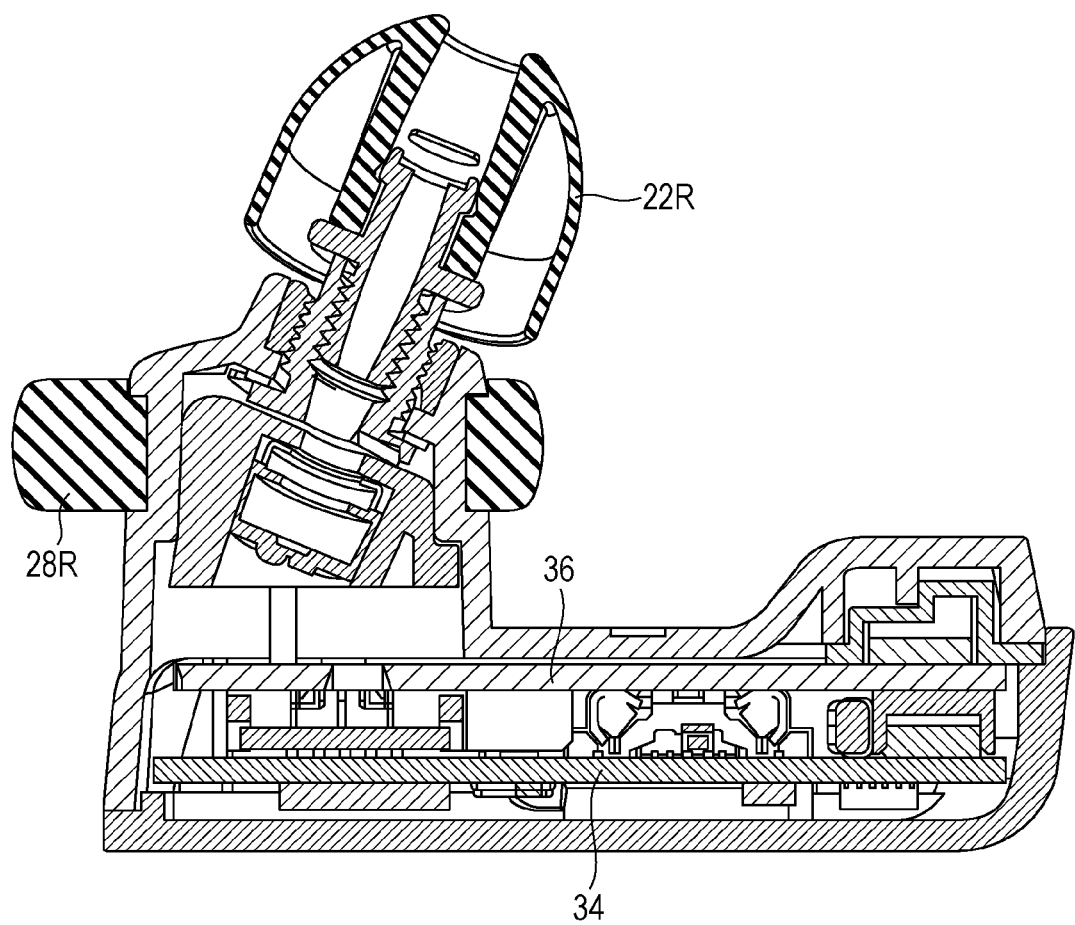
FIG. 9 is a sectional view of the right-side earphone.
Figure 10:
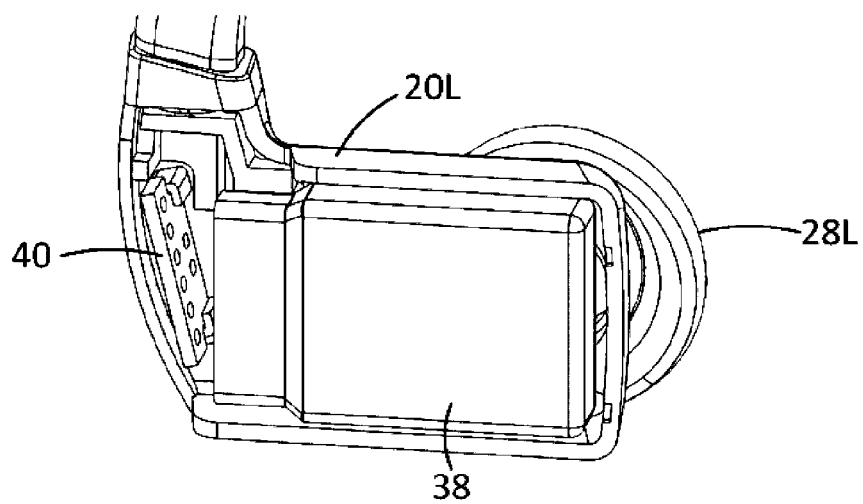
FIG. 10 is a perspective view illustrating the inside of the left-side earphone.

FIG. 2 is a perspective view illustrating the overall configuration of the biological information monitoring apparatus 12. FIG. 3 illustrates the biological information monitoring apparatus 12 as viewed from above. FIG. 4 illustrates a left-side earphone as viewed from the left side. FIG. 5 is a perspective view of a right-side earphone. FIG. 6 is a perspective view of the left-side earphone. FIG. 7 illustrates the right-side earphone as viewed from above. FIG. 8 is an exploded perspective view of the right-side earphone. FIG. 9 is a sectional view of the right-side earphone. FIG. 10 is a perspective view illustrating the inside of the left-side earphone.

For the sake of description, the front and back directions, left and right directions, and top and bottom directions are defined, as shown in FIG. 2. The front direction is a direction in which a user faces in front. The back direction is a direction opposite the front direction. The top direction is a direction in which the top of the head of a user faces. The bottom direction is a direction opposite the top direction. The right direction is a direction on the side of the right hand of a user, while the left direction is a direction on the side of the left hand of a user. The front-back direction, the top-bottom direction, and the left-right direction are perpendicular to each other.

In one example, the biological information monitoring apparatus 12 monitors biological information including information indicating brain waves. The biological information monitoring apparatus 12 may monitor another type of biological information in addition to brain waves. For example, when a right-side earphone 16R and a left-side earphone 16L, which will be explained later, are worn on the ears of a user, potentials representing biological information are detected. A potential signal indicating the detected potentials typically represents brain waves, but may also represent potentials generated from the motion of the head, such as the motion of the face due to facial expressions, and the motion of the neck, jaws, and eyeballs. Additionally, biological information generated by a change in the blood flow caused by the motion of the head, such as the pulse waves related to the brain blood flow and the heart rate related to the cardiac blood vessels, may distinctively be monitored. In this manner, the biological information monitoring apparatus 12 may monitor other types of biological information, together with brain waves. Biological information other than brain waves may be handled as noise (eliminated, for example), or be separated from the brain waves and be used for certain processing, as described above.

As shown in FIGS. 2 and 3, the biological information monitoring apparatus 12 is largely constituted by a right-side earphone 16R to be worn on the right ear of a user, a left-side earphone 16L to be worn on the left ear of a user, and a cable 18 electrically connecting the right-side earphone 16R and the left-side earphone 16L with each other. The right-side earphone 16R and the left-side earphone 16L may send and receive signals and data with each other via the cable 18. A remote controller may be provided in the cable 18 to operate the biological information monitoring apparatus 12.

One or both of the right-side earphone 16R and the left-side earphone 16L function as the biological information monitoring apparatus 12 that monitors biological information.

For example, one of the right-side earphone 16R and the left-side earphone 16L may have a sensor electrode, a reference electrode, and a ground electrode, and the other earphone may have no electrodes.

In another example, each of the right-side earphone 16R and the left-side earphone 16L may have a sensor electrode, a reference electrode, and a ground electrode.

In still another example, one of the right-side earphone 16R and the left-side earphone 16L may have one or two electrodes among a sensor electrode, a reference electrode, and a ground electrode, while the other earphone may have the remaining electrode or electrodes.

In another example, each of the right-side earphone 16R and the left-side earphone 16L may have one or plural electrodes, and such electrodes may be allocated to a sensor electrode, a reference electrode, and a ground electrode.

In another example, each of the right-side earphone 16R and the left-side earphone 16L may have plural sensor electrodes, plural reference electrodes, or plural ground electrodes. For example, the right-side earphone 16R may have plural sensor electrodes, while the left-side earphone 16L may have plural reference electrodes.

The right-side earphone 16R is a canal-type earphone, for example, and includes a right-side housing 20R, a right-side earpiece 22R, a right-side support 24R, a right-side ear hanger 26R, and an electrode member 28R. The earpiece may also be called an earpad.

The right-side housing 20R is a thin rectangular-parallelopiped-shaped housing which stores elements such as an electronic circuit therein. In the right-side housing 20R, the right-side earpiece 22R and the right-side support 24R are located facing the right ear of a user when the user wears the biological information monitoring apparatus 12. Within the right-side housing 20R, a controller, a speaker, a communication unit (communication chip, for example), an electronic circuit for analyzing and processing biological information, and a 6-axis sensor (including a 3-axis sensor for detecting the acceleration and a 3-axis sensor for detecting the angular velocity, for example), a memory, a global positioning system (GPS) sensor, for example, are stored. The communication unit implements a wireless communication function, such as Bluetooth or Bluetooth Low Energy (BLE). The communication unit loads a wireless LAN (such as a Wi-Fi network) and a cellular (3G, 4G, 5G, or low-power wide-area (LPWA)) module to achieve a wider communication area and can thus directly send data to local area devices having a communication range longer than Bluetooth and to remote devices via the Internet. Using the 6-axis sensor makes it possible to detect the moving direction, orientation, and rotation of the right-side housing 20R.

Biological information may be stored in the memory. The electronic circuit for analyzing biological information may not necessarily be provided in the biological information monitoring apparatus 12.

The right-side support 24R has a columnar shape, such as a cylindrical shape, and projects from the side surface of the right-side housing 20R (for example, the side surface which opposes the right ear when the right-side earphone 16R is worn on the right ear of a user). The right-side support 24R is disposed between the right-side housing 20R and the right-side earpiece 22R. The outer diameter of the right-side support 24R is larger than that of the right-side earpiece 22R. The electrode member 28R is provided on the entirety or part of the side surface of the right-side support 24R.

The electrode member 28R has a ring-like shape, for example, and is supported by the columnar right-side support 24R. The entirety or part of the electrode member 28R serves as an electrode. That is, an electrode may be provided on the entire surface or part of the surface of the electrode member 28R. The electrode member 28R is made of conductive carbon rubber, for example. In this case, too, the electrode member 28R may be entirely made of conductive carbon rubber and the entirety (entire surface, for example) of the electrode member 28R may serve as an electrode. Alternatively, the electrode member 28R may be partially made of conductive carbon rubber and part (part of the surface, for example) of the electrode member 28R may serve as an electrode.

The right-side earpiece 22R is provided at the end of the right-side support 24R. More specifically, the right-side earpiece 22R is provided at the end of the right-side support 24R opposite the end contacting the right-side housing 20R. The right-side earpiece 22R has a cylindrical shape tapering down toward the forward end, but may be formed in another shape.

Within the right-side earpiece 22R, a sound transmission tube (such as a conductive tube member 30R, which will be discussed later), for example, is stored. Sound emitted from a speaker is transmitted through the sound transmission tube within the right-side earpiece 22R and is output from the right-side earpiece 22R to the outside. An electrode is provided on the entirety or part of the outer surface (side surface, for example) of the right-side earpiece 22R. The electrode is made of conductive carbon rubber, for example. The right-side earpiece 22R itself may be made of conductive rubber. For example, the entirety or part of the right-side earpiece 22R may be made of conductive rubber. That is, the entirety or part of a surface of the right-side earpiece 22R may serve as an electrode.

The right-side earpiece 22R and the electrode member 28R may be made of an elastic member. As the elastic member, a resin, such as rubber, may be used. More specifically, silicon (Si) rubber (S1734 made by NOK CORPORATION) or urethane rubber may be used for the right-side earpiece 22R and the electrode member 28R. The hardness of the right-side earpiece 22R and that of the electrode member 28R in compliance with the standard of durometer type A (instantaneous) are 40 to 75. For example, a resin having a hardness of 70 may be used for the right-side earpiece 22R and the electrode member 28R.

The right-side earpiece 22R is inserted into and is placed in the canal of the right ear of a user so as to contact the ear canal. The electrode member 28R supported by the right-side support 24R is placed on the right ear so as to contact the cavity of concha. This will be discussed in detail later.

The right-side ear hanger 26R is generally formed in a curved shape. When a user wears the right-side earphone 16R, the right-side ear hanger 26R is hung on the right ear. For example, the right-side ear hanger 26R is hung on the helix of the right ear. More specifically, the right-side ear hanger 26R is placed on the back side of the helix of the right ear so as to contact the helix. One end of the right-side ear hanger 26R is connected to the front side of the right-side housing 20R and is curved toward the back side of the right-side housing 20R. When the user wears the right-side earphone 16R, this curved portion is placed on the back side of the helix of the right ear so as to touch the helix. For example, the curved portion is formed to match the shape of the back side of the helix of the right ear. The other end of the right-side ear hanger 26R is connected to one end of the cable 18.

The right-side earpiece 22R and the right-side support 24R are replaceable. For example, multiple (three to five) types of right-side earpieces 22R and those of right-side supports 24R of different shapes and different sizes are prepared, and a suitable right-side earpiece 22R and a suitable right-side support 24R are selected in accordance with the shape of the right ear (such as the shapes of the ear canal, cavity of concha, and other parts) of a user.

The left-side earphone 16L is a canal-type earphone, for example, and includes a left-side housing 20L, a left-side earpiece 22L, a left-side support 24L, a left-side ear hanger 26L, and an electrode member 28L.

The left-side housing 20L is a thin rectangular-parallelopiped-shaped housing which stores elements such as a battery therein. In the left-side housing 20L, the left-side earpiece 22L and the left-side support 24L are located facing the left ear of a user when the user wears the biological information monitoring apparatus 12. Power from the battery is supplied to the right-side earphone 16R and the left-side earphone 16L so as to drive them. Power from the battery is supplied to a speaker and individual circuits, for example. The battery may be provided in one or both of the right-side housing 20R and the left-side housing 20L.

The left-side support 24L has a columnar shape, such as a cylindrical shape, and projects from the side surface of the left-side housing 20L (for example, the side surface which opposes the left ear when the left-side earphone 16L is worn on the left ear of a user). The left-side support 24L is disposed between the left-side housing 20L and the left-side earpiece 22L. The outer diameter of the left-side support 24L is larger than that of the left-side earpiece 22L. The electrode member 28L is provided on the entirety or part of the side surface of the left-side support 24L.

The electrode member 28L has a ring-like shape, for example, and is supported by the columnar left-side support 24L. The entirety or part of the electrode member 28L serves as an electrode. That is, an electrode may be provided on the entire surface or part of the surface of the electrode member 28L. The electrode member 28L is made of conductive carbon rubber, for example. In this case, too, the electrode member 28L may be entirely made of conductive carbon rubber and the entirety (entire surface, for example) of the electrode member 28L may serve as an electrode. Alternatively, the electrode member 28L may be partially made of conductive carbon rubber and part (part of the surface, for example) of the electrode member 28L may serve as an electrode.

The left-side earpiece 22L is provided at the end of the left-side support 24L. More specifically, the left-side earpiece 22L is provided at the end of the left-side support 24L opposite the end contacting the left-side housing 20L. The left-side earpiece 22L has a cylindrical shape tapering down toward the forward end, but may be formed in another shape.

Within the left-side earpiece 22L, a sound transmission tube, for example, is stored. Sound emitted from the speaker is transmitted through the sound transmission tube within the left-side earpiece 22L and is output from the left-side earpiece 22L to the outside. An electrode is provided on the entirety or part of the outer surface (side surface, for example) of the left-side earpiece 22L. The electrode is made of conductive carbon rubber, for example. The left-side earpiece 22L itself may be made of conductive carbon rubber. For example, the entirety or part of the left-side earpiece 22L may be made of conductive rubber. That is, the entirety or part of a surface of the left-side earpiece 22L may serve as an electrode.

The left-side earpiece 22L and the electrode member 28L may be made of an elastic member. As the elastic member, a resin, such as rubber, may be used. More specifically, Si rubber (S1734 made by NOK CORPORATION) or urethane rubber may be used for the left-side earpiece 22L and the electrode member 28L. The hardness of the left-side earpiece 22L and that of the electrode member 28L in compliance with the standard of durometer type A (instantaneous) are 40 to 75. For example, a resin having a hardness of 70 may be used for the left-side earpiece 22L and the electrode member 28L.

The left-side earpiece 22L is inserted into and is placed in the ear canal of the left ear of a user so as to contact the ear canal. The electrode member 28L supported by the left-side support 24L is placed on the left ear so as to contact the cavity of concha. This will be discussed in detail later.

The left-side ear hanger 26L generally has a curved shape. When a user wears the left-side earphone 16L, the left-side ear hanger 26L is hung on the left ear. For example, the left-side ear hanger 26L is hung on the helix of the left ear. More specifically, the left-side ear hanger 26L is placed on the back side of the helix of the left ear so as to contact the helix. One end of the left-side ear hanger 26L is connected to the front side of the left-side housing 20L and is curved toward the back side of the left-side housing 20L. When the user wears the left-side earphone 16L, this curved portion is placed on the back side of the helix of the left ear so as to touch the helix. For example, the curved portion is formed to match the shape of the back side of the helix of the left ear. The other end of the left-side ear hanger 26L is connected to one end of the cable 18.

The left-side earpiece 22L and the left-side support 24L are replaceable. For example, multiple (three to five) types of left-side earpieces 22L and those of left-side supports 24L of different shapes and different sizes are prepared, and a suitable left-side earpiece 22L and a suitable left-side support 24L are selected in accordance with the shape of the left ear (such as the shapes of the ear canal, cavity of concha, and other parts) of a user.

The controller, the communication unit, the electronic circuit, the 6-axis sensor, the memory, and other elements provided in the right-side housing 20R may be stored in one or both of the right-side housing 20R and the left-side housing 20L.

A power button and a volume control switch, for example, are provided in the right-side housing 20R or the left-side housing 20L. They may be provided both in the right-side housing 20R and the left-side housing 20L.

One of the electrode disposed in the right-side earpiece 22R and that in the left-side earpiece 22L is used as a sensor electrode, and the other one of the electrodes is used as a reference electrode. The electrode members 28R and 28L are used as ground electrodes. Alternatively, one of the electrode members 28R and 28L may be used as a sensor electrode, while the other one of the electrode members 28R and 28L may be used as a reference electrode, and the electrode provided in the right-side earpiece 22R and that in the left-side earpiece 22L may be used as ground electrodes.

In another example, multiple electrodes may be provided separately from each other in the right-side earpiece 22R, and at least one of the multiple electrodes may be selected as a sensor electrode, a reference electrode, or a ground electrode to be used. For example, the multiple electrodes may be used as sensor electrodes, and among the sensor electrodes, the potential detected by the electrode having the highest detection sensitivity, the electrode having the smallest occurrence of noise, or the electrode having the stable level of noise may be used as the sensor potential. When the multiple electrodes provided in the right-side earpiece 22R are used as reference electrodes or ground electrodes, the reference electrode or the ground electrode to be used may be selected similarly. Multiple electrodes may be provided in each of the left-side earpiece 22L and the electrode members 28R and 28L, and the electrode to be used may be selected similarly.

As shown in FIG. 7, the electrode member 28R supported by the right-side support 24R is disposed at a position separated from the right-side housing 20R by an amount of a height h. That is, the distance between the electrode member 28R and the right-side housing 20R is set to be the height h. The height h is set to such a degree as to prevent the interference between the right-side housing 20R and the helix of the right ear and thus to avoid the occurrence of a contact failure. More specifically, the height h is set so that the right-side housing 20R does not touch the helix of the right ear when the right-side earpiece 22R is inserted into the canal of the right ear and the right-side earphone 16R is worn on the right ear. That is, the height h is set so that the right-side housing 20R is sufficiently separated from the helix of the right ear so as not to contact the helix. This can avoid the contact between the top surface of the right-side housing 20R and the helix of the right ear. If the right-side housing 20R touches and interferes with the helix of the right ear, the right-side earpiece 22R may not be inserted into a position at which it can stably be placed in the ear canal, which may cause a contact failure between the electrode of the right-side earpiece 22R and the ear canal. Moreover, the electrode member 28R may not be located properly to contact the cavity of concha of the right ear, which may cause a contact failure between the electrode member 28R and the cavity of concha. The occurrence of a contact failure decreases the detection sensitivity for the sensor potential, reference potential, and ground potential and accordingly reduces the accuracy in monitoring biological information. As a result of setting the height h to a suitable value so that the right-side housing 20R does not touch the helix of the right ear, the interference between the right-side housing 20R and the helix of the right ear can be avoided. The right-side earpiece 22R can be inserted into a position at which it is stably located in the ear canal, thereby achieving a good contact between the electrode of the right-side earpiece 22R and the ear canal. Setting the height h to a suitable value also makes it possible to dispose the electrode member 28R properly to contact the cavity of concha of the right ear, thereby achieving a good contact between the electrode member 28R and the cavity of concha. As a result, the detection sensitivity for bioelectric potentials is improved. The above-described height h is also set to be a suitable value in the left-side earphone 16L.

As shown in FIG. 3, when the right-side earphone 16R is viewed from above, the right-side ear hanger 26R is displaced from the right-side housing 20R in the direction in which the right-side earpiece 22R is located. That is, in a plan view of the right-side earphone 16R, a gap is formed between the right-side housing 20R and the right-side ear hanger 26R. The gap is a space for the right ear, and the right ear is fit in this space. The right ear can be inserted into the space regardless of its size, and the right-side earphone 16R can be stably worn on the right ear. This can achieve a good contact between the electrode of the right-side earpiece 22R and the ear canal and between the electrode member 28R and the cavity of concha. The above-described gap is also provided between the left-side housing 20L and the left-side ear hanger 26L in the left-side earphone 16L.

As shown in FIG. 8, a conductive tube member 30R made of a metal is provided to protrude from the right-side support 24R in the direction in which it is separated from the right-side housing 20R. The rear end of the conductive tube member 30R is placed at the right-side support 24R, while the forward end is covered by the right-side earpiece 22R. For example, the rear end of the conductive tube member 30R is screwed into the forward end of the right-side support 24R. A conductive tube member 32R made of a metal is provided on the side surface of the right-side support 24R in the direction in which it protrudes from this side surface. The ring-like electrode member 28R is fit on the side surface of the right-side support 24R to cover the conductive tube member 32R. More specifically, a groove is formed on the side surface of the right-side support 24R in the circumferential direction, and a hole 24R1 is formed in the groove to receive one end of the conductive tube member 32R. This end of the conductive tube member 32R is screwed into the hole 24R1, so that the conductive tube member 32R is fixed to the side surface of the right-side support 24R. In the state in which the conductive tube member 32R is fixed to the side surface of the right-side support 24R, the electrode member 28R is fit into the groove on the side surface of the right-side support 24R. In this manner, the electrode member 28R is fixed on the side surface of the right-side support 24R while contacting the conductive tube member 32R. The conductive tube member 32R is connected to an electrical wire inside the right-side support 24R. A potential signal indicating a potential detected by the electrode member 28R is transmitted to the electrical wire via the conductive tube member 32R and is then output to a main substrate 34, which will be discussed later, via the electrical wire. The internal configuration of the left-side earphone 16L is similar to that of the right-side earphone 16R described above.

As shown in FIG. 9, the main substrate 34 and a sub-substrate 36 are stored in the right-side housing 20R. Details of the main substrate 34 and the sub-substrate 36 will be discussed later. Substrates other than the main substrate 34 and the sub-substrate 36 may be stored in the left-side housing 20L.

As shown in FIG. 10, a battery 38 and a relay board 40 are stored in the left-side housing 20L. Power is supplied from the battery 38 to the right-side earphone 16R and the left-side earphone 16L via the relay board 40.

The cable 18 is hard enough to maintain the overall shape of the cable 18. For example, the cable 18 is formed in a shape in which it extends from the right-side housing 20R and the left-side housing 20L in the back direction so that the cable 18 does not touch the back of the head or the hair when the biological information monitoring apparatus 12 is worn on the ears of a user. This avoids the occurrence of noise in biological information, which would otherwise be produced as a result of the cable 18 touching the back of the head or the hair.

Even if the cable 18 touches the back of the head, for example, the resulting load is transmitted to the cable 18, and the entirety of the left-side earphone 16L is rotated in the back direction, as indicated by the arrow Y in FIG. 4. This can fix the left-side earpiece 22L and the electrode member 28L to the left ear more firmly. That is, the entirety of the left-side earphone 16L is rotated in the direction in which the left-side earpiece 22L and the electrode member 28L are fixed more firmly. This achieves a good contact between the electrode of the left-side earpiece 22L and the ear canal and between the electrode member 28L and the cavity of concha, thereby enhancing the detection sensitivity. When the cable 18 touches the back of the head, the entirety of the right-side earphone 16R is also rotated similarly to the left-side earphone 16L.

Figure 11:
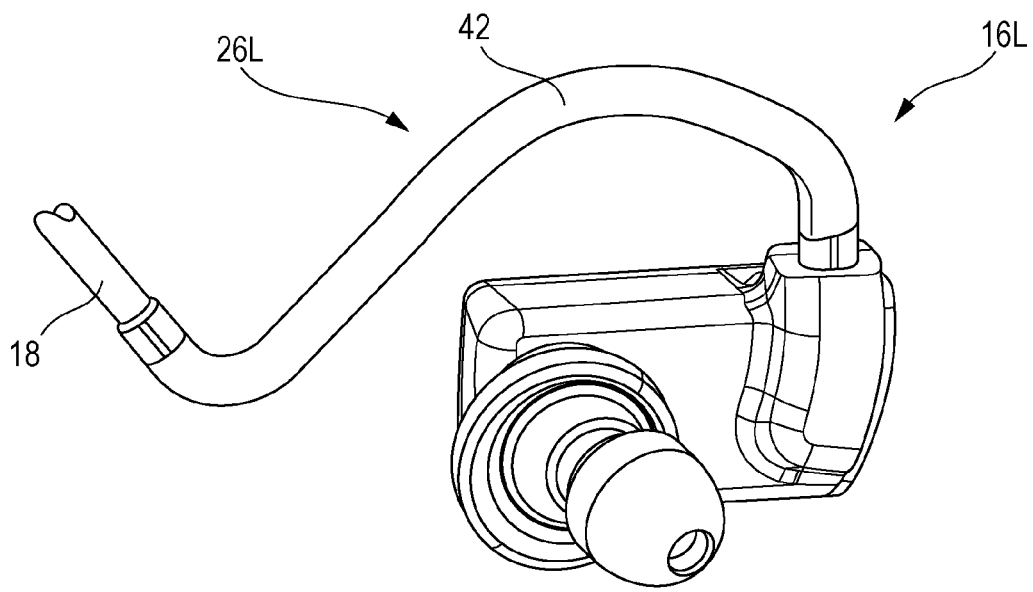
FIGS. 11 and 12 are perspective views of the left-side earphone.
Figure 12:
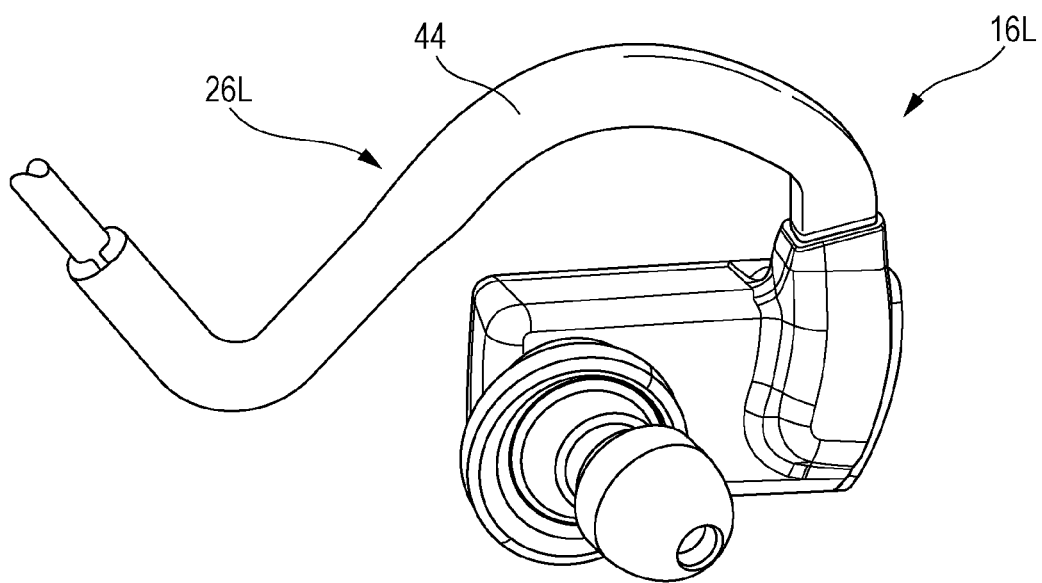
Figure 13:
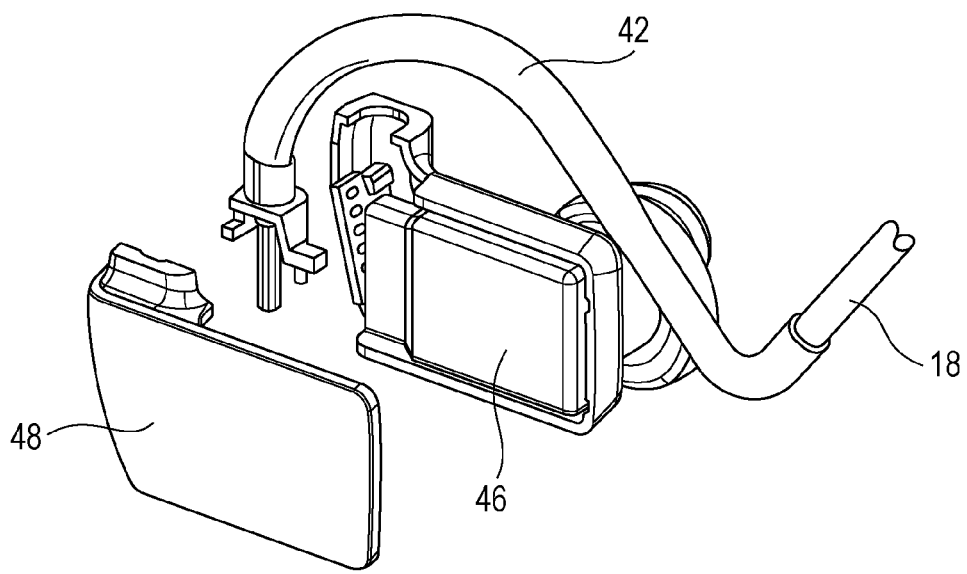
FIGS. 13 and 14 are exploded perspective views of the left-side earphone.
Figure 14:
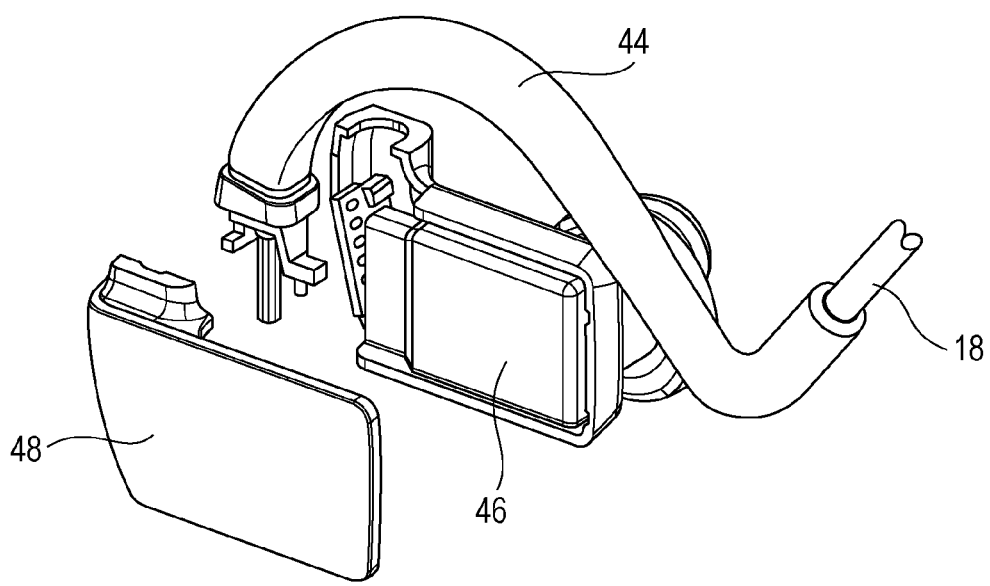

The ear hangers will be explained below with reference to FIGS. 11 through 14. FIGS. 11 and 12 are perspective views of the left-side earphone 16L. FIGS. 13 and 14 are exploded perspective views of the left-side earphone 16L.

The left-side ear hanger 26L includes a cover 42 that covers the cable 18 and a hanger member 44 that covers the cover 42. The hanger member 44 is not shown in FIGS. 11 and 13. The cable 18 on which the left-side ear hanger 26L is formed is covered with the cover 42. The hanger member 44 is shown in FIGS. 12 and 14. The hanger member 44 is disposed to cover the cover 42.

As shown in FIGS. 13 and 14, the left-side housing 20L is constituted by housing members 46 and 48. The left-side ear hanger 26L is fixed to the left-side housing 20L as a result of the forward end of the cover 42 (that is, the portion of the left-side ear hanger 26L to be attached to the left-side housing 20L) being sandwiched between the housing members 46 and 48. The forward end of the hanger member 44, as well as that of the cover 42, may also be sandwiched between the housing members 46 and 48. The right-side ear hanger 26R is configured similarly to the left-side ear hanger 26L.

The cover 42 is made of nylon, for example, and the hanger member 44 is made of silicon rubber, for example. Using nylon for the cover 42 can prevent the hanger member 44 from breaking off from its base which is fixed to the left-side housing 20L. The cover 42 and the hanger member 44 can bend the cable 18 so that it can be prevented from touching a user when the user wears the biological information monitoring apparatus 12. The right-side ear hanger 26R is configured similarly to the left-side ear hanger 26L.

Figure 15:
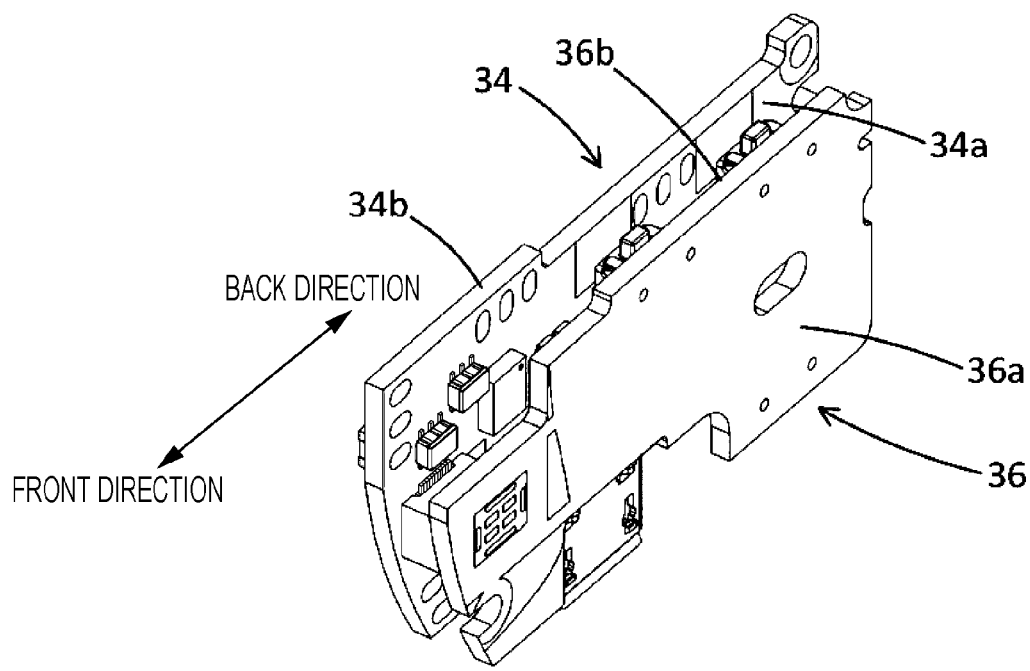
FIG. 15 is a perspective view illustrating a main substrate and a sub-substrate.

The main substrate 34 and the sub-substrate 36 will be explained below. FIG. 15 is a perspective view illustrating the positional relationship between the main substrate 34 and the sub-substrate 36. A description will be given, assuming that biological information is brain waves and the main substrate 34 and the sub-substrate 36 include elements such as an electronic circuit for extracting brain waves from a potential signal indicating potentials detected by the electrodes.

The main substrate 34 has an inner surface 34a and an outer surface 34b. The inner surface 34a opposes the head of a user wearing the right-side earphone 16R. The outer surface 34b is the surface opposite the inner surface 34a. The sub-substrate 36 has an inner surface 36a and an outer surface 36b. The inner surface 36a opposes the head of a user wearing the right-side earphone 16R. The outer surface 36b is the surface opposite the inner surface 36a.

Figure 16:
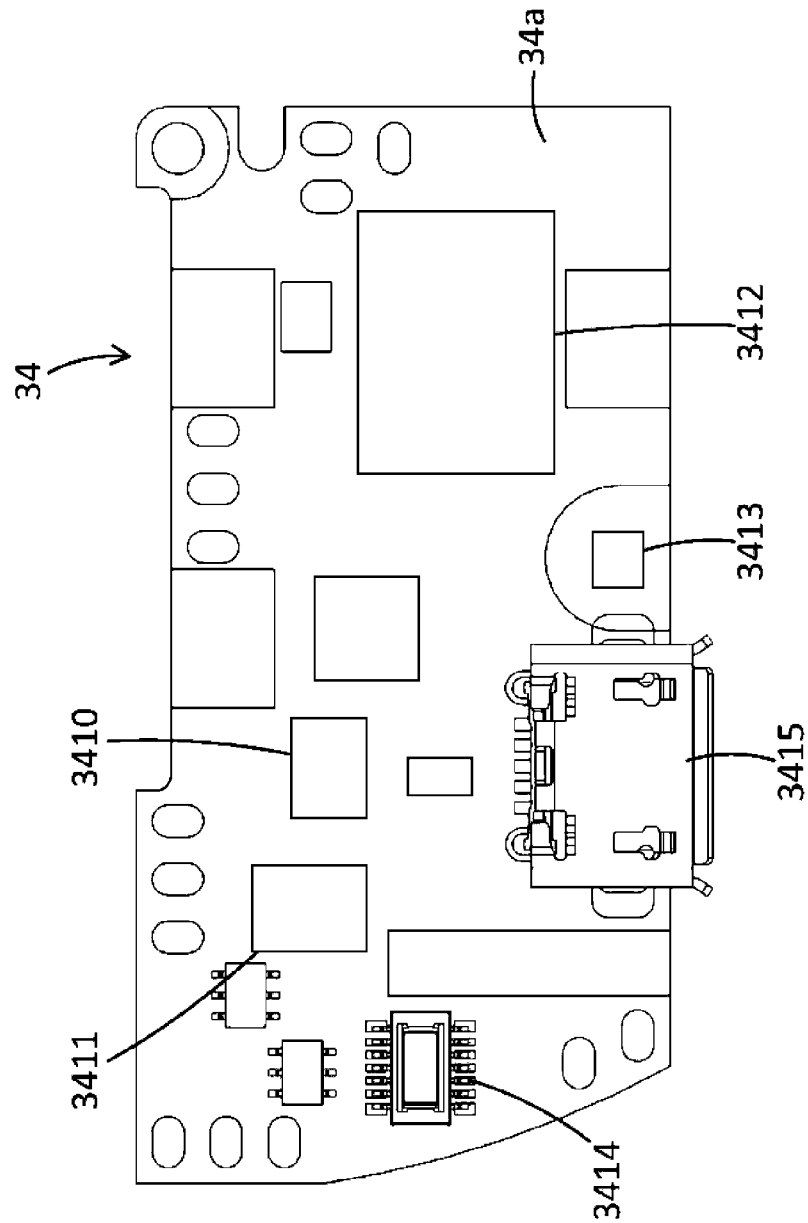
FIG. 16 illustrates the inner surface of the main substrate.
Figure 17:
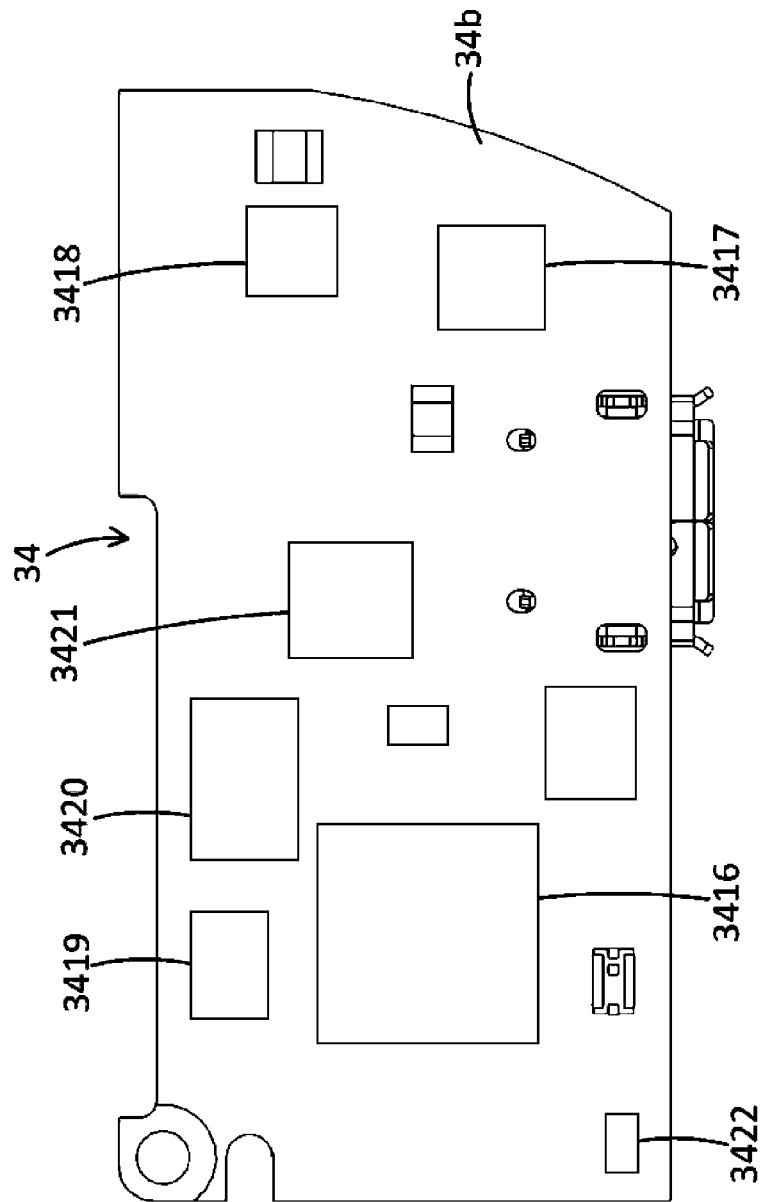
FIG. 17 illustrates the outer surface of the main substrate.

FIG. 16 illustrates the inner surface 34a of the main substrate 34. FIG. 17 illustrates the outer surface 34b of the main substrate 34.

As shown in FIG. 16, a brain wave sensor 3410, a 6-axis sensor 3411, a flash memory 3412, a light-emitting diode (LED) 3413, a board-to-board connector 3414, and a universal serial bus (USB) terminal 3415, for example, are disposed on the inner surface 34a of the main substrate 34. The brain wave sensor 3410 analyzes a potential signal indicating detected potentials so as to extract brain waves from the potential signal.

As shown in FIG. 17, a communication chip 3416 for performing communication based on Bluetooth, a charging control integrated circuit (IC) 3417 for controlling the charging of the battery, a buck-boost converter 3418, a serial peripheral interface (SPI) memory 3419, a static random access memory (SRAM) 3420, a memory control unit (MCU) 3421, and an antenna 3422 are disposed on the outer surface 34b of the main substrate 34.

Figure 18:
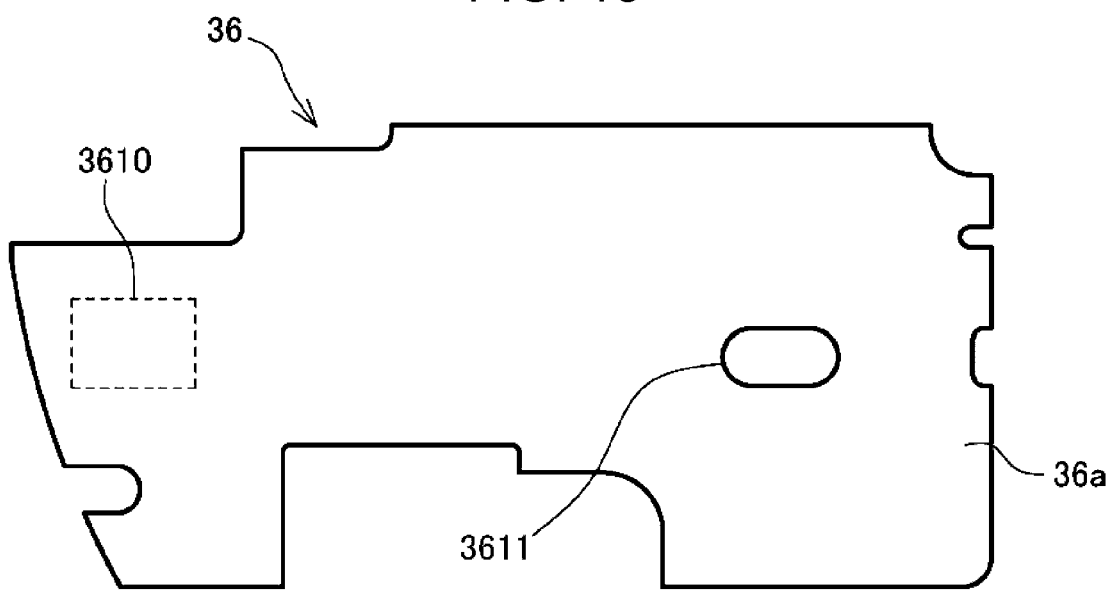
FIG. 18 illustrates the inner surface of the sub-substrate.
Figure 19:
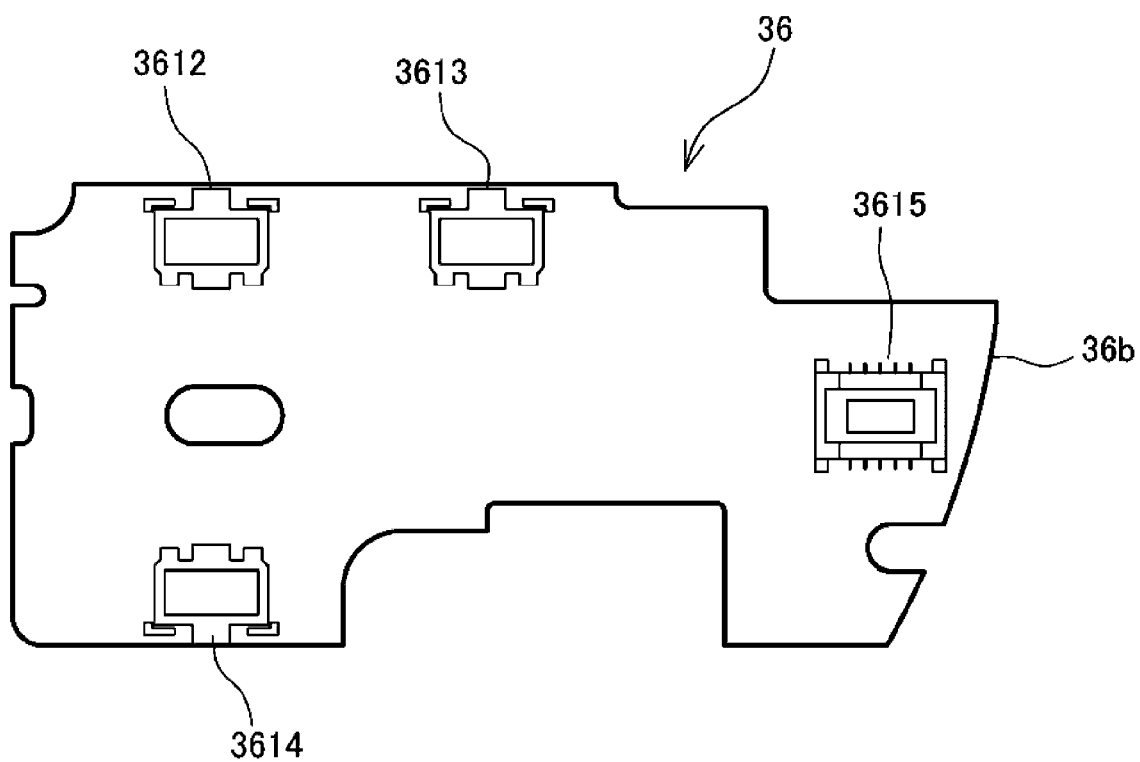
FIG. 19 illustrates the outer surface of the sub-substrate.

FIG. 18 illustrates the inner surface 36a of the sub-substrate 36. FIG. 19 illustrates the outer surface 36b of the sub-substrate 36.

As shown in FIG. 18, a microphone 3610 is disposed on the inner surface 36a of the sub-substrate 36. A through-hole 3611 is also formed to pass through the sub-substrate 36 in the thickness direction. The through-hole 3611 is a hole for wiring.

As shown in FIG. 19, volume control switches 3612 and 3613, a switch 3614 for setting the functions of the biological information monitoring apparatus 12, and a board-to-board connector 3615 are disposed on the outer surface 36b of the sub-substrate 36.

Figure 20:
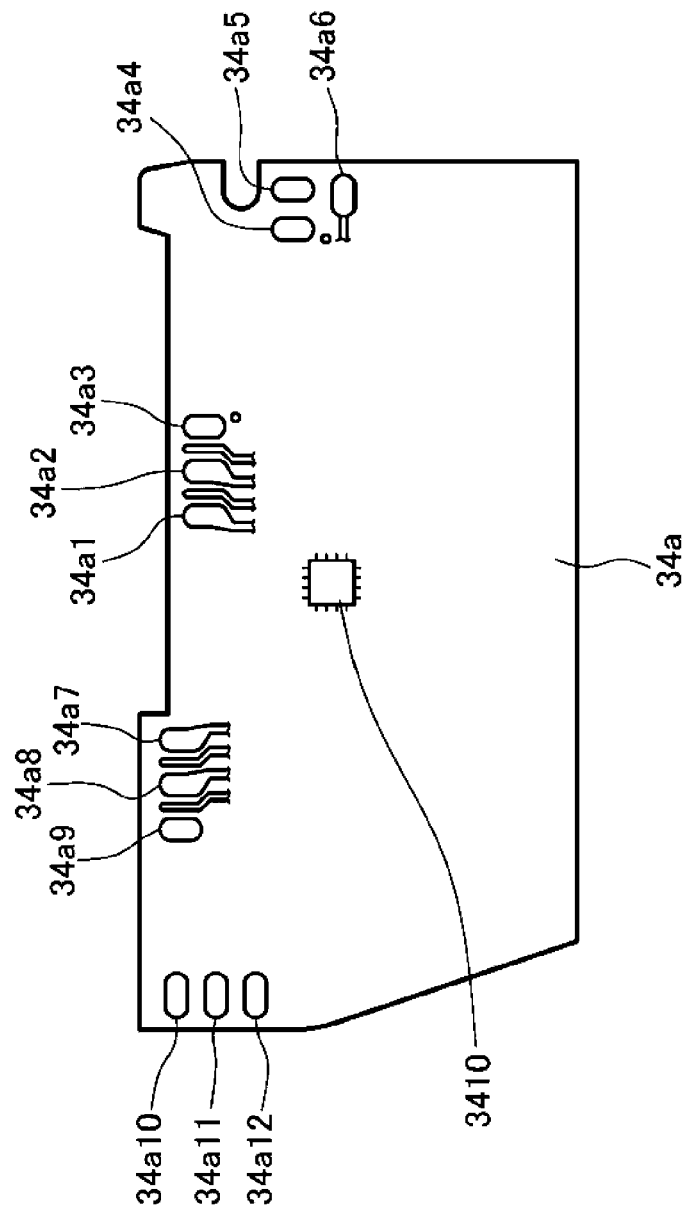
FIG. 20 illustrates wiring on the inner surface of the main substrate.

FIG. 20 illustrates electrode pads on the inner surface 34a of the main substrate 34. In FIG. 20, only the brain wave sensor 3410 and the electrode pads are shown and electrical wires on the main substrate 34 are not shown.

Electrode pads 34a1 and 34a2 are connected to electrodes provided in the right-side earphone 16R via electrical wires. For example, the electrode pad 34a1 is connected to one of the electrode in the right-side earpiece 22R and the electrode of the electrode member 28R via an electrical wire, while the electrode pad 34a2 is connected to the other one of the electrodes via an electrical wire. The electrode pads 34a1 and 34a2 are connected to the brain wave sensor 3410 via electrical wires formed on the main substrate 34. An electrode pad 34a3 is connected to a shielding ground electrode. The two electrical wires connected to the electrode pads 34a1 and 34a2 are bundled together by a shield line and extend to and are connected to the electrode provided in the right-side earpiece 22R and to the electrode member 28R via the through-hole 3611 formed in the sub-substrate 36.

Electrode pads 34a4 and 34a5 are connected to the speaker provided in the right-side earphone 16R via electrical wires. An electrode pad 34a6 is connected to a shielding ground electrode. The two electrical wires connected to the electrode pads 34a4 and 34a5 are bundled together by a shield line and are connected to the speaker.

Electrode pads 34a7 and 34a8 are connected to electrodes provided in the left-side earphone 16L via electrical wires. For example, the electrode pad 34a7 is connected to one of the electrode in the left-side earpiece 22L and the electrode of the electrode member 28L via an electrical wire, while the electrode pad 34a8 is connected to the other one of the electrodes via an electrical wire. The electrode pads 34a7 and 34a8 are connected to the brain wave sensor 3410 via electrical wires formed on the main substrate 34. An electrode pad 34a9 is connected to a shielding ground electrode. The two electrical wires connected to the electrode pads 34a7 and 34a8 are bundled together by a shield line and extend to and are connected to the electrode provided in the left-side earpiece 22L and to the electrode member 28L.

Electrode pads 34a10 and 34a11 are connected to the speaker provided in the left-side earphone 16L via electrical wires. An electrode pad 34a12 is connected to a shielding ground electrode. The two electrical wires connected to the electrode pads 34a10 and 34a11 are bundled together by a shield line and are connected to the speaker.

Electrode pads (such as the electrode pads 34a1, 34a2, 34a7, and 34a8) for monitoring brain waves are disposed closer to the brain wave sensor 3410 than the other electrode pads are. This can reduce the influence of noise occurring in wiring between the brain wave sensor 3410 and the electrode pads for monitoring brain waves. The communication chip 3416 and the charging control IC 3417 are not disposed between the brain wave sensor 3410 and the electrode pads for monitoring brain waves. This can reduce the influence of noise occurring in the communication chip 3416 and the charging control IC 3417.

A group of the electrical wires connected to the electrode pads for monitoring brain waves and a group of the electrical wires used for the electrode pads connected to the speakers are laid separately from each other on the main substrate 34. This can reduce the occurrence of crosstalk between the two groups of electrical wires.

Figure 21:
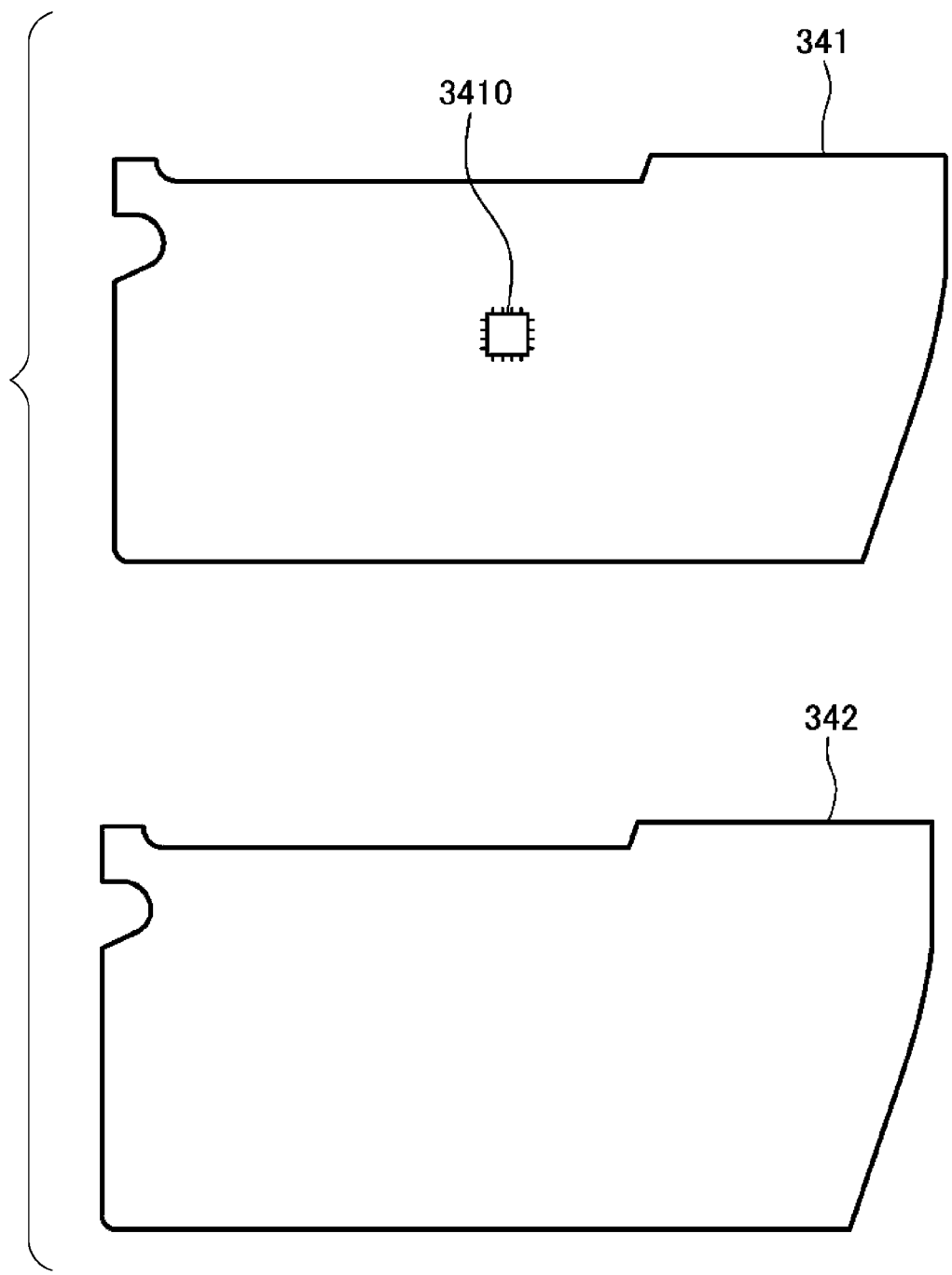
FIG. 21 illustrates substrate parts included in the main substrate.

The main substrate 34 may be a multilayer substrate. FIG. 21 illustrates substrate parts 341 and 342 included in the main substrate 34. The substrate parts 341 and 342 form different layers of the multilayer substrate. The brain wave sensor 3410 is provided in the substrate part 341. The substrate part 342 is a shield ground (SGND) substrate and is overlaid on the substrate part 341. Bioelectric potentials are input into the brain wave sensor 3410. The substrate part 342, which is an SGND substrate, is overlaid on the substrate part 341 in which the brain wave sensor 3410 is provided, thereby reducing noise occurring in bioelectric potentials.

Figure 22:
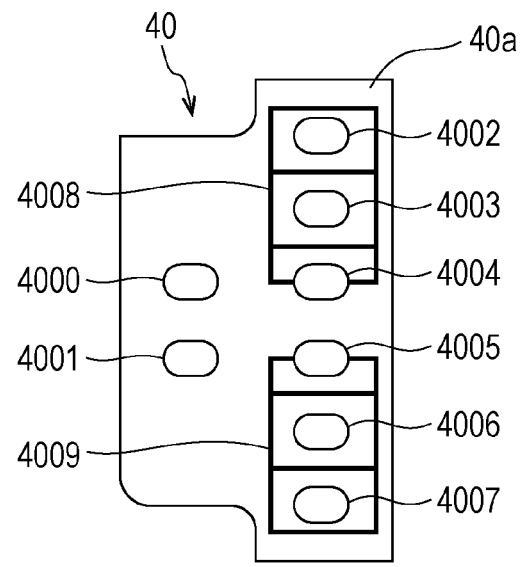
FIG. 22 illustrates wiring on the front surface of a relay board.
Figure 23:
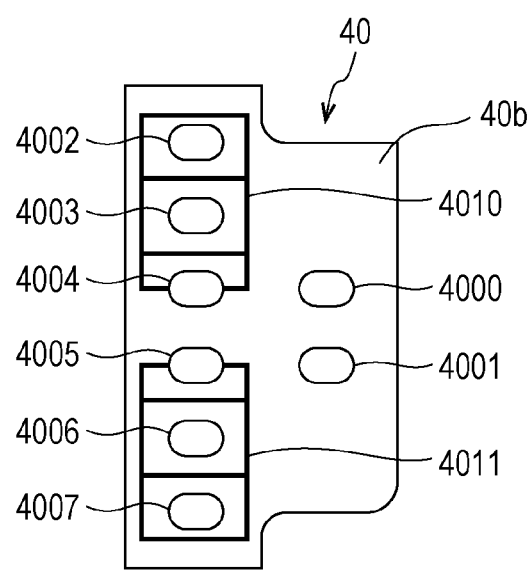
FIG. 23 illustrates wiring on the back surface of the relay board.

FIG. 22 illustrates wiring on a front surface 40a of the relay board 40. FIG. 23 illustrates wiring on a back surface 40b of the relay board 40.

An electrode pad 4000 is connected to the negative terminal of the battery 38 (see FIG. 10), while an electrode pad 4001 is connected to the positive terminal of the battery 38.

Electrode pads 4002 and 4003 are connected to the electrodes provided in the left-side earphone 16L via electrical wires. For example, the electrode pad 4002 is connected to one of the electrode provided in the left-side earpiece 22L or the electrode of the electrode member 28L via an electrical wire, while the electrode pad 4003 is connected to the other one of the electrodes via an electrical wire. For example, the electrode pad 4002 is connected to the electrode provided in the left-side earpiece 22L, while the electrode pad 4003 is connected to the electrode of the electrode member 28L. An electrode pad 4004 is connected to a shielding ground electrode.

Electrode pads 4006 and 4007 are audio electrode pads and are connected to the speaker of the left-side earphone 16L via electrical wires. An electrode pad 4005 is connected to a shielding ground electrode.

The electrode pads 4002 and 4003 are surrounded by a noise shields 4008 and 4010, while the electrode pads 4006 and 4007 are surrounded by noise shields 4009 and 4011.

A group of the electrode pads 4005 through 4007 used for audio signals and a group of the electrode pads 4002 through 4004 connected to the electrodes for detecting bioelectric potentials are disposed separately from each other, and are surrounded by the corresponding shields. This arrangement can reduce the occurrence of noise in bioelectric potentials caused by audio signals.

A group of the electrode pads 4000 and 4001 used for the battery 38 and a group of the electrode pads 4002 through 4004 are disposed separately from each other, and the electrode pads 4002 through 4004 are surrounded by the shields. This can reduce the occurrence of noise in bioelectric potentials caused by the battery 38.

Figure 24:
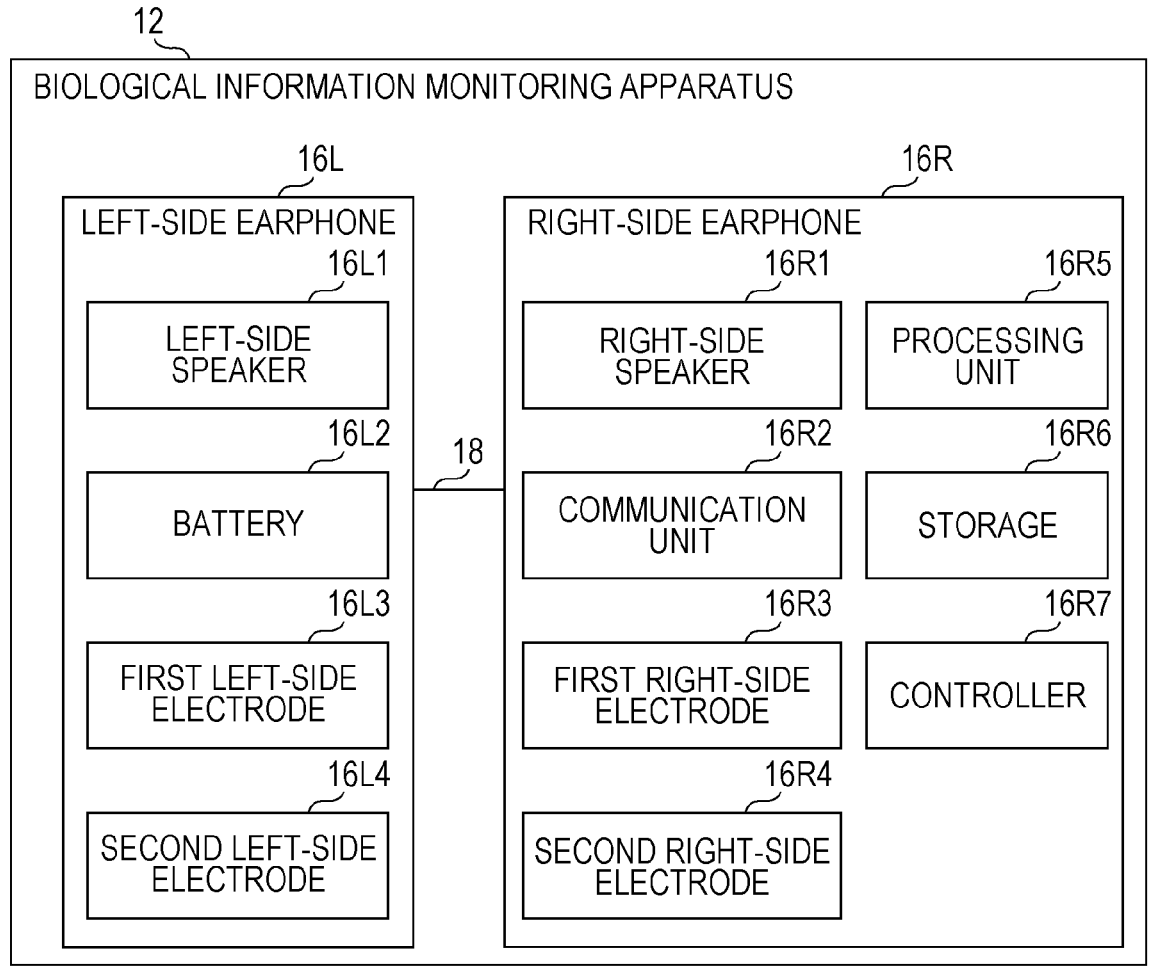
FIG. 24 is a block diagram illustrating functions of the biological information monitoring apparatus.

Functions of the biological information monitoring apparatus 12 will be described below in detail with reference to the block diagram of FIG. 24.

As described above, the biological information monitoring apparatus 12 includes the right-side earphone 16R, the left-side earphone 16L, and the cable 18. The right-side earphone 16R and the left-side earphone 16L are physically connected with each other by the cable 18 and send and receive data with each other via the cable 18.

The right-side earphone 16R includes a right-side speaker 16R1, a communication unit 16R2, a first right-side electrode 16R3, a second right-side electrode 16R4, a processing unit 16R5, a storage 16R6, and a controller 16R7.

The left-side earphone 16L includes a left-side speaker 16L1, a battery 16L2, a first left-side electrode 16L3, and a second left-side electrode 16L4.

Sound emitted from the right-side speaker 16R1 is output from the right-side earpiece 22R to the outside. Sound emitted from the left-side speaker 16L1 is output from the left-side earpiece 22L to the outside.

The communication unit 16R2 is a communication interface, such as a communication chip, and has a function of communicating with another device by wireless communication or wired communication. For example, the communication unit 16R2 sends a potential signal and biological information to an external device, such as the terminal apparatus 14, and receives information, such as control information, from an external device, such as the terminal apparatus 14.

The first right-side electrode 16R3 is the electrode provided on the outer surface of the right-side earpiece 22R. The right-side earpiece 22R itself may form the first right-side electrode 16R3. The second right-side electrode 16R4 is the electrode provided on the side surface of the right-side support 24R, that is, the electrode formed by the electrode member 28R. A potential signal indicating potentials detected by the first right-side electrode 16R3 and that by the second right-side electrode 16R4 are output to the processing unit 16R5.

The first left-side electrode 16L3 is the electrode provided on the outer surface of the left-side earpiece 22L. The left-side earpiece 22L itself may form the first left-side electrode 16L3. The second left-side electrode 16L4 is the electrode provided on the side surface of the left-side support 24L, that is, the electrode formed by the electrode member 28L. A potential signal indicating potentials detected by the first left-side electrode 16L3 and that by the second left-side electrode 16L4 are output from the left-side earphone 16L to the processing unit 16R5 of the right-side earphone 16R via the cable 18.

The above-described number of electrodes is only an example. Multiple electrodes may be disposed in each of the right-side earpiece 22R, the left-side earpiece 22L, the electrode member 28R, and the electrode member 28L.

The processing unit 16R5 analyzes potential signals indicating potentials individually detected by the first right-side electrode 16R3, the second right-side electrode 16R4, the first left-side electrode 16L3, and the second left-side electrode 16L4. As a result of analyzing a potential signal, for example, the processing unit 16R5 extracts from the potential signal a specific bioelectric potential, such as a bioelectric potential having a specific frequency, eliminates noise, and then extracts brain waves, which are an example of biological information. The functions of the processing unit 16R5 are implemented by a processor, for example. A memory may also be used to implement the functions of the processing unit 16R5. For example, the brain wave sensor 3410 may be used to implement the functions of the processing unit 16R5.

The processing unit 16R5 may analyze potential signals indicating potentials detected by two or more electrodes selected from an electrode group including the first right-side electrode 16R3, the second right-side electrode 16R4, the first left-side electrode 16L3, and the second left-side electrode 16L4.

For example, the first right-side electrode 16R3 is used as a sensor electrode, the second right-side electrode 16R4 is used as a ground electrode, and the first left-side electrode 16L3 is used as a reference electrode. In this case, the processing unit 16R5 defines the potential detected by the second right-side electrode 16R4 to be a ground potential, which is a base potential, and calculates the potential difference between the potential detected by the first right-side electrode 16R3, which is the sensor electrode, and the reference potential detected by the first left-side electrode 16L3, which is the reference electrode, as a bioelectric potential. The processing unit 16R5 may execute known statistical processing on the potential difference and set the processing result to be biological information. A potential signal indicating a bioelectric potential and biological information are temporarily stored in the storage 16R6, for example, and are then sent from the biological information monitoring apparatus 12 to an external device, such as the terminal apparatus 14, by the communication unit 16R2. Potential signals indicating potentials which have not been subjected to calculation or a potential signal indicating the potential difference which has not been subjected to statistical processing may be sent from the biological information monitoring apparatus 12 to an external device, such as the terminal apparatus 14, and a potential difference may be calculated or statistical processing may be executed in the external device.

The storage 16R6 is constituted by a memory, for example. Potential signals indicating potentials detected by the first right-side electrode 16R3, the second right-side electrode 16R4, the first left-side electrode 16L3, and the second left-side electrode 16L4 and information generated by the processing unit 16R5 may be stored in the storage 16R6.

The battery 16L2 supplies power to the individual elements of the right-side earphone 16R and the left-side earphone 16L so as to drive them. As the battery 16L2, a rechargeable/dischargeable battery is used. A non-rechargeable battery may alternatively be used. An electromagnetic-wave shielding member may be disposed around the battery 16L2 and charging-related parts. This can reduce noise caused by electromagnetic waves generated during charging.

The controller 16R7 controls the operations of the individual elements of the right-side earphone 16R and the left-side earphone 16L. The functions of the controller 16R7 are implemented by a processor, for example. A memory may also be used to implement the functions of the controller 16R7.

The communication unit 16R2, the processing unit 16R5, the storage 16R6, and the controller 16R7 may also be provided in the left-side earphone 16L, while the battery 16L2 may also be provided in the right-side earphone 16R. These components may be provided in either one of the right-side earphone 16R and the left-side earphone 16L.

The right-side earphone 16R and the left-side earphone 16L are connected with each other via the cable 18. However, the cable 18 may not be included in the biological information monitoring apparatus 12. In this case, a communication unit is also provided in the left-side earphone 16L, and the right-side earphone 16R and the left-side earphone 16L communicate with each other by using the individual communication units so as to send and receive data with each other.

Figure 25:
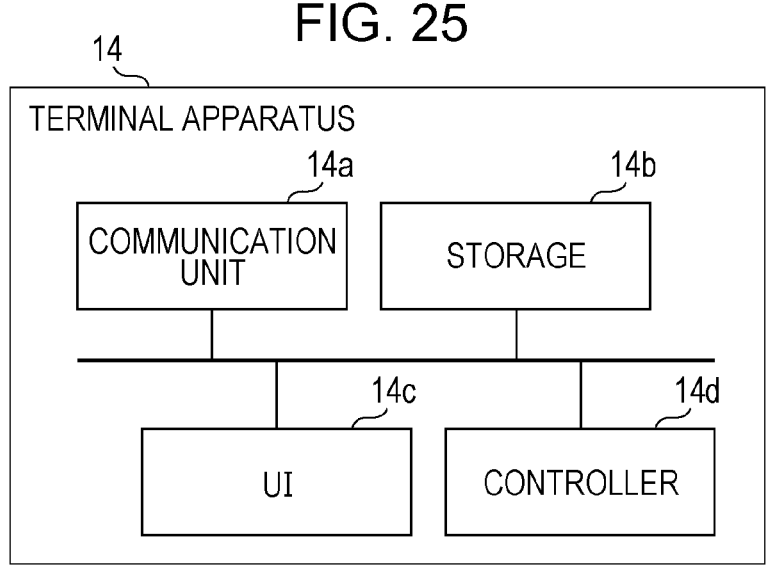
FIG. 25 is a block diagram illustrating functions of a terminal apparatus.

Functions of the terminal apparatus 14 will be described below in detail with reference to the block diagram of FIG. 25.

A communication unit 14a is a communication interface, such as a communication chip, and has a function of communicating with another device by wireless communication or wired communication.

A storage 14b is a storage device, such as a hard disk drive or a memory. Various items of data and programs, for example, are stored in the storage 14b.

A user interface (UI) 14c includes a display and an operation unit. The display is a liquid crystal display or an electroluminescence (EL) display, for example. The operation unit is an input unit, such as buttons, a keyboard, or a mouse. The UI 14c may be a touchscreen which serves both as the display and the operation unit. The UI 14c may include a microphone and/or a speaker.

A controller 14d controls the operations of the individual elements of the terminal apparatus 14. The functions of the controller 14d are implemented by a processor, for example. A memory may also be used to implement the functions of the controller 14d.

The processing unit 16R5 may be provided in the terminal apparatus 14, and the terminal apparatus 14 may execute the above-described processing executed by the processing unit 16R5.

Figure 26:
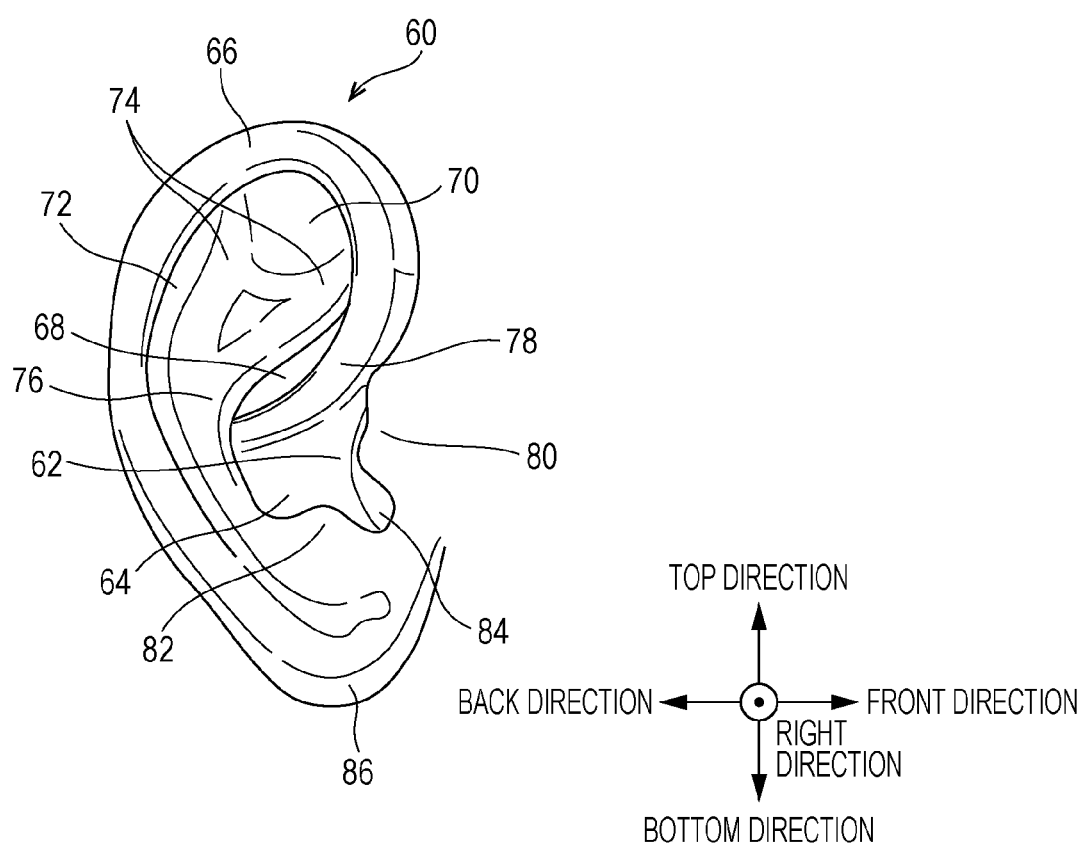
FIG. 26 schematically illustrates the external appearance of a right ear of a human.
Figure 27:
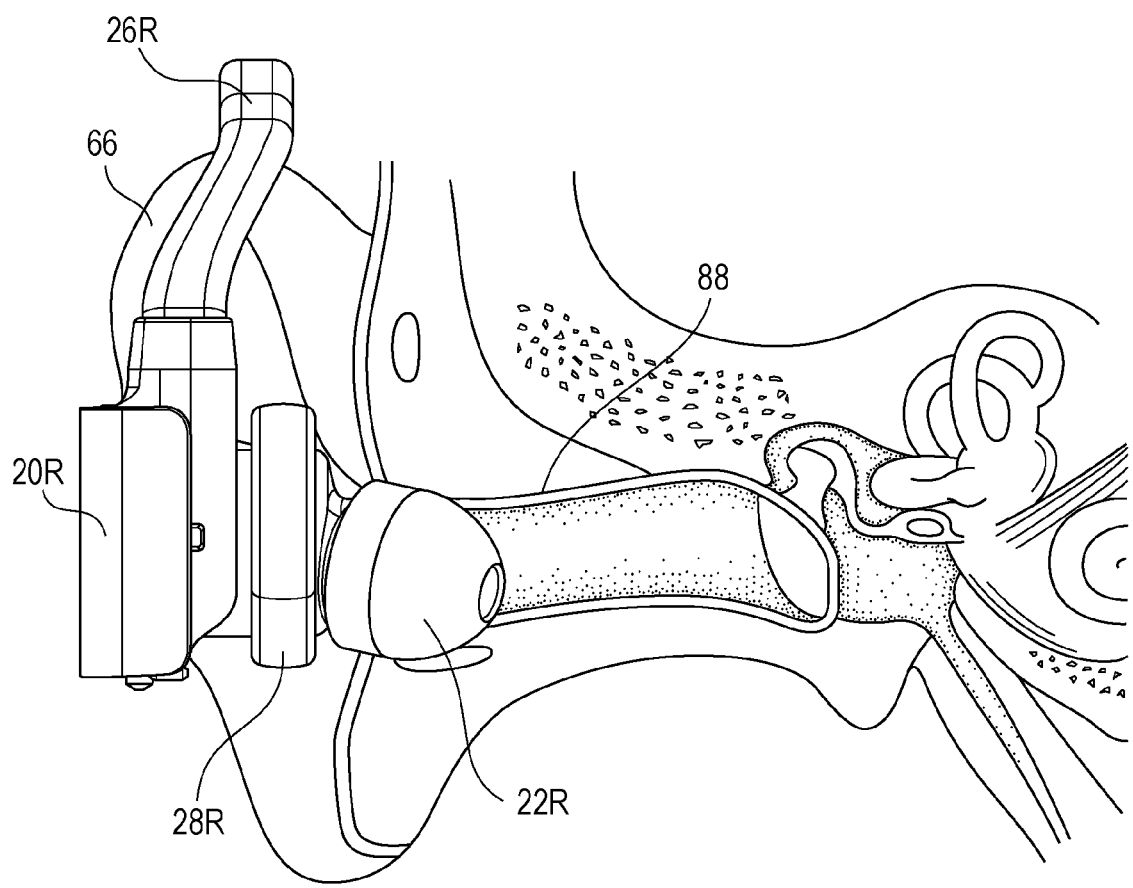
FIG. 27 schematically illustrates the external appearance and the inside of a right ear of a human.
Figure 28:
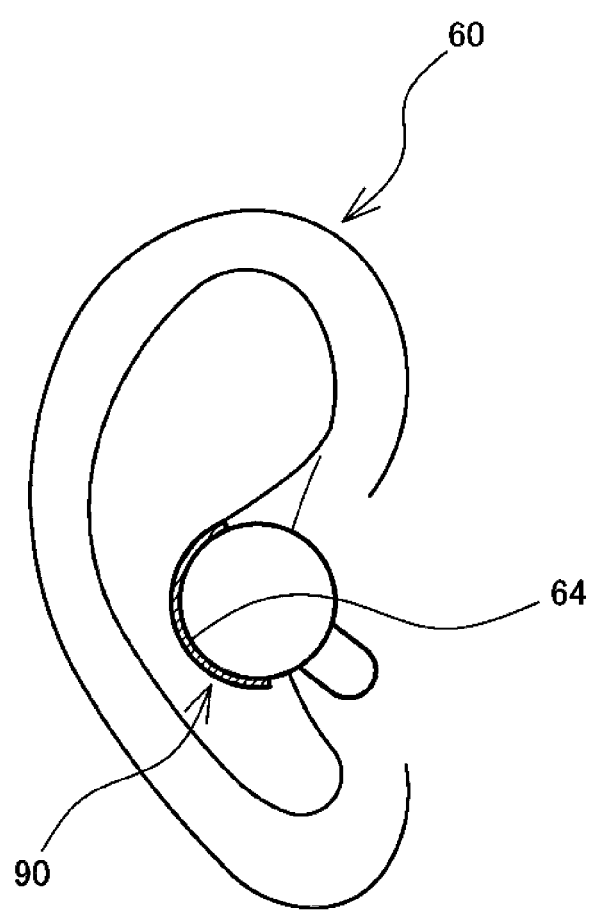
FIG. 28 schematically illustrates the external appearance of a right ear of a human.

The state of contact between the biological information monitoring apparatus 12, which is a bearable device, and an ear of a user when the biological information monitoring apparatus 12 is worn on the ear will be described below in detail with reference to FIGS. 26 through 28. FIGS. 26 and 28 schematically illustrate the external appearance of the right ear of a human. FIG. 27 schematically illustrates the external appearance and the inside of the right ear of a human.

As shown in FIG. 26, an ear 60 includes an external acoustic opening 62 which leads to an ear canal 88 and parts around the external acoustic opening 62, such as a cavity of concha 64, a helix 66, a concha of auricle 68, a triangular fossa 70, a scapha 72, a pair of crura antihelices 74, an antihelix 76, a crus of helix 78, a tragus 80, an antitragus 82, an intertragic notch 84, and a lobule 86.

The right-side earphone 16R worn on the ear (right ear) 60 is shown in FIG. 27. A portion 90 of the electrode member 28R brought into contact with the right ear 60 is shown in FIG. 28.

The right-side ear hanger 26R is hung on the right ear 60, and in this state, the right-side earpiece 22R is inserted into the ear canal 88. The outer surface of the right-side earpiece 22R is then brought into contact with the surface (skin) of the ear canal 88. The right-side earpiece 22R, which is made of an elastic member, is deformed to match the shape of the ear canal 88, which allows the outer surface of the right-side earpiece 22R to closely contact the surface of the ear canal 88. This achieves close contact between the electrode provided on the outer surface of the right-side earpiece 22R and the surface of the ear canal 88.

The electrode member 28R contacts the cavity of concha 64. The electrode member 28R, which is made of an elastic member, is deformed to match the shape of the cavity of concha 64 and is brought into close contact with it. This achieves close contact between the electrode provided on the outer surface of the electrode member 28R and the cavity of concha 64, for example, the edge of the cavity of concha 64.

When the right-side earphone 16R configured as described above is worn on the right ear 60, the movement thereof is restricted. This will be discussed below in detail.

The right ear 60 is positioned between the lower portion of the right-side ear hanger 26R and the upper portion of the electrode member 28R and is sandwiched therebetween in the top-bottom direction. This restricts the movement of the right-side earphone 16R in the top-bottom direction.

The right portion of the right-side ear hanger 26R contacts the helix of the right ear 60, and a friction force is produced between the outer surface of the right-side earpiece 22R and the ear canal 88. This restricts the movement of the right-side earphone 16R in the left-right direction.

The right ear 60 is sandwiched between the portion of the right-side ear hanger 26R contacting the back side of the right ear 60 and the back portion of the electrode member 28R in the front-back direction. This restricts the movement of the right-side earphone 16R in the front-back direction.

In this manner, the movement of the right-side earphone 16R is constrained. This can substantially maintain and stabilize the contact between the electrodes provided in the right-side earphone 16R and the skin of the right ear 60. It is thus possible to prevent or reduce the occurrence of noise mixed into bioelectric potentials, which would be caused by an unstable contact between the electrodes and the skin, thereby enhancing the accuracy in monitoring biological information. For example, even if a user having the biological information monitoring apparatus 12 mounted thereon moves, the movement of the right-side earphone 16R is constrained as described above, thereby making it possible to prevent or reduce the occurrence of noise.

Depending on the shape of the ear or the head of a user, the right ear 60 (the base of the right ear 60, for example) may be sandwiched between the lower portion of the right-side ear hanger 26R and the upper portion of the right-side earpiece 22R. This may also restrict the movement of the right-side earphone 16R in the top-bottom direction. The right ear 60 (the base of the right ear 60, for example) may also be sandwiched between the portion of the right-side ear hanger 26R contacting the back side of the right ear 60 and the back portion of the right-side earpiece 22R. This may also restrict the movement of the right-side earphone 16R in the front-back direction.

As described above, the right-side earpiece 22R, the electrode member 28R, and the right-side ear hanger 26R serve the function of positioning the right-side earphone 16R. That is, these elements contribute to positioning the electrodes to be brought into contact with the skin by restricting the movements of the right-side earphone 16R.

The left-side earphone 16L is configured similarly to the right-side earphone 16R. In the left-side earphone 16L, the left-side earpiece 22L is inserted into the ear canal of the left ear, and the electrode provided on the left-side earpiece 22L is brought into contact with the surface of the ear canal.

The shapes of the ears are different depending on individual users. However, such individual differences can be absorbed by selecting a suitable size and shape of the right-side earpiece 22R, the electrode member 28R, the left-side earpiece 22L, and/or the electrode member 28L among different sizes and shapes.

Figure 29:
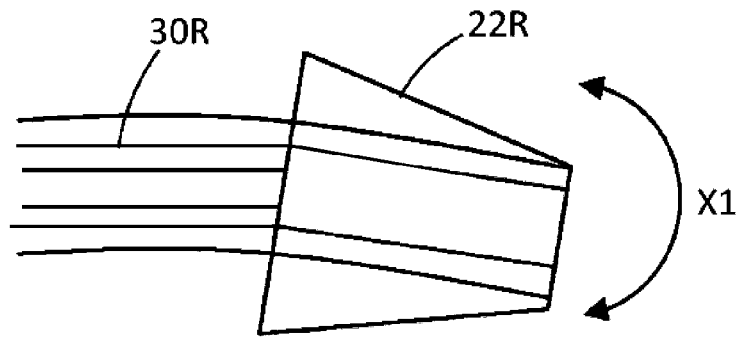
FIGS. 29, 30, and 31 schematically illustrate a right-side earpiece and a conductive tube member.
Figure 30:
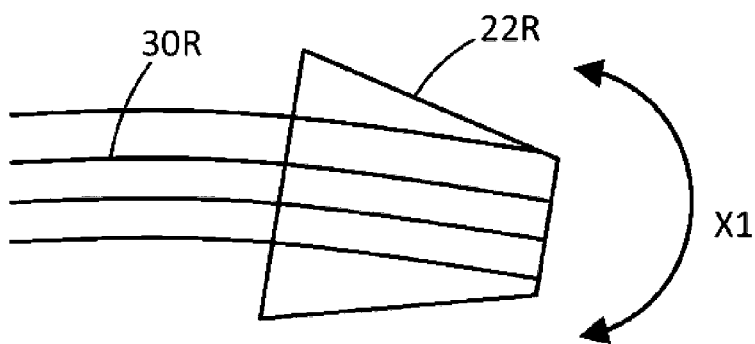
Figure 31:
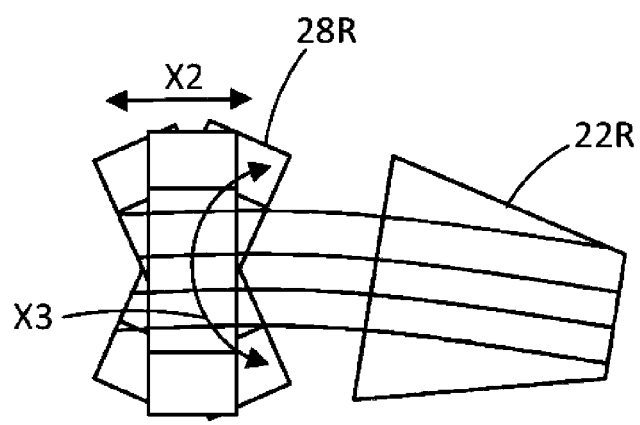

The right-side earpiece 22R may be swingable about the portion supported by the conductive tube member 30R as the axis. This will be explained below with reference to FIGS. 29 through 31. FIGS. 29 through 31 schematically illustrate the right-side earpiece 22R and the conductive tube member 30R.

As shown in FIG. 29, the right-side earpiece 22R is provided at and supported by the forward end of the conductive tube member 30R such that it is swingable in the direction indicated by the arrow X1 in FIG. 29. For example, the right-side earpiece 22R, which is made of conductive rubber, swings by utilizing its low stiffness (high flexibility). Alternatively, a spring member may be disposed in a coil-like shape or along the conductive tube member 30R, thereby causing the right-side earpiece 22R to swing. The left-side earpiece 22L may also be swingable about the portion supported by a left-side conductive tube member as the axis.

In another example, as shown in FIG. 30, the conductive tube member 30R itself may be swingable about the portion supported by the right-side housing 20R, for example, as the axis in the direction indicated by the arrow X1 in FIG. 30. Swinging the conductive tube member 30R itself can tilt the right-side earpiece 22R. For example, the conductive tube member 30R may be made of a resin, such as rubber, or a spring member may be disposed in a coil-like shape or along the conductive tube member 30R, thereby causing the conductive tube member 30R to swing. The conductive tube member provided in the left-side earphone 16L may also be swingable, as in the conductive tube member 30R.

Tilting the right-side earpiece 22R can adjust the angle of the surface of the right-side earpiece 22R which contacts the ear canal. This makes it possible to bring the right-side earpiece 22R into close contact with the ear canal, thereby enhancing the detection sensitivity of the electrode provided in the right-side earpiece 22R. The shapes of the ears are different depending on individual users. However, such individual differences can be absorbed since the right-side earpiece 22R tilts when being inserted into the ear canal. This achieves close contact between the electrode provided on the right-side earpiece 22R and the ear canal. The left-side earpiece 22L may be configured similarly to the right-side earpiece 22R.

In another example, the member which contacts the cavity of concha may be movable. For example, as shown in FIG. 31, the electrode member 28R which contacts the cavity of concha may be movable outwardly (in the direction separate from the ear canal, for example) and inwardly (in the direction closer to the ear canal, for example), as indicated by the arrow X2 in FIG. 31. More specifically, the right-side support 24R supporting the electrode member 28R may be movable in the direction indicated by the arrow X2 in FIG. 31. The right-side support 24R may be swingable about the portion supported by the right-side housing 20R as the axis in the direction indicated by the arrow X3 in FIG. 31. Moving the electrode member 28R makes it possible to bring the electrode member 28R into close contact with the cavity of concha, thereby enhancing the detection sensitivity. The electrode member 28L may also be configured similarly to the electrode member 28R. More specifically, the left-side support 24L may also be movable in the direction indicated by the arrow X2 and be swingable in the direction indicated by the arrow X3 in FIG. 31.

Figure 32:
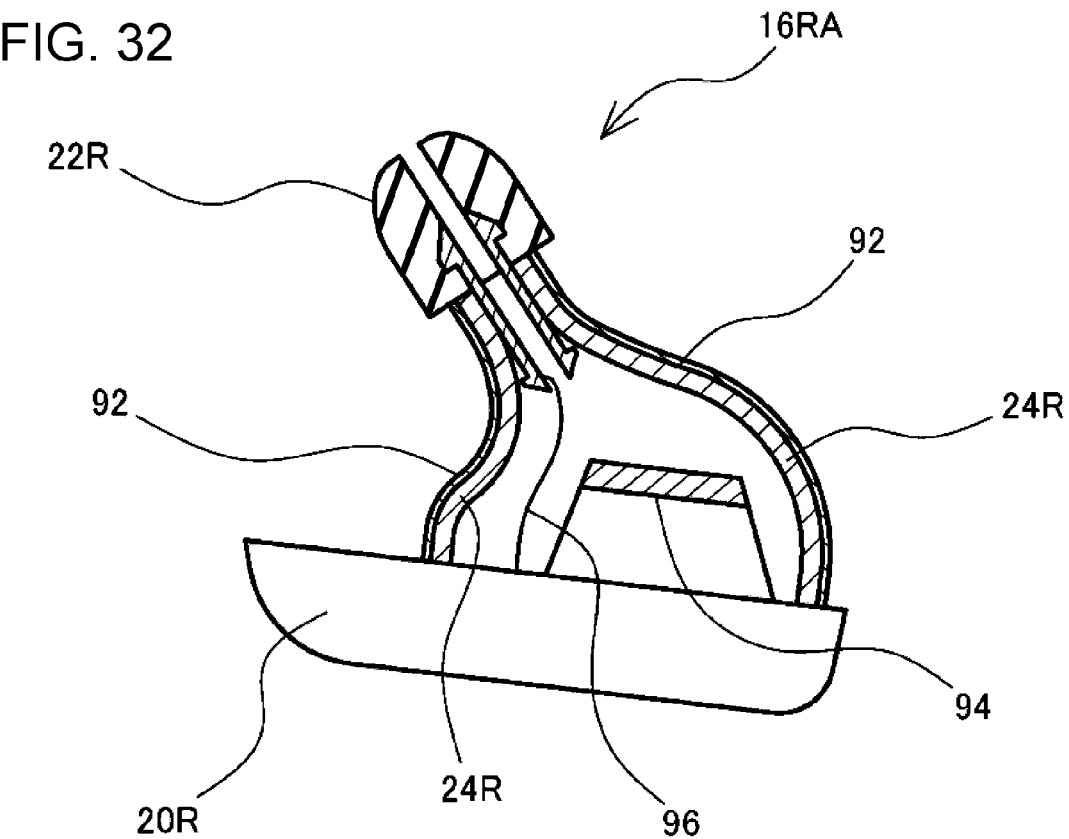
FIG. 32 is a sectional view illustrating another example of the right-side earphone.

Another example of the earphone will be described below with reference to FIG. 32. FIG. 32 is a sectional view of a right-side earphone 16RA, which is an alternative to the right-side earphone 16R.

As in the right-side earphone 16R, the right-side earphone 16RA includes the right-side housing 20R, the right-side earpiece 22R, and the right-side support 24R. The right-side ear hanger 26R may be provided or may not be provided in the right-side earphone 16RA.

An electrode film 92, which is a conductive film, is formed on the outer surface (that is, the surface facing the right ear) of the right-side support 24R. The electrode film 92 is formed by coating the outer surface of the right-side support 24R with a conductive paste. Instead of forming the electrode film 92, the right-side support 24R may be made of conductive rubber.

As in the right-side earphone 16R, the right-side earpiece 22R is made of conductive rubber. Alternatively, a conductive film may be formed on the outer surface of the right-side earpiece 22R.

The right-side support 24R is a hollow member and is provided on the right-side housing 20R. A speaker 94 is disposed in the space of the right-side support 24R and is fixed on the right-side housing 20R.

One end of an electrical wire 96 is connected to the electrode provided in the right-side earpiece 22R, and the other end thereof is connected to the substrate stored in the right-side housing 20R. The electrical wire 96 is laid in the right-side support 24R. If the right-side earpiece 22R itself is made of conductive rubber, one end of the electrical wire 96 is connected to part of the right-side earpiece 22R. If an electrode made of a conductive film, for example, is formed on the right-side earpiece 22R, one end of the electrical wire 96 is connected to this electrode.

The left-side earphone is configured similarly to the right-side earphone 16RA.

The electrode of the right-side earpiece 22R is used as a sensor electrode or a reference electrode, and the electrode film 92 is used as a ground electrode, for example. If the electrode of the right-side earpiece 22R is used as a sensor electrode, the electrode of the left-side earpiece 22L is used as a reference electrode. If the electrode of the right-side earpiece 22R is used as a reference electrode, the electrode of the left-side earpiece 22L is used as a sensor electrode.

The speaker 94 is disposed separately from each of the electrodes (the electrode of the right-side earpiece 22R and the electrode film 92). It is thus unlikely that noise caused by the speaker 94 will be mixed with potential signals indicating potentials detected by the electrodes. The use of fewer electrical wires also contributes to achieving high reliability.

The right-side earphone and the left-side earphone may be formed in a flexible structure. For example, the right-side earphone and the left-side earphone may be deformable to be adjusted to the shapes of the ears of a user. This will be discussed in detail with reference to FIG. 33.

Figure 33:
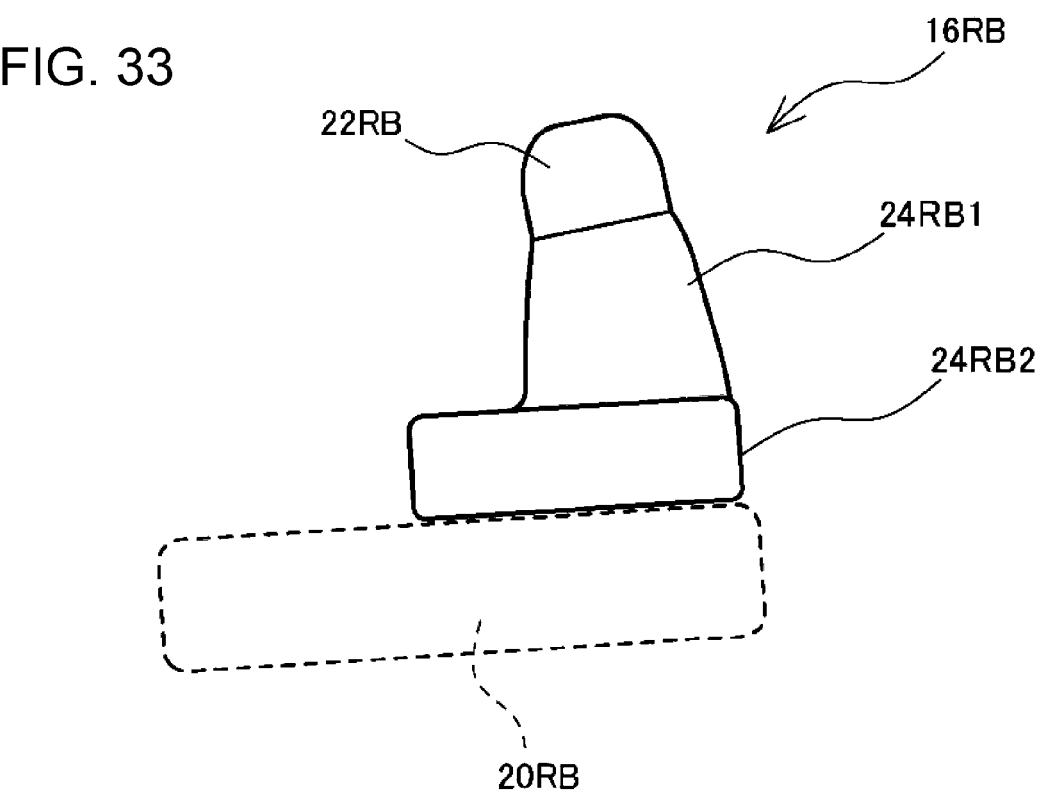
FIG. 33 illustrates the external appearance of a right-side earphone having a flexible structure.

FIG. 33 illustrates the external appearance of a right-side earphone 16RB having a flexible structure.

The right-side earphone 16RB includes a right-side earpiece 22RB, an upper layer member 24RB1, and a lower layer member 24RB2. The upper layer member 24RB1 is connected to the lower layer member 24RB2, and the right-side earpiece 22RB is connected to the upper layer member 24RB1. That is, the upper layer member 24RB1 is interposed between the lower layer member 24RB2 and the right-side earpiece 22RB.

The upper layer member 24RB1 is a hollow member, and a conductive tube member for transmitting sound and electrical wires are disposed within the upper layer member 24BR1.

The right-side earpiece 22RB and the upper layer member 24RB1 are narrower than the lower layer member 24RB2, for example. The right-side earpiece 22RB is inserted into the ear canal and contacts the surface (that is, the skin) of the ear canal. The upper layer member 24RB1 contacts the cavity of concha.

The right-side earpiece 22RB and the upper layer member 24RB1 are made of an elastic member, such as rubber or a sponge. The right-side earpiece 22RB is flexible enough to be deformable to match the shape of the ear canal when being inserted into the ear canal. The upper layer member 24RB1 is flexible enough to be deformable when contacting the cavity of concha.

Each of the right-side earpiece 22RB and the upper layer member 24RB1 may be made of conductive rubber. Alternatively, an electrode made of a conductive film may be formed on the surface of each of the right-side earpiece 22RB and the upper layer member 24RB1. Electrical wires connected to the individual electrodes are disposed within the upper layer member 24RB1.

The lower layer member 24RB2 may be fixed on the right-side housing 20RB. Elements such as substrates are housed in the right-side housing 20RB.

The right-side earpiece 22RB is flexible enough to be deformable to match the shape of the ear canal. This structure makes it possible to easily bring the electrode of the right-side earpiece 22RB into close contact with the surface of the ear canal. The upper layer member 24RB1 is flexible enough to be deformable to match the shape of the cavity of concha. This structure makes it possible to easily bring the electrode of the upper layer member 24RB1 into close contact with the surface of the cavity of concha.

Modified examples of the earphone will be described below.

First Modified Example of Earphone

Figure 34:
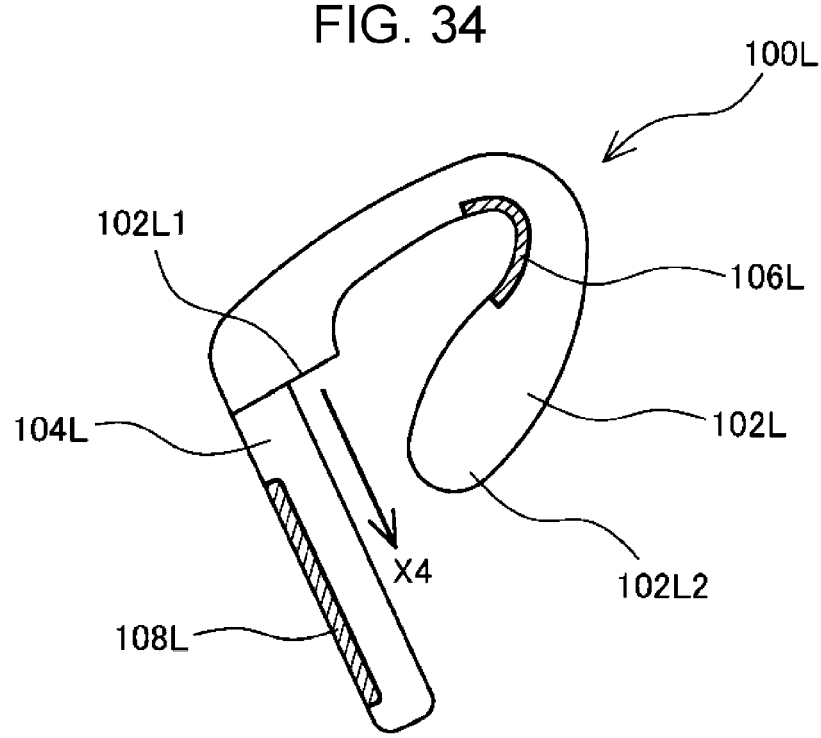
FIG. 34 illustrates the external appearance of a left-side earphone according to a first modified example.
Figure 35:
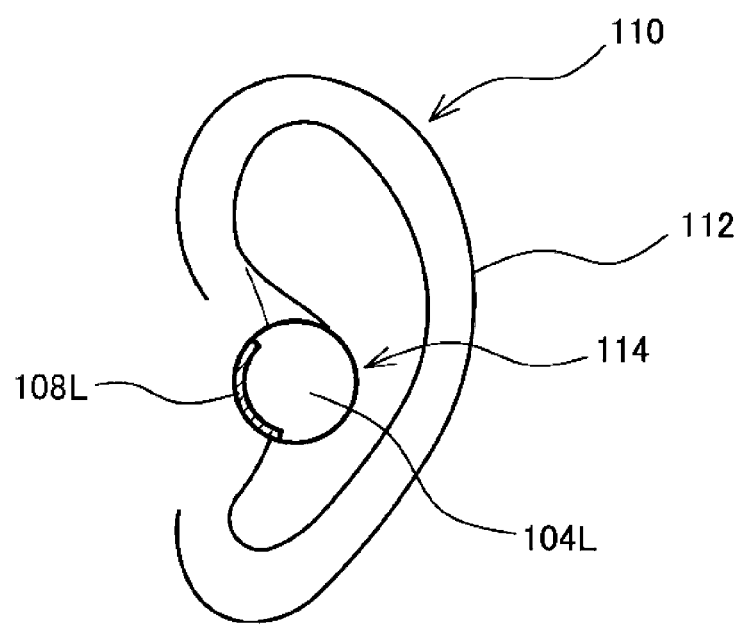
FIG. 35 illustrates the external appearance of a left ear of a human.

A first modified example of the earphone will be described below with reference to FIGS. 34 and 35. FIG. 34 illustrates the external appearance of a left-side earphone 100L according to the first modified example. FIG. 35 illustrates the external appearance of a left ear 110.

As shown in FIG. 34, the left-side earphone 100L includes a left-side ear hanger 102L and a left-side inserting member 104L.

The left-side ear hanger 102L has a curved portion so as to sandwich a helix 112 of the left ear 110. An electrode 106L is disposed on the inner side of the curved portion. For example, the left-side ear hanger 102L is attached to the portion of the helix 112 which faces the back side of the head and sandwiches this portion. As a result of the curved portion touching the helix 112, the electrode 106L contacts the surface (that is, the skin) of the helix 112. Instead of providing the electrode 106L, the left-side ear hanger 102L itself may be made of conductive rubber.

The left-side inserting member 104L is formed in a cylindrical or semi-cylindrical shape and is connected to part of a first end 102L1 of the left-side ear hanger 102L. The left-side inserting member 104L is provided to project from the first end 102L1 of the left-side ear hanger 102L so as to extend toward the left ear 110 when the left-side earphone 100L is worn on the left ear 110, that is, when the left-side ear hanger 102L is attached to the helix 112.

An electrode 108L is provided on the side surface of the left-side inserting member 104L. As shown in FIG. 35, the left-side inserting member 104L is inserted into an ear canal 114, and then, the electrode 108L contacts the surface of the ear canal 114. In the example in FIG. 34, the electrode 108L is provided on the side surface of the left-side inserting member 104L which is opposite the surface facing the left-side ear hanger 102L. With this configuration, when the left-side earphone 100L is worn on the left ear 110, the electrode 108L contacts the front portion of the ear canal 114. The electrode 108L may be provided at another portion of the side surface of the left-side inserting member 104L or be provided on the entire side surface. Instead of providing the electrode 108L, the left-side inserting member 104L itself may be made of conductive rubber.

As indicated by the arrow X4 in FIG. 34, sound emitted from a speaker disposed in the left-side earphone 100L is output from the portion of the first end 102L1 which is not connected to the left-side inserting member 104L.

When the left-side ear hanger 102L is attached to the helix 112, a second end 102L2 of the left-side ear hanger 102L is positioned between the left ear 110 and the side face of the head (that is, at the base of the left ear 110).

The left-side ear hanger 102L and the left-side inserting member 104L may be formed in a flexible structure. For example, the left-side ear hanger 102L may be flexible enough to be deformable to match the shape of the helix 112. The left-side inserting member 104L may be flexible enough to be deformable to match the shape of the ear canal 114.

The right-side earphone is configured similarly to the left-side earphone 100L. That is, the right-side earphone includes a right-side ear hanger with an electrode and a right-side inserting member with an electrode.

The electrode 106L provided on the left-side hanger 102L is used as a ground electrode, while the electrode 108L provided on the left-side inserting member 104L is used as a sensor electrode or a reference electrode. Likewise, the electrode provided on the right-side hanger is used as a ground electrode, while the electrode provided on the right-side inserting member is used as a sensor electrode or a reference electrode. For example, the electrode 108L is used as a sensor electrode, while the electrode provided on the right-side inserting member is used as a reference electrode, or vice versa.

Figure 36:
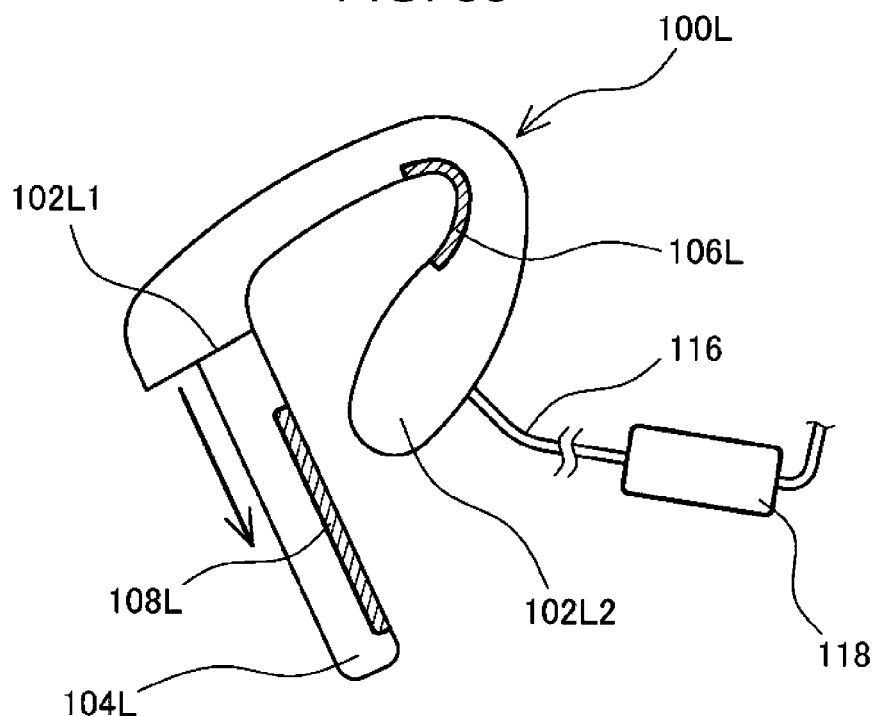
FIG. 36 illustrates the external appearance of a left-side earphone, which is an alternative to the first modified example.
Figure 37:
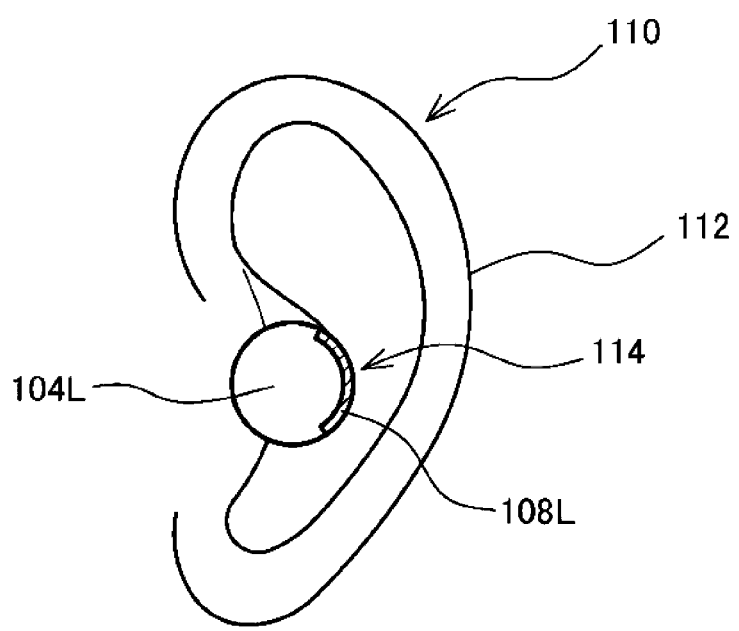
FIG. 37 illustrates the external appearance of a left ear of a human.

Another example of the left-side earphone 100L is shown in FIGS. 36 and 37. FIG. 36 illustrates the external appearance of another example of the left-side earphone 100L. FIG. 37 illustrates the external appearance of the left ear 110.

In the example in FIGS. 36 and 37, the electrode 108L is formed on the side surface of the left-side inserting member 104L which faces the left-side ear hanger 102L. With this configuration, as shown in FIG. 37, when the left-side earphone 100L is worn on the left ear 110, the electrode 108L contacts the back portion of the ear canal 114. The right-side earphone is configured similarly to the left-side earphone 100L shown in FIG. 36.

A cable 116 is shown in FIG. 36. The cable 116 connects the left-side earphone 100L and the right-side earphone with each other. The cable 116 may not be used, in which case, the left-side earphone 100L and the right-side earphone communicate with each other wirelessly. A holder 118 may be provided in the cable 116. In the holder 118, the above-described various substrates housed in the right-side housing 20R and the battery and other elements in the left-side housing 20L may be stored. The substrates and the battery may alternatively be stored in the left-side earphone 100L or the right-side earphone. Various switches and buttons may be provided in the holder 118.

Second Modified Example of Earphone

Figure 38:
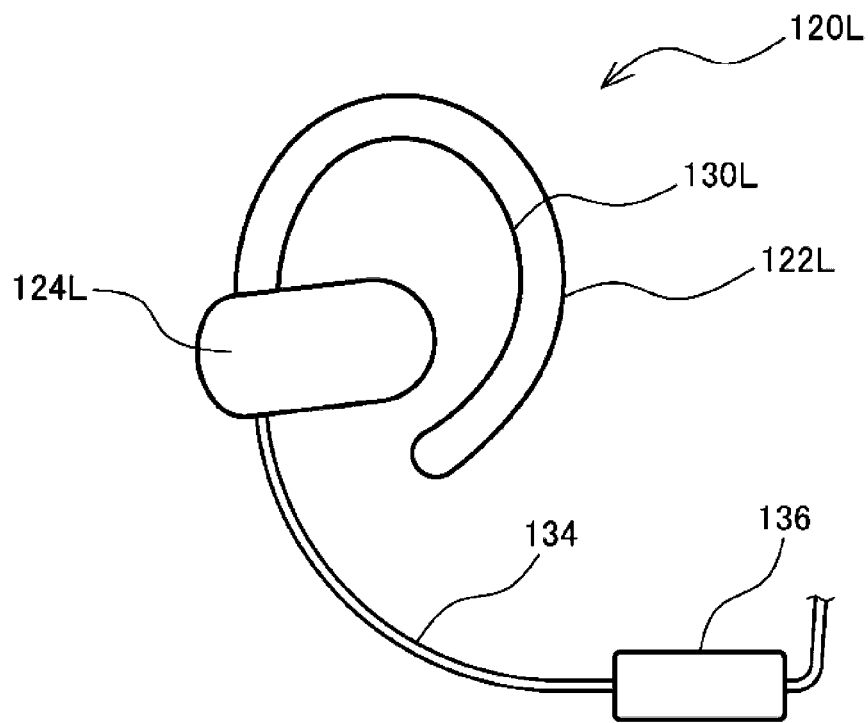
FIG. 38 illustrates a left-side earphone according to a second modified example as viewed from the left side.
Figure 39:
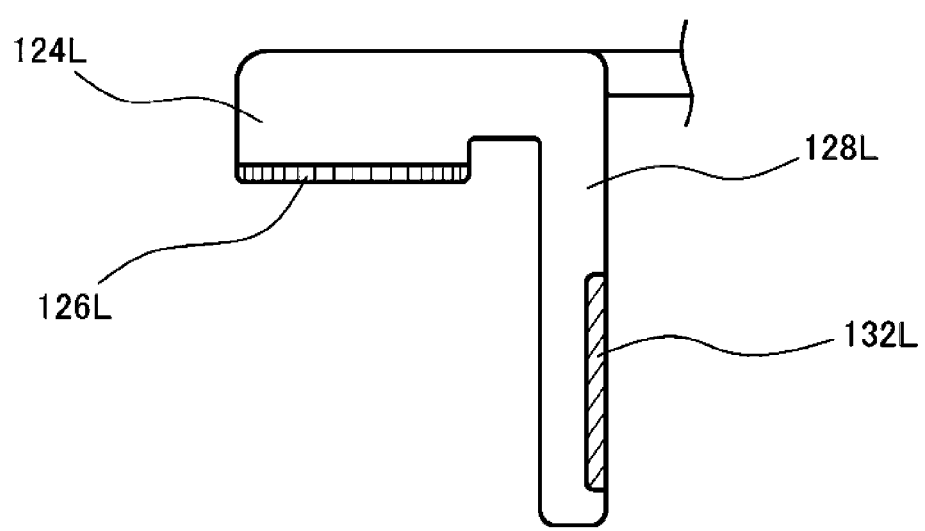
FIG. 39 illustrates the left-side earphone according to the second modified example as viewed from above.
Figure 40:
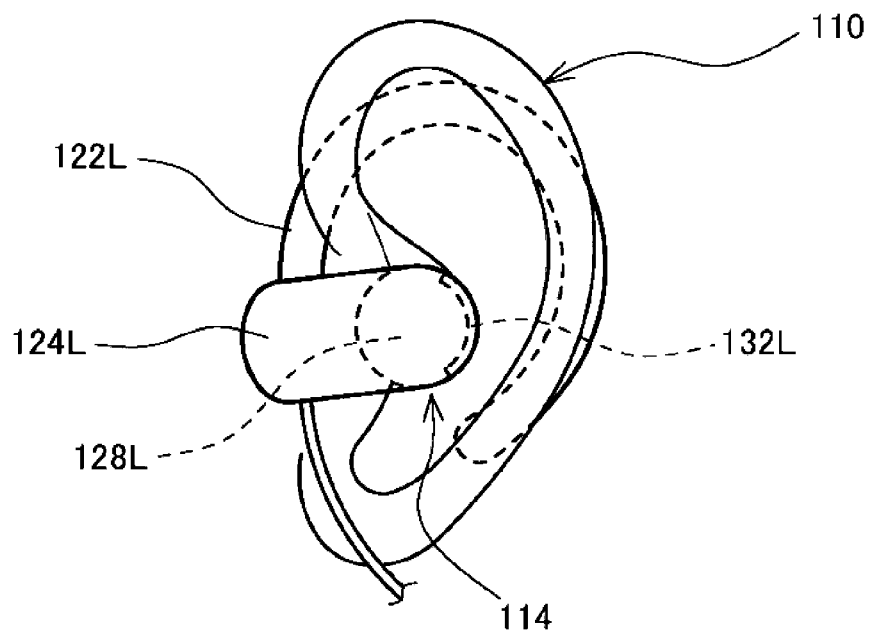
FIG. 40 illustrates the external appearance of a left ear of a human.

A second modified example of the earphone will be described below with reference to FIGS. 38 through 40. FIG. 38 illustrates a left-side earphone 120L according to the second modified example as viewed from the left side. FIG. 39 illustrates the left-side earphone 120L as viewed from above. FIG. 40 illustrates the external appearance of the left ear 110. The left-side earphone 120L of the second modified example is a bone-conduction earphone which transmits sound via bone conduction.

The left-side earphone 120L includes a left-side hanger 122L, a left-side support 124L, a left-side bone conducting portion 126L, and a left-side inserting member 128L. In FIG. 39, the left-side hanger 122L is not shown for the sake of representation.

The left-side ear hanger 122L is generally formed in a curved shape so as to be hung on the left ear 110. The left-side ear hanger 122L is placed between the helix of the left ear 110 and the side face of the head (that is, at the base of the left ear 110) and is sandwiched therebetween. An electrode 130L is provided on the inner side of the curved portion. As a result of the curved portion being placed between the helix and the side face of the head, the electrode 130L contacts the base of the left ear 110. Instead of providing the electrode 130L, the left-side ear hanger 122L itself may be made of conductive rubber.

One end of the left-side hanger 122L is fixed to the left-side support 124L. The left-side hanger 122L is curved backward from the portion fixed to the left-side support 124L so as to match the shape of the base of the left ear 110, for example.

The left-side bone conducting portion 126L is provided on part of the surface of the left-side support 124L which faces the left ear 110 when the left-side earphone 120L is worn on the left ear 110. The left-side inserting member 128L is provided to project from the surface of the left-side support 124L toward the left ear 110. As a result of the left-side bone conducting portion 126L vibrating, sound is transmitted to the inner ear via bones (the skull, for example). An electrode 132L is disposed on the side surface of the left-side inserting member 128L. When the left-side earphone 120L is worn on the left ear 110, the left-side bone conducting portion 126L contacts part of the left ear 110. The left-side inserting member 128L is inserted into the ear canal 114, as shown in FIG. 40, and then, the electrode 132L contacts the surface of the ear canal 114. In the example in FIGS. 39 and 40, the electrode 132L is provided on the side surface of the left-side inserting member 128L which faces the back side of a user. With this arrangement, when the left-side earphone 120L is worn on the left ear 110, the electrode 132L touches the back portion of the ear canal 114. The electrode 132L may be provided at another portion of the side surface of the left-side inserting member 128L or be provided on the entire side surface. Instead of providing the electrode 132L, the left-side inserting member 128L itself may be made of conductive rubber.

When the left-side ear hanger 122L is worn on the base of the left ear 110 and the left-side inserting member 128L is inserted into the ear canal 114, the left-side inserting member 128L and the left-side ear hanger 122L can sandwich the base of the left ear 110. In this manner, the left-side earphone 120L can be prevented from being displaced from a correct position.

The right-side earphone is configured similarly to the left-side earphone 120L. That is, the right-side earphone includes a right-side ear hanger with an electrode and a right-side inserting member with an electrode.

The electrode 130L provided on the left-side hanger 122L is used as a ground electrode, while the electrode 132L provided on the left-side inserting member 128L is used as a sensor electrode or a reference electrode. Likewise, the electrode provided on the right-side hanger is used as a ground electrode, while the electrode provided on the right-side inserting member is used as a sensor electrode or a reference electrode. For example, the electrode 132L is used as a sensor electrode, while the electrode provided on the right-side inserting member is used as a reference electrode, or vice versa.

A cable 134 is shown in FIG. 38. The cable 134 connects the left-side earphone 120L and the right-side earphone with each other. The cable 134 may not be used, in which case, the left-side earphone 120L and the right-side earphone communicate with each other wirelessly. A holder 136 may be provided in the cable 134. In the holder 136, the above-described various substrates housed in the right-side housing 20R and the battery and other elements in the left-side housing 20L may be stored. The substrates and the battery may alternatively be stored in the left-side earphone 120L or the right-side earphone. Various switches and buttons may be provided in the holder 136.

Third Modified Example of Earphone

Figure 41:
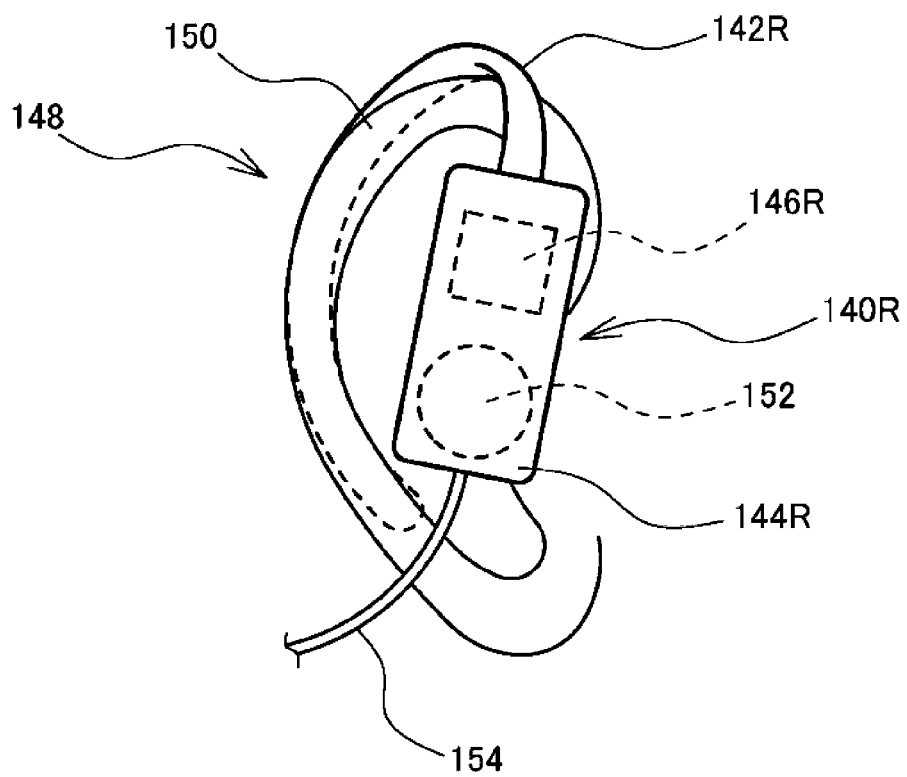
FIG. 41 illustrates a right-side earphone according to a third modified example as viewed from the right side.

A third modified example of the earphone will be described below with reference to FIG. 41. FIG. 41 illustrates a right-side earphone 140R according to the third modified example as viewed from the right side. The right-side earphone 140R of the third modified example is a cartilage-conduction earphone which transmits sound via cartilage conduction.

The right-side earphone 140R includes a right-side hanger 142R, a right-side support 144R, and a cartilage conducting portion 146R.

The right-side ear hanger 142R is generally formed in a curved shape so as to be hung on a right ear 148. More specifically, the right-side ear hanger 142R is hung on the top portion of a helix 150 of the right ear 148. An electrode is provided on the inner side of the curved portion. When the curved portion is hung on the helix 150, the electrode provided on the curved portion contacts the helix 150. Instead of providing the electrode, the right-side ear hanger 142R itself may be made of conductive rubber.

One end of the right-side hanger 142R is fixed to the right-side support 144R. The right-side support 144R is disposed to contact the cavity of concha when the right-side earphone 140R is worn on the right ear 148. The cartilage conducting portion 146R is provided at a portion of the right-side support 144R which contacts the cavity of concha. As a result of the cartilage conducting portion 146R vibrating, the cartilage in the ear canal also vibrates so as to transmit sound to the inner ear.

An electrode may be provided on the surface of the right-side support 144R which contacts the surface of the cavity of concha of the right ear 148. When the right-side earphone 140R is worn on the right ear 148, the right-side support 144R contacts the cavity of concha, and more specifically, the electrode provided on the right-side support 144R contacts the cavity of concha.

In another example, a right-side inserting member which is inserted into the canal of the right ear 148 may be provided at the surface of the right-side support 144R. An electrode may be disposed on the side surface of the right-side inserting member. When the right-side earphone 140R is worn on the right ear 148 and the right-side inserting member is inserted into the ear canal, the electrode provided on the right-side inserting member contacts the ear canal. The right-side inserting member may be an earpiece or a structure having a semi-cylindrical shape.

The left-side earphone is configured similarly to the right-side earphone 140R. That is, the left-side earphone includes a left-side ear hanger with an electrode and a left-side support with an electrode. A left-side inserting member with an electrode may be provided on the left-side support. In this case, the provision of the electrode on the left-side support may be omitted.

The electrode provided on the right-side hanger 142R is used as a ground electrode, while the electrode provided on the right-side support 144R or the right-side inserting member is used as a sensor electrode or a reference electrode. Likewise, the electrode provided on the left-side hanger is used as a ground electrode, while the electrode provided on the left-side support or the left-side inserting member is used as a sensor electrode or a reference electrode. For example, the electrode provided on the right-side support 144R or the right-side inserting member is used as a sensor electrode, while the electrode provided on the left-side support or the left-side inserting member is used as a reference electrode, or vice versa.

A cable 154 is shown in FIG. 41. The cable 154 connects the right-side earphone 140R and the left-side earphone with each other. The cable 154 may not be used, in which case, the right-side earphone 140R and the left-side earphone communicate with each other wirelessly. A holder may be provided in the cable 154. In the holder, the above-described various substrates housed in the right-side housing 20R and the battery and other elements in the left-side housing 20L may be stored. The substrates and the battery may alternatively be stored in the right-side earphone 140R or the left-side earphone. Various switches and buttons may be provided in the holder.

Modified examples of an electrode used as a sensor electrode, a reference electrode, or a ground electrode will be described below.

First Modified Example of Electrode

An electrode according to a first modified example will be described below in detail with reference to FIGS. 42A through 45. The electrode according to the first modified example is a conductive microneedle electrode.

Figure 42A:
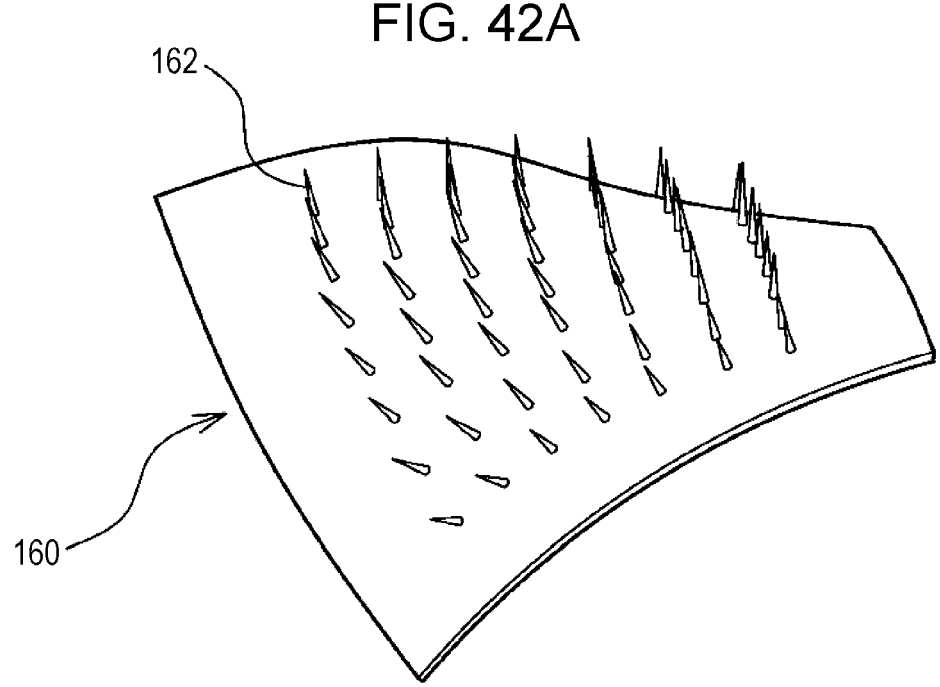
FIG. 42A is a perspective view illustrating a microneedle sheet.
Figure 42B:
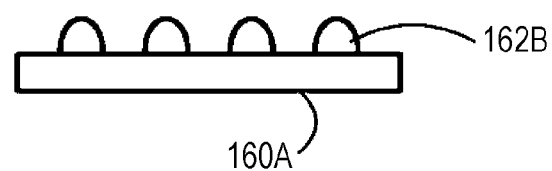
FIG. 42B is a side view schematically illustrating a microneedle sheet.
Figure 42C:
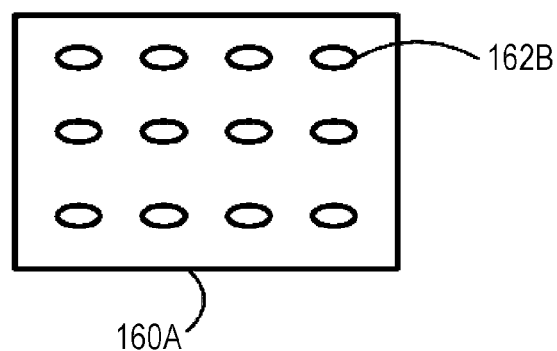
FIG. 42C is a schematic view illustrating a microneedle sheet as viewed from above.
Figure 43:
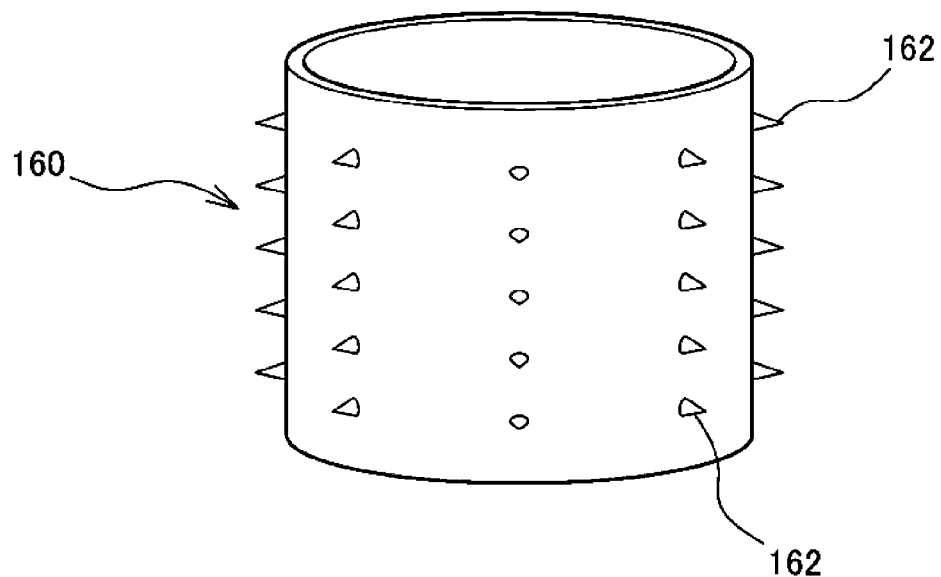
FIG. 43 is a perspective view illustrating a microneedle sheet.

FIGS. 42A and 43 are perspective views illustrating a microneedle sheet 160. FIG. 42B is a side view schematically illustrating a microneedle sheet 160A. FIG. 42C is a schematic view illustrating the microneedle sheet 160A as viewed from above. The microneedle sheet 160 is a sheet formed in a rectangle, for example. On one surface of the microneedle sheet 160, multiple microneedles 162 constituted by conductive members are provided. Microneedles are needle-like members having a diameter or a length of 1 mm or smaller. Members similar to microneedles but having a size larger than 1 mm will be called projections in the exemplary embodiment. The microneedle sheet 160A shown in FIGS. 42B and 42C have projections 162B. The forward end of each projection 162B is not pointed but is curved. The microneedles 162 may be made of a metal. However, for safety reasons, such as a breakage of the microneedles 162, and for health reasons, such as allergic reactions, a material having a high biocompatibility, such as a biodegradable biopolymer having conductivity, is suitably used for the microneedles 162. As the material for the projections 162B, a conductive, elastic material may suitably be used.

As shown in FIG. 43, the microneedle sheet 160 is rolled up in a cylindrical shape with the surface having the microneedles 162 facing outward.

Figure 44A:
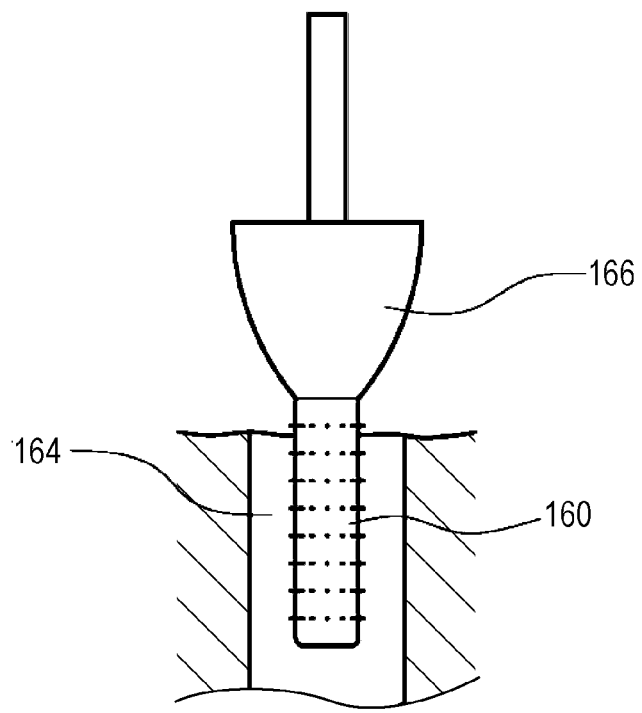
FIG. 44A is a sectional view schematically illustrating an ear canal.
Figure 44B:
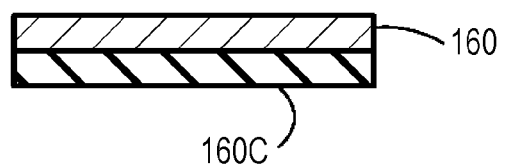
FIG. 44B is a sectional view of a microneedle sheet and an elastic base layer.
Figure 45:
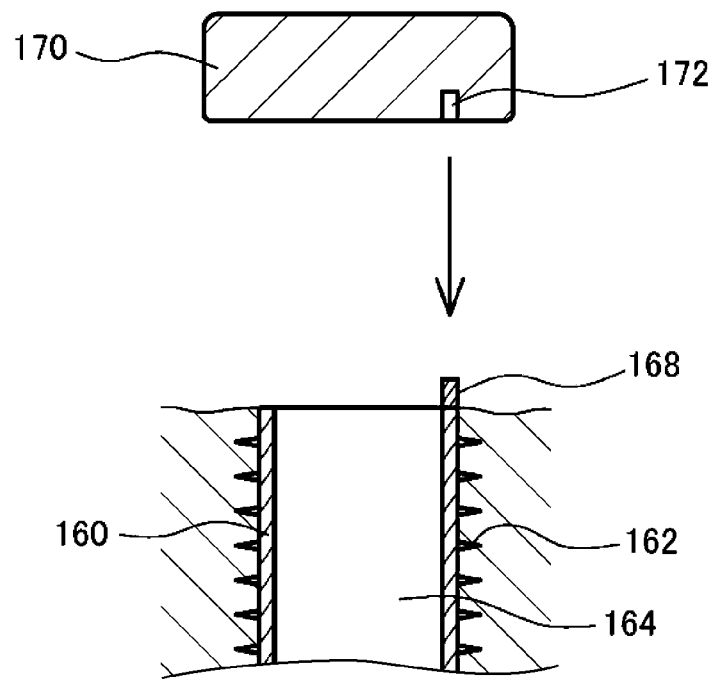
FIG. 45 is a sectional view schematically illustrating an ear canal.

FIGS. 44A and 45 are sectional views schematically illustrating an ear canal 164. As shown in FIG. 44A, the microneedle sheet 160 rolled up in a cylindrical shape is attached to the forward end of a support 166 and is inserted into and placed in the ear canal 164. For example, the microneedle sheet 160 is rolled up to a size small enough to be inserted into the ear canal 164. It is appropriate that the microneedle sheet 160 be highly elastic and be flexibly deformed. To enhance the flexible deformation and the adhesiveness with the ear canal 164, as shown in FIG. 44B, the microneedle sheet 160 may be bonded onto an elastic base layer 160C made of rubber, for example. FIG. 44B is a sectional view of the microneedle sheet 160 and the elastic base layer 160C. The microneedle sheet 160 has a high elasticity and is flexibly deformed to follow various shapes of the ear canals of users, thereby enabling the microneedles 162 serving as an electrode to reliably contact the skin of the ear canal while enhancing the adhesiveness with the ear canal. Even with a motion of a user or a slight change in the shape of the ear canal caused by such a motion, the electrode is reliably brought into contact with the skin of the ear canal, thereby obtaining a stable electrical contact. The microneedle sheet 160 may be formed to be attachable to and detachable from the elastic base layer 160C and be replaceable as consumables, thereby achieving a cost reduction. To facilitate the replaceability of microneedle sheets, instead of bonding the microneedle sheet 160 to the elastic base layer 160C by the attraction of molecules on the surfaces of the two members due to physical and/or chemical force, non-adhesiveness characteristics may be utilized to easily detach the microneedle sheet 160 from the elastic base layer 160C to prevent or eliminate the adhesiveness therebetween.

After the microneedle sheet 160 is inserted into and placed in the ear canal 164, it is separated from the support 166 by cutting off the microneedle sheet 160, for example. Then, the microneedle sheet 160 is spread in the ear canal 164 so as to contact the surface (that is, the skin) of the ear canal 164. As shown in FIG. 45, the multiple microneedles 162 disposed on the surface of the microneedle sheet 160 contact and stick into the surface of the ear canal 164. In this manner, the conductive microneedles 162 are placed in contact with the ear canal 164. Unlike the microneedles 162, the projections 162B shown in FIGS. 42B and 42C do not stick into the skin, but they are deformed to contact the skin, thereby raising the contact pressure of the projections 162B onto the ear canal 164.

As shown in FIG. 45, a connector 168 constituted by a conductive member protrudes from one side of the microneedle sheet 160 (the portion fixed to the support 166, for example). An electrical wire is formed on the microneedle sheet 160 and connects the individual microneedles 162 with each other. The electrical wire is also connected to the connector 168. Hence, a potential signal indicating potentials detected by the conductive microneedles 162 can be output to the outside of the microneedle sheet 160 via the electrical wire and the connector 168.

For example, a device body 170 is worn on the ear, as shown in FIG. 45. A connector receiver 172 is provided in the device body 170 to receive the connector 168. When the device body 170 is worn on the ear, the connector 168 is fit into the connector receiver 172. Then, a potential signal indicating potentials detected by the microneedles 162 is output to the device body 170.

The microneedles 162 are used as a sensor electrode, a reference electrode, or a ground electrode.

Second Modified Example of Electrode

Figure 46:
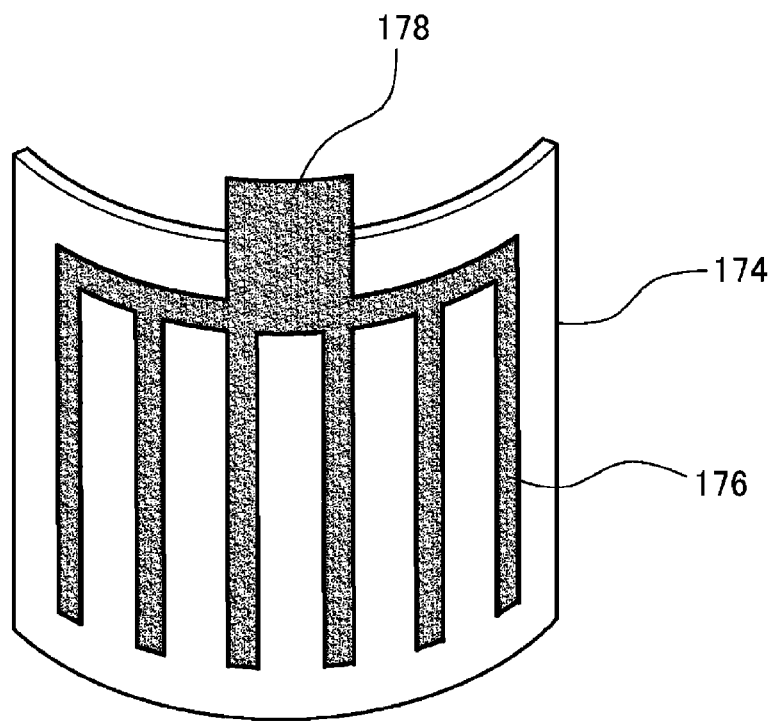
FIG. 46 is a perspective view of an induced pluripotent stem (iPS) cell sheet.

A second modified example of the electrode will be described below with reference to FIG. 46. In the second modified example, an induced pluripotent stem (iPS) cell sheet is used instead of the microneedle sheet 160. FIG. 46 is a perspective view illustrating an example of an iPS cell sheet 174. The iPS cell sheet 174 is formed in a rectangle, for example, and an electrode 176 is formed on the surface of the iPS cell sheet 174. A connector 178 connected to the electrode 176 is provided on the iPS cell sheet 174. As in the microneedle sheet 160, the iPS cell sheet 174 is rolled up in a cylindrical shape and is inserted into and placed in the ear canal 164. The electrode 176 is thus brought into contact with the surface (that is, the skin) of the ear canal 164. A potential signal indicating potentials detected by the electrode 176 is output to the device body 170 via the connector 178. Instead of an iPS cell sheet, an electronic skin (also called an e-skin or a bionic skin) sheet may be employed. An electronic skin sheet is bonded to an elastic base layer made of rubber, for example. An electronic skin is flexibly deformed and reliably contacts the skin of the ear canal, thereby obtaining a stable electrical contact. For the electronic skin, a high polymer material having softness and elasticity equivalent to cells may suitably be used. For example, an electronic skin can be formed by constructing or printing an electronic circuit on a high polymer film substrate made of polyester or polyethylene terephthalate.

[Materials and Types of Electrodes]

Materials and types of electrodes for monitoring biological information (such as a sensor electrode, a reference electrode, and a ground electrode) will be discussed below.

Examples of the materials for the electrodes are gold (Au), platinum (Pt), silver (Ag), tungsten (W), molybdenum (Mo), copper (Cu), stainless steel (SUS304), solder, iron (Fe), and silver-silver chloride (Ag/AgCl). The electrode to be used may be changed in accordance with the type of biological information to be monitored.

Examples of the types of electrodes are: disposable surface electrodes using a conductive gel; dry electrodes, such as silver-silver chloride electrodes (Ag/AgCl electrodes), stainless steel electrodes, conductive rubber electrodes, and conductive high-polymer electrodes; non-contact electrodes; silver dish electrodes; suction electrodes; and clip electrodes. Other types of electrodes may be used.

Disposable surface electrodes do not need a paste and are easy to handle. Disposable surface electrodes also have a low impedance and a low offset voltage, thereby making monitoring stable.

Silver-silver chloride electrodes have a low floating potential and a low polarization voltage and can thus be stably utilized. The impedance of silver-silver chloride electrodes is up to several hundreds of kiloohms.

Stainless steel electrodes have a higher offset voltage than silver-silver chloride electrodes.

The impedance of conductive rubber electrodes and that of conductive high-polymer electrodes are several hundreds of kiloohms to several megaohms. Non-contact electrodes are used for monitoring an electrocardiographic signal and a myoelectric signal, for example.

[Charging Methods in Biological Information Monitoring Apparatus 12]

Charging methods for a battery provided in the biological information monitoring apparatus 12 will be described below.

Figure 47:
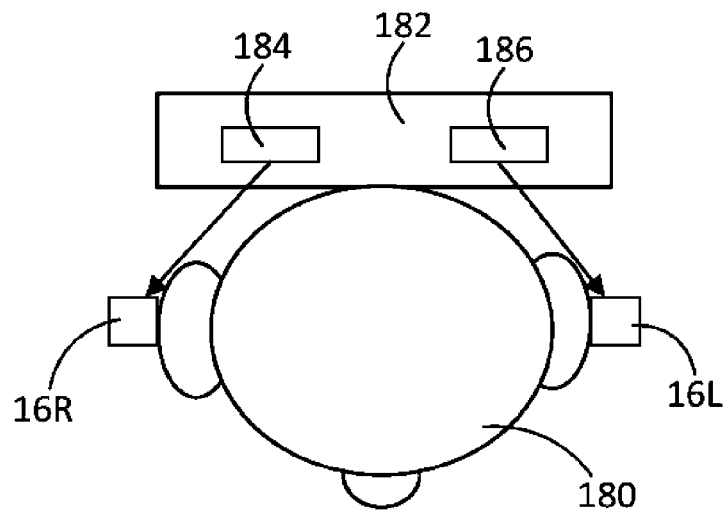
FIGS. 47, 48, and 49 illustrate the head of a human and a cushion as viewed from above.

FIG. 47 illustrates a head 180 of a user and a cushion 182 as viewed from above. An example of the charging method will be discussed below with reference to FIG. 47. Chargers 184 and 186 are disposed in the cushion 182. The chargers 184 and 186 are wireless chargers including elements such as a power transmission coil so as to charge a battery in a non-contact manner. That is, the chargers 184 and 186 charge a battery by utilizing non-contact power transmission. The chargers 184 and 186 are disposed separately from each other in the cushion 182. For example, the charger 184 is disposed closer to one end of the cushion 182 than the center thereof, while the charger 186 is disposed closer to the other end of the cushion 182 than the center thereof. The charger 184 charges a battery located within the wireless coverage area of the charger 184. The charger 186 charges a battery located within the wireless coverage area of the charger 186.

The right-side earphone 16R is worn on the right ear of the user, while the left-side earphone 16L is worn on the left ear of the user. Then, the head 180 is placed on the cushion 182. The charger 184 is disposed at a position at which it can wirelessly charge a battery provided in one of the right-side earphone 16R and the left-side earphone 16L when the head 180 is placed on the cushion 182. Likewise, the charger 186 is disposed at a position at which it can wirelessly charge a battery provided in one of the right-side earphone 16R and the left-side earphone 16L when the head 180 is placed on the cushion 182.

In the example in FIG. 47, the right-side earphone 16R is located within the wireless coverage area of the charger 184. The charger 184 can thus wirelessly charge a battery provided in the right-side earphone 16R.

In the example in FIG. 47, the left-side earphone 16L is located within the wireless coverage area of the charger 186. The charger 186 can thus wirelessly charge a battery provided in the left-side earphone 16L.

Batteries provided in the right-side earphone 16R and the left-side earphone 16L each include elements such as a power receiving coil and can wirelessly be charged.

The charger 184 may start charging a battery when this battery is disposed within the wireless coverage area of the charger 184. Similarly, the charger 186 may start charging a battery when this battery is disposed within the wireless coverage area of the charger 186.

The charging timing and period may be controlled. For example, a control device may be disposed in the right-side earphone 16R or the left-side earphone 16L and may control the charging timing and period. The control device is implemented by an electronic circuit disposed on the main substrate or the sub-substrate, for example. Alternatively, the control device may be disposed in the cushion 182 and may control the charging timing and period.

For example, the control device may cause the chargers 184 and 186 to charge batteries when a user is asleep. The control device judges whether the user is asleep based on biological information, such as brain waves, monitored by the right-side earphone 16R and the left-side earphone 16L.

The control device may cause the charger 184 or 186 to charge a battery while biological information is being monitored. For example, a monitoring chip, such as a brain wave sensor, for monitoring biological information is provided only in the right-side earphone 16R, while a battery is disposed only in the left-side earphone 16L. In this manner, the battery and the monitoring chip are separately disposed in the different earphones. This enables the monitoring chip to monitor biological information without being influenced by wireless charging performed by the charger 184 or 186.

The control device may cause the chargers 184 and 186 to charge batteries while a potential signal and biological information are not being sent. For example, a detected potential signal and biological information are sent from the right-side earphone 16R to the terminal apparatus 14. The control device does not cause the chargers 184 and 186 to charge batteries during the transmission of a detected potential signal and biological information. This makes it possible to send a potential signal and biological information without being influenced by wireless charging.

In the example in FIG. 47, three or more chargers may be disposed in the cushion 182.

Figure 48:
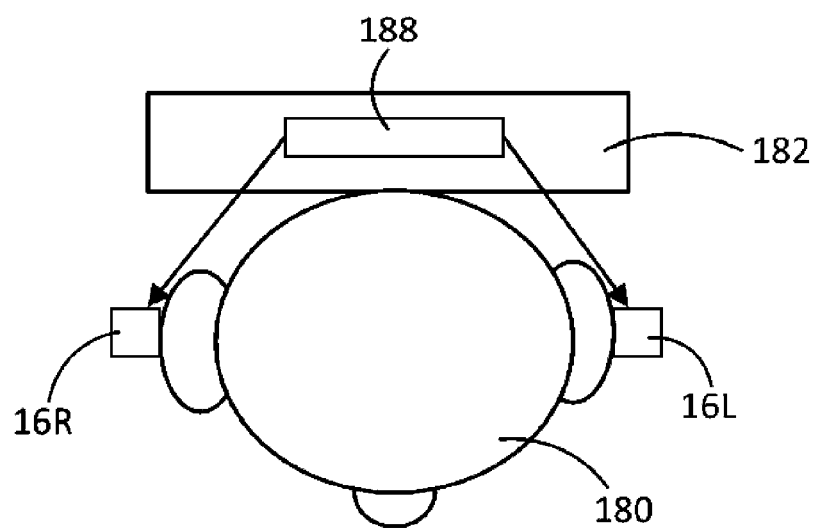

Another example of the charging method is shown in FIG. 48. FIG. 48 illustrates the head 180 of a user and the cushion 182 as viewed from above. One charger 188 is disposed in the cushion 182. The charger 188 is disposed at or near the center of the cushion 182. If a battery is disposed in each of the right-side earphone 16R and the left-side earphone 16L, the charger 188 charges these batteries. The charger 188 may be formed in a size large enough to wirelessly charge batteries disposed in the right-side earphone 16R and the left-side earphone 16L, which are separated from each other, or may have a function of outputting magnetic fields or electric fields having an output level to wirelessly charge these batteries. Multiple chargers may be disposed in the cushion 182.

Figure 49:
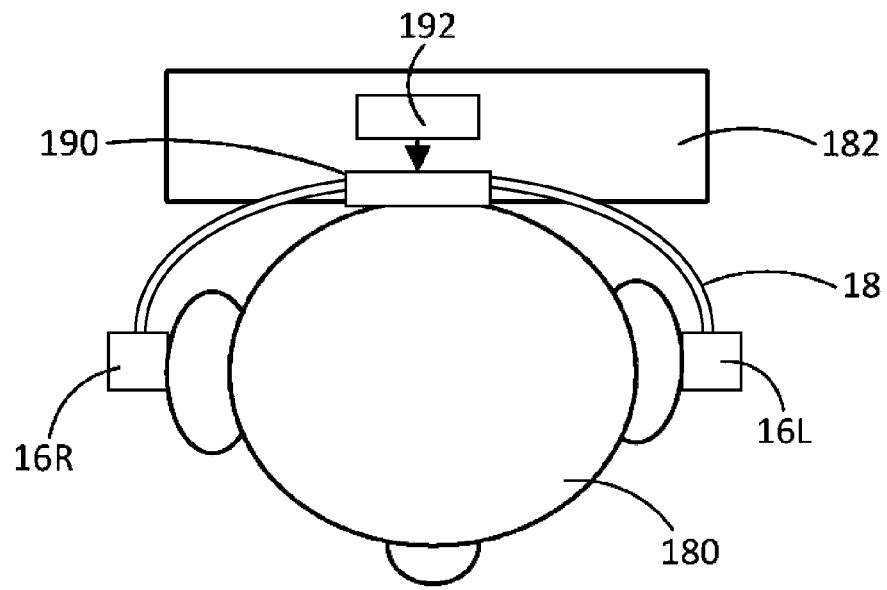

FIG. 49 illustrates still another example of the charging method. FIG. 49 illustrates the head 180 of a user and the cushion 182 as viewed from above. In the example in FIG. 49, a power receiving device 190 including a power receiving coil, for example, is provided at or near the center of the cable 18. One charger 192 is disposed in the cushion 182. The charger 192 is disposed at or near the center of the cushion 182, for example. The power receiving device 190 supplies power received from the charger 192 to batteries provided in the right-side earphone 16R and the left-side earphone 16L so as to charge the batteries.

Figure 50:
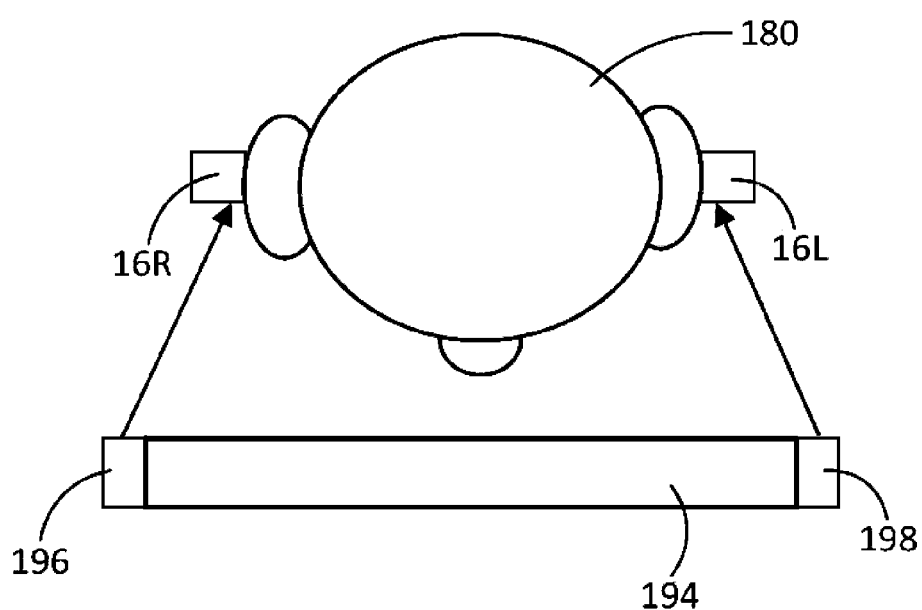
FIGS. 50 and 51 illustrate the head of a human and a display as viewed from above.

FIG. 50 illustrates still another example of the charging method. FIG. 50 illustrates the head 180 of a user and a display 194 as viewed from above. A charger 196 is provided on one of the left and right edges (right edge, for example) of the screen of the display 194, while another charger 198 is provided on the other one of the edges (left edge, for example) of the screen of the display 194.

The charger 196 charges a battery located within the wireless coverage area of the charger 196. The charger 198 charges a battery located within the wireless coverage area of the charger 198.

In the state in which the user is looking at the screen of the display 194, the right-side earphone 16R worn on the right ear is located within the wireless coverage area of the charger 196, while the left-side earphone 16L worn on the left ear is located within the wireless coverage area of the charger 198. The charger 196 can thus wirelessly charge a battery provided in the right-side earphone 16R, while the charger 198 can wirelessly charge a battery provided in the left-side earphone 16L.

The charger 196 may be disposed one edge (right edge, for example) of the top surface of the display 194, while the charger 198 may be disposed on the other edge (left edge, for example) of the top surface of the display 194. Three or more chargers may be provided on the display 194.

In the example in FIG. 50, the above-described control device may be provided and control the charging timing. For example, the control device causes the chargers 196 and 198 to charge batteries when a user is still or is sitting in front of the screen 194 or when the motion of the user is smaller than or equal to a predetermined threshold, and stops the chargers 196 and 198 from charging batteries when the user is in a state other than the above-described states. For example, the control device stops the chargers 196 and 198 from charging batteries when the user is walking or doing some exercises. The motion of the user may be detected by a 6-axis sensor provided in the right-side earphone 16R or by a camera disposed in the display 194. The control device receives a signal indicating the motion of the user detected by the 6-axis sensor or that by the camera so as to detect the motion of the user.

Figure 51:
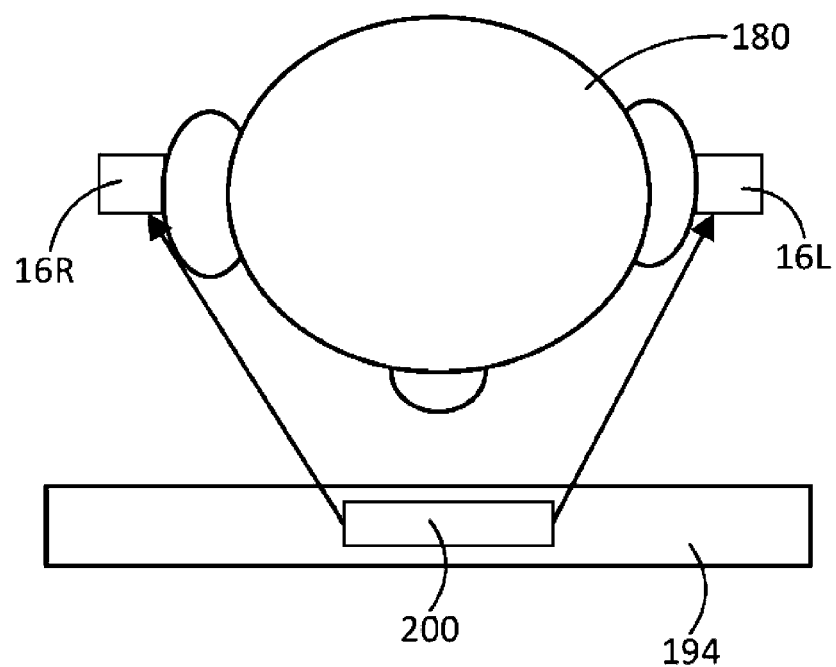

FIG. 51 illustrates still another example of the charging method. FIG. 51 illustrates the head 180 of a user and the display 194 as viewed from above. In the example in FIG. 51, one charger 200 is disposed at or near the center of the top surface of the display 194. If a battery is disposed in each of the right-side earphone 16R and the left-side earphone 16L, the charger 200 charges these batteries. The charger 200 may be formed in a size large enough to wirelessly charge the batteries disposed in the right-side earphone 16R and the left-side earphone 16L, which are separately disposed from each other, or may have a function of outputting magnetic fields or electric fields having an output level to wirelessly charge these batteries. Multiple chargers may be provided on the display 194.

In another example, a wireless charger may be provided on a chair. For example, a charger may be provided at the center or the left and right ends of the headrest of a chair. A charger may be provided at the center or the left and right ends of the top portion of the backrest of a chair. For example, the cushion 182 shown in FIGS. 47 through 49 is replaced by a headrest or a backrest of a chair, and charging methods discussed with reference to FIGS. 47 through 49 are employed.

In another example, a charger is provided in the terminal apparatus 14, and the terminal apparatus 14 may charge a battery.

[Structure of Cable]

Various examples of a cable connecting the right-side earphone 16R and the left-side earphone 16L will be discussed below.

First Example of Cable

Figure 52:
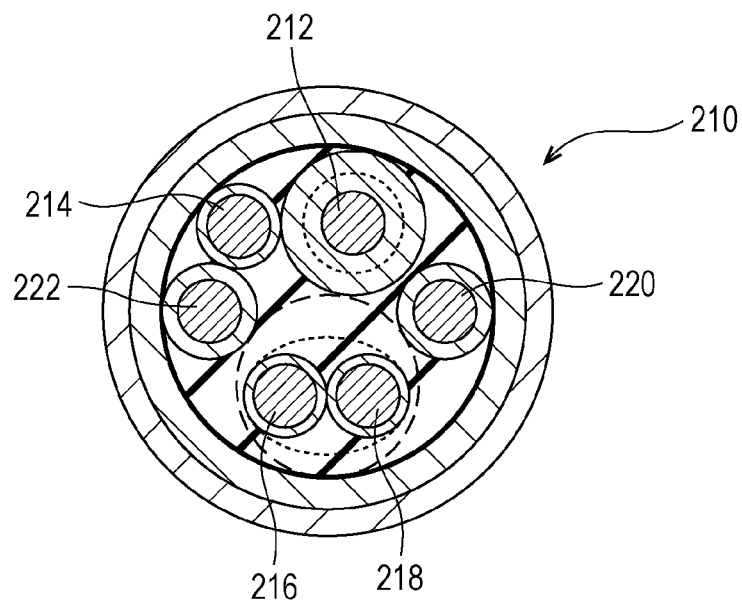
FIG. 52 is a sectional view illustrating a cable of a first example.

FIG. 52 is a sectional view illustrating the configuration of a cable 210 of a first example. The cable 210 includes electrical wires 212 through 222. The electrical wire 212 is a wire for sending and receiving a potential signal indicating potentials detected by a sensor electrode or a reference electrode. Such an electrical wire will also be called a bioelectric potential wire. The electrical wire 214 is a wire for sending and receiving a potential signal indicating potentials detected by a ground electrode. Such a wire will also be called a ground electrode wire. The electrical wires 216 and 218 are wires for sending and receiving an audio signal indicating sound emitted from a speaker. Such a wire will also be called an audio signal wire. The electrical wires 220 and 222 are wires for sending and receiving power supplied from a battery. Such a wire will also be called a battery wire. To reduce noise, the electrical wires 212, 216, and 218 are covered with shield lines.

For example, the electrode provided in the right-side earpiece 22R of the right-side earphone 16R is used as a sensor electrode, the electrode provided in the left-side earpiece 22L of the left-side earphone 16L is used as a reference electrode, and the electrode member 28L of the left-side earphone 16L is used as a ground electrode. The electrode member 28R of the right-side earphone 16R is not used. A monitoring chip, such as a brain wave sensor, for monitoring biological information is provided in the right-side housing 20R of the right-side earphone 16R.

In the above-described arrangement, a potential signal indicating potentials detected by the reference electrode provided in the left-side earphone 16L is sent to the right-side earphone 16R via the electrode wire 212 and is input into the monitoring chip, such as a brain wave sensor. A potential signal indicating potentials detected by the sensor electrode provided in the right-side earphone 16R is input into the monitoring chip in the right-side earphone 16R.

Second Example of Cable

Figure 53:
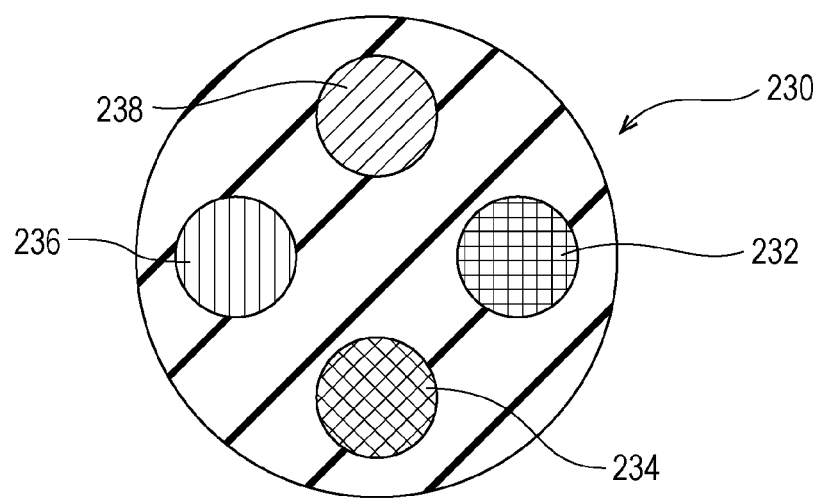
FIG. 53 is a sectional view illustrating a cable of a second example.

FIG. 53 is a sectional view illustrating the configuration of a cable 230 of a second example. The cable 230 includes electrical wires 232, 234, 236, and 238. The electrical wire 232 is a wire for sending and receiving a potential signal indicating potentials detected by a sensor electrode or a reference electrode (bioelectric potential wire). The electrical wire 234 is a wire for sending and receiving a potential signal indicating potentials detected by a ground electrode (ground electrode wire). The electrical wire 236 is a wire for sending and receiving an audio signal (audio signal wire). The electrical wire 238 is a wire for sending and receiving power supplied from a battery (battery wire).

The cable 230 is formed in a circular or elliptical shape in cross section, for example. The electrical wires 232, 234, 236, and 238 are disposed in the cable 230 in the peripheral direction. The bioelectric potential wire 232 is located farthest from the audio signal wire 236 so as to avoid the influence of noise caused by an audio signal. That is, the distance between the bioelectric potential wire 232 and the audio signal wire 236 is longer than that between the other wires.

Third Example of Cable

Figure 54:
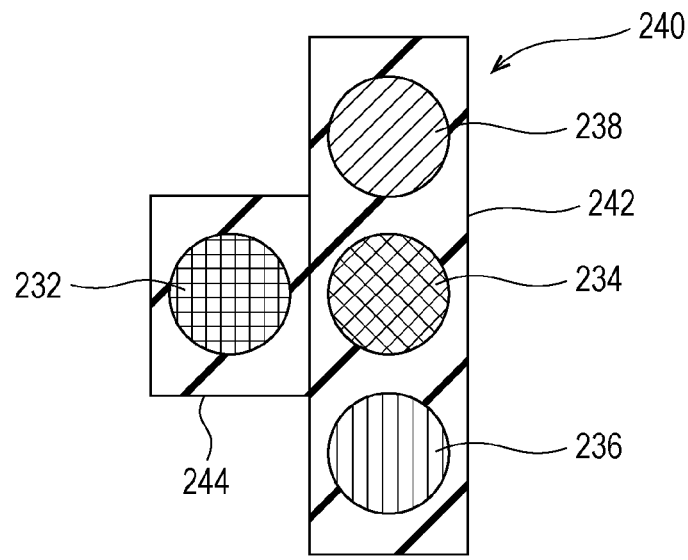
FIG. 54 is a sectional view illustrating a cable of a third example.

FIG. 54 is a sectional view illustrating the configuration of a cable 240 of a third example. The electrical wires 232, 234, 236, and 238 discussed in the second example are disposed in the cable 240.

The cable 240 is constituted by cable elements 242 and 244, for example. The cable elements 242 and 244 are formed in a rectangular shape in cross section.

The electrical wires 236, 234, and 238 are aligned in this order within the cable element 242. The cable element 242 is longer than the cable element 244 in the longitudinal direction, that is, in the direction in which the electrical wires 236, 234, and 238 are aligned. The cable element 244 projects from the cable element 242. The electrical wire 232 is disposed in the cable element 244.

The cable element 244 projects from the portion of the cable element 242 at which the ground electrode wire 234 is located. This makes the distance between the bioelectric potential wire 232 and the audio signal wire 236 longer than that in the configuration in which the audio signal wire 236 would be located at the position of the ground electrode wire 234. It is thus possible to reduce the occurrence of noise in a bioelectric potential caused by an audio signal. Likewise, the distance between the bioelectric potential wire 232 and the battery wire 238 is longer than that in the configuration in which the battery wire 238 would be located at the position of the ground electrode wire 234. It is thus possible to reduce the occurrence of noise in a bioelectric potential caused by power supply from a battery.

The cable 240 may be formed in a triangular shape in cross section. In this case, the electrical wires 232, 234, 236, and 238 may be disposed with the arrangement shown in FIG. 54 in the triangular cross section.

Fourth Example of Cable

Figure 55:
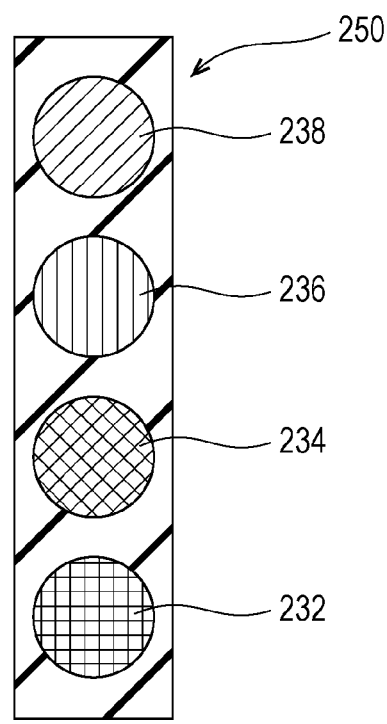
FIG. 55 is a sectional view illustrating a cable of a fourth example.

FIG. 55 is a sectional view illustrating the configuration of a cable 250 of a fourth example. The electrical wires 232, 234, 236, and 238 discussed in the second and third examples are disposed in the cable 250.

The electrical wires 232, 234, 236, and 238 are aligned in this order in the cable 250. The order of the electrical wires 232, 234, 236, and 238 is not restricted to that shown in FIG. 55. The bioelectric potential wire 232 may be disposed separately from the battery wire 238, thereby reducing the occurrence of noise in a bioelectric potential caused by power supply. Likewise, the bioelectric potential wire 232 may be disposed separately from the audio signal wire 236, thereby reducing the occurrence of noise in a bioelectric potential caused by an audio signal.

Fifth Example of Cable

Figure 56:
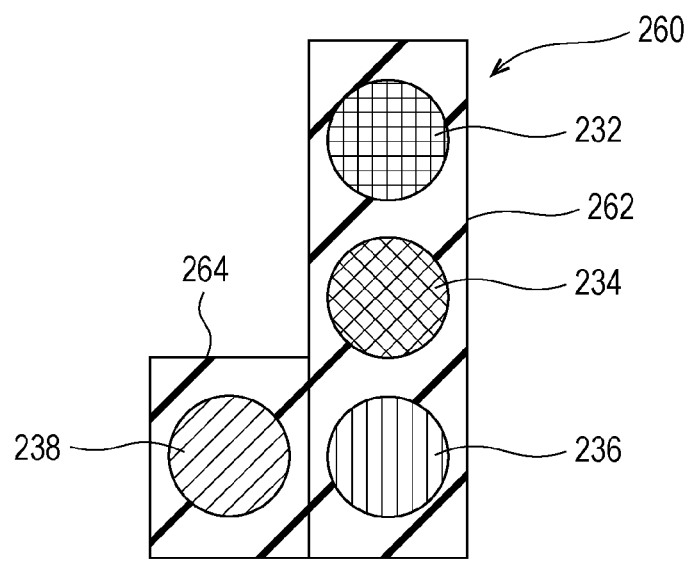
FIG. 56 is a sectional view illustrating a cable of a fifth example.

FIG. 56 is a sectional view illustrating the configuration of a cable 260 of a fifth example. The electrical wires 232, 234, 236, and 238 discussed in the second through fourth examples are disposed in the cable 260.

The cable 260 is constituted by cable elements 262 and 264, for example. The cable elements 262 and 264 are formed in a rectangular shape in cross section.

The electrical wires 232, 234, and 236 are aligned in this order within the cable element 262. The cable element 262 is longer than the cable element 264 in the longitudinal direction, that is, in the direction in which the electrical wires 232, 234, and 236 are aligned. The cable element 264 projects from the cable element 262. The electrical wire 238 is disposed in the cable element 264. The cable element 264 projects from the portion of the cable element 262 at which the audio signal wire 236 is located. This makes it possible to separately dispose the bioelectric potential wire 232 from the audio signal wire 236 and thus to reduce the occurrence of noise in a bioelectric potential caused by an audio signal.

Sixth Example of Cable

Figure 57:
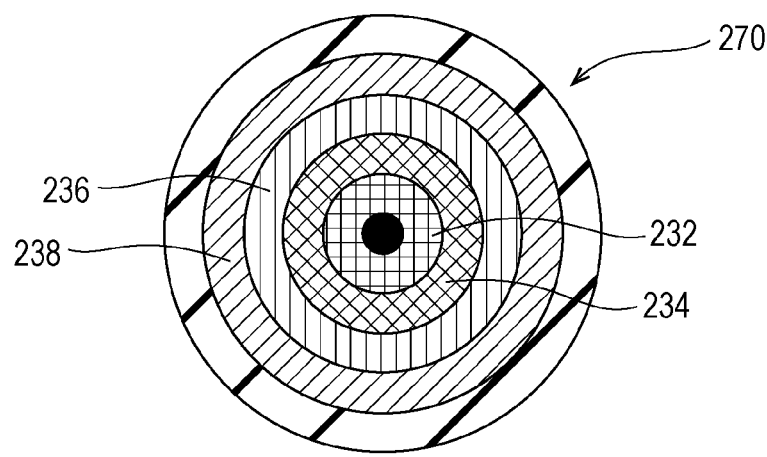
FIG. 57 is a sectional view illustrating a cable of a sixth example.

FIG. 57 is a sectional view illustrating the configuration of a cable 270 of a sixth example. The electrical wires 232, 234, 236, and 238 discussed in the second through fifth examples are disposed in the cable 270.

A cable 270 is a coaxial cable and is formed in a circular, elliptical, or rectangular shape in cross section. The ground electrode wire 234 is disposed around the bioelectric potential wire 232. The audio signal wire 236 is disposed around the ground electrode wire 234. The battery wire 238 is disposed around the audio signal wire 236. The ground electrode wire 234 is interposed between the bioelectric potential wire 232 and the audio signal wire 236 and also between the bioelectric potential wire 232 and the battery wire 238. In other words, the bioelectric potential wire 232 is not located adjacent to the audio signal wire 236 or the battery wire 238. It is thus possible to reduce the occurrence of noise in a bioelectric potential caused by an audio signal or power supply.

Seventh Example of Cable

Figure 58:
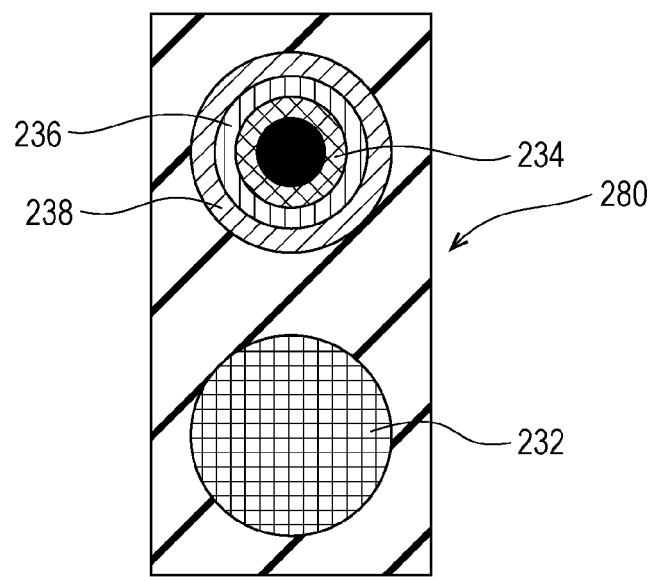
FIG. 58 is a sectional view illustrating a cable of a seventh example.

FIG. 58 is a sectional view illustrating the configuration of a cable 280 of a seventh example. The electrical wires 232, 234, 236, and 238 discussed in the second through sixth examples are disposed in the cable 280.

A coaxial cable is constituted by the ground electrode wire 234, the audio signal wire 236, and the battery wire 238. The bioelectric potential wire 232 is not included in the coaxial cable but is separately disposed at another position in the cable 280. As a result of separately disposing the bioelectric potential wire 232 from the other electrical wires, the occurrence of noise in a bioelectric potential caused by an audio signal or power supply is reduced.

Eighth Example of Cable

Figure 59:
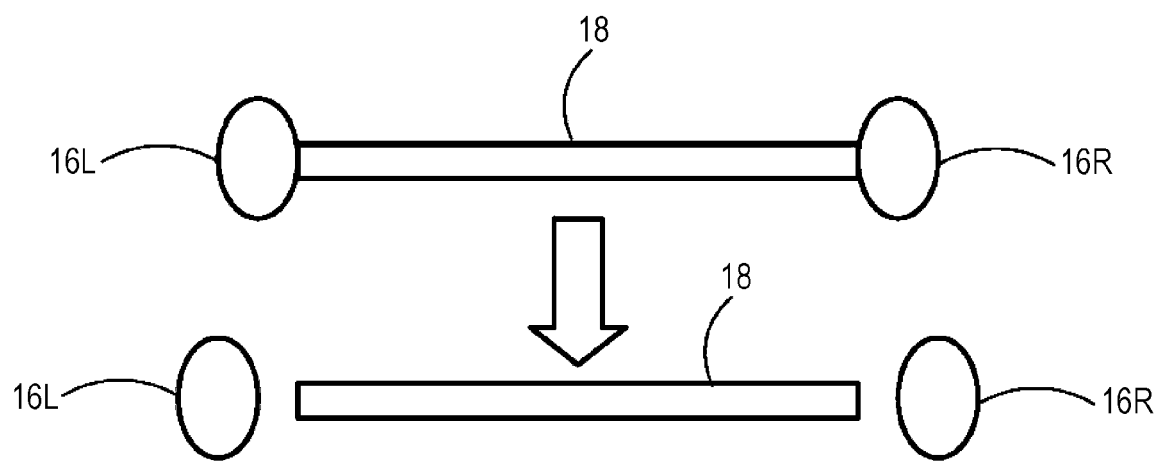
FIG. 59 is a schematic view illustrating a cable of an eighth example, a right-side earphone, and a left-side earphone.

FIG. 59 is a schematic view illustrating a cable of an eighth example. The right-side earphone 16R, the left-side earphone 16L, and the cable 18 are schematically shown in FIG. 59.

The right-side earphone 16R and the left-side earphone 16L may be attachable to and detachable from the cable 18. As connector terminals, known standards, such as USB or micro-miniature coaxial (MMCX) connector terminals, may be used. For example, the right-side earphone 16R and the left-side earphone 16L may be separated from the cable 18 and be connected to another cable.

When the right-side earphone 16R and the left-side earphone 16L are connected to the cable 18, they may communicate with another device, such as the terminal apparatus 14, by wired communication. When the right-side earphone 16R and the left-side earphone 16L are disconnected from the cable 18, they may communicate with another device by wireless communication. That is, the communication mode may automatically be switched from the wired communication mode to the wireless communication mode. The right-side earphone 16R and the left-side earphone 16L may be driven independently.

The functions of the right-side earphone 16R and the left-side earphone 16L and the communication mode may be changed in accordance with the type of cable 18 connected thereto.

Two devices of the same type may be connected to the cable 18, or two devices of different types may be connected to the cable 18. For example, the device connected to one end of the cable 18 may serve as a main device, while that to the other end of the cable 18 may serve as a sub-device. In this case, the main device may control the sub-device.

If two devices of different types are connected to the cable 18, the functions of these devices may be restricted. For example, access to memory units provided in the devices may be restricted, or it may not be allowed to control the devices.

The electrodes provided in the device connected to one end of the cable 18 may be used as a reference electrode and a ground electrode, while the electrode provided in the device connected to the other end of the cable 18 may be used as a sensor electrode. For example, when the right-side earphone 16R is connected to one end of the cable 18, the electrode of the right-side earpiece 22R is used as a reference electrode and the electrode member 28R is used as a ground electrode. When the left-side earphone 16L is connected to the other end of the cable 18, the electrode of the left-side earpiece 22L is used as a sensor electrode. For example, a brain wave sensor handles a potential signal indicating potentials detected by the electrode of the left-side earpiece 22L as a potential signal from the sensor electrode, a potential signal indicating potentials detected by the electrode of the right-side earpiece 22R as a potential signal from the reference electrode, and a potential signal indicating potentials detected by the electrode member 28R as a potential signal from the ground electrode.

Processing to be executed for a potential signal indicating potentials detected by each electrode will be described below, assuming that brain waves are monitored as biological information. As an example, processing for generating a brain wave signal based on sensor potentials detected by a sensor electrode, reference potentials detected by a reference electrode, and ground potentials detected by a ground electrode will be described below.

A balanced differential amplifier is used for generating a brain wave signal. For example, the above-described brain wave sensor 3410 (see FIG. 16) implements the function of a balanced differential amplifier. As the brain wave sensor 3410, a known balanced differential amplifier may be used.

Figure 60:
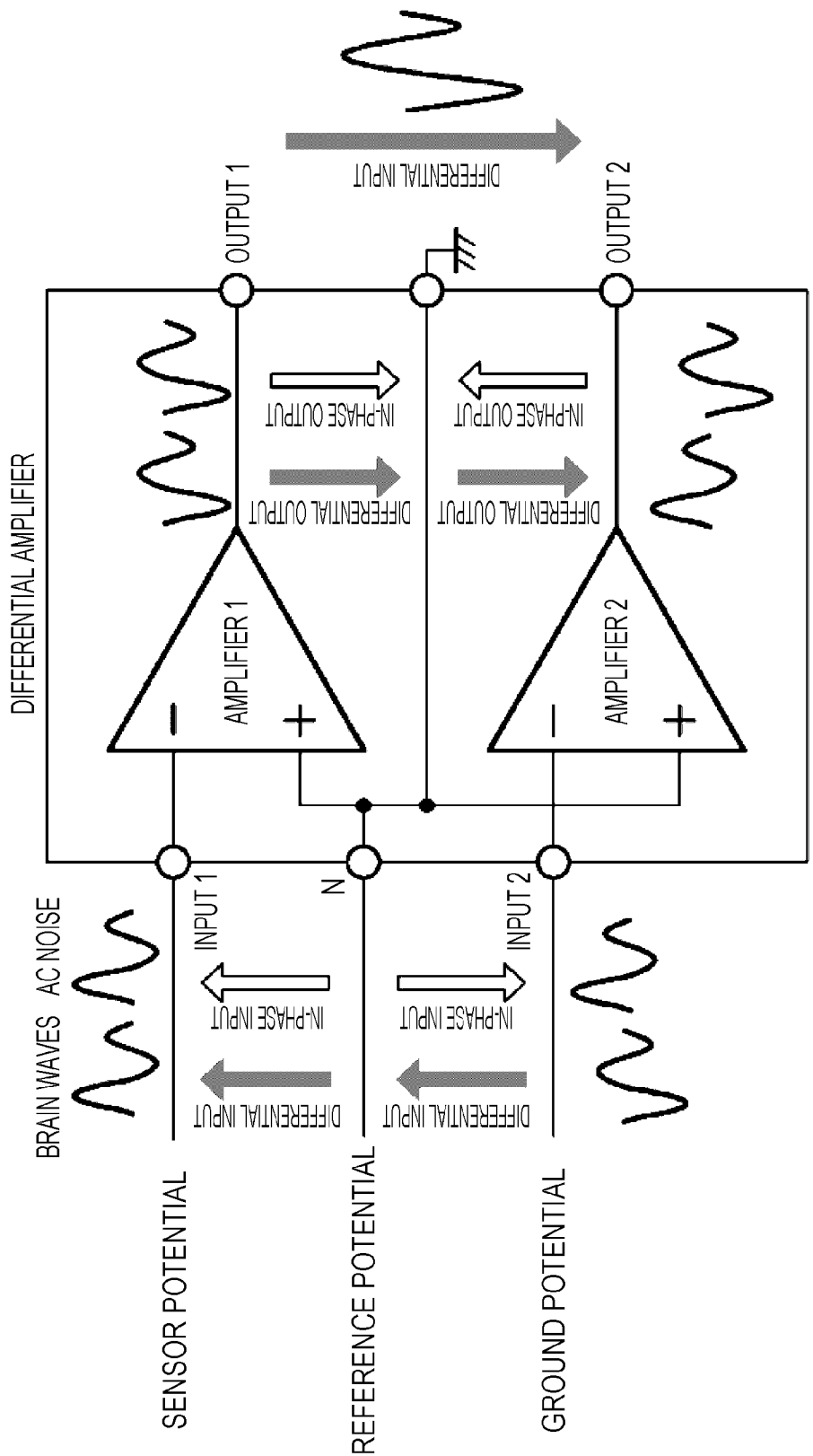
FIG. 60 illustrates a balanced differential amplifier.

FIG. 60 illustrates the configuration of the balanced differential amplifier. A potential signal indicating sensor potentials is input into the negative terminal of amplifier 1 (input 1), while a potential signal indicating reference potentials is input into a negative terminal of amplifier 2 (input 2). A potential signal indicating ground potentials is input into the positive terminal of each of amplifier 1 and amplifier 2. The potential signal is amplified in each of amplifier 1 and amplifier 2, and the difference between a signal output from amplifier 1 (output 1) and a signal output from amplifier 2 (output 2) is obtained. This difference output represents a brain wave signal.

Components (brain waves, for example) different between the potential signal indicating the sensor potentials and the potential signal indicating the reference potentials are amplified, while components common to the two potential signals (AC noise, for example) are canceled out.

[Selection of Electrodes]

Selection of a sensor electrode, a reference electrode, and a ground electrode will be described below through illustration of examples.

For example, a sensor electrode and a reference electrode are placed in the ears to contact the ear canals, while a ground electrode is placed in the ear to contact the cavity of concha. It is assumed, for example, that potential signals indicating potentials detected by the electrodes are output to a brain wave sensor.

First Example of Selection of Electrodes

Figure 61:
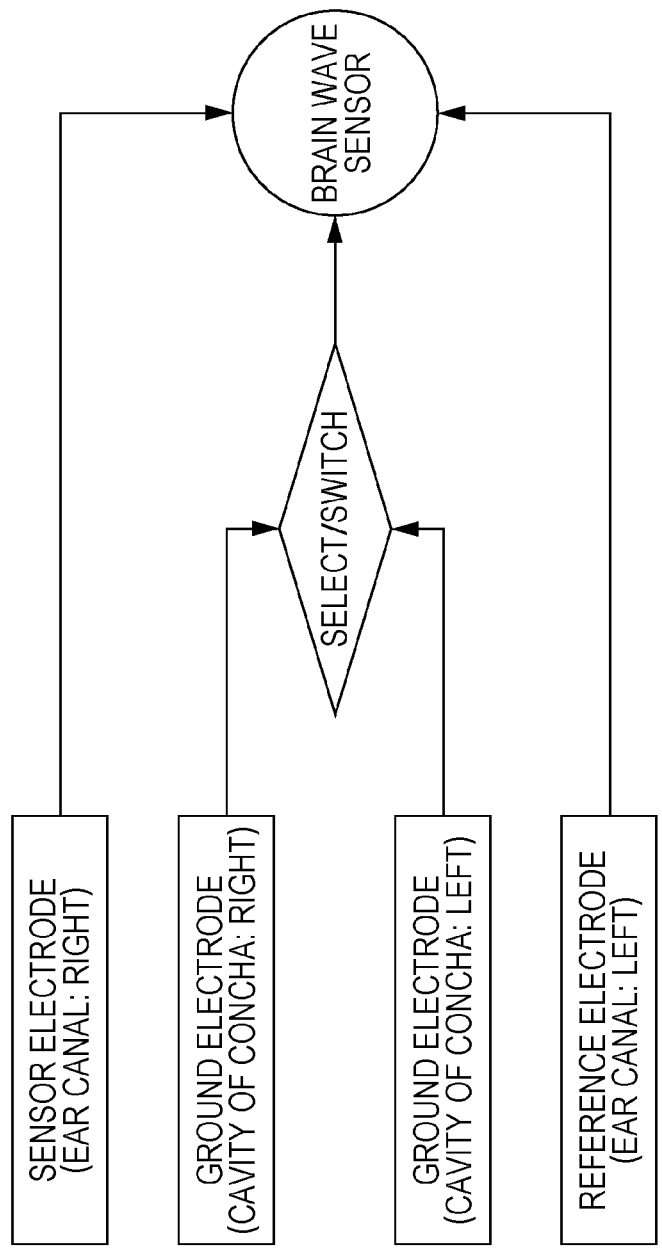
FIG. 61 illustrates an approach to selecting electrodes according to a first example.

A first example of the selection of electrodes will be discussed below with reference to FIG. 61. FIG. 61 is a diagram for explaining how to select electrodes.

The electrode placed in the ear canal of the right ear (electrode of the right-side earpiece 22R, for example) is used as a sensor electrode. The electrode placed in the ear canal of the left ear (electrode of the left-side earpiece 22L, for example) is used as a reference electrode. The electrode placed in the cavity of concha of the right ear (electrode member 28R, for example) is used as a ground electrode.

The electrode placed in the cavity of concha of the left ear (electrode member 28L, for example) is used as a ground electrode.

A potential signal indicating potentials detected by the sensor electrode and that by the reference electrode are output to the brain wave sensor.

One of a potential signal indicating potentials detected by the ground electrode placed in the cavity of concha of the right ear and that by the ground electrode placed in the cavity of concha of the left ear is output to the brain wave sensor, and the other potential signal is not output. The controller 16R7 (see FIG. 24), for example, selects which one of the potential signals is output to the brain wave sensor. For example, out of the two ground electrodes, the ground electrode that detects more stable potentials is selected, and a potential signal indicating potentials detected by the selected ground electrode is output to the brain wave sensor. A potential signal indicating more stable potentials is a signal having a smaller amplitude and a smaller change in the amplitude. For example, the right-side ground electrode and the left-side ground electrode are electrically connected with each other, and then, the ground electrode which detects potentials with a lower level of noise (potentials having a smaller amplitude) is selected. A potential signal indicating potentials detected by the selected ground electrode is output to the brain wave sensor.

Selection of electrodes may be performed before starting to monitor biological information. If a potential signal indicating potentials detected by a selected electrode is found to be unstable, the electrode to be used may be changed. This is also applied to the following examples.

Second Example of Selection of Electrodes

Figure 62:
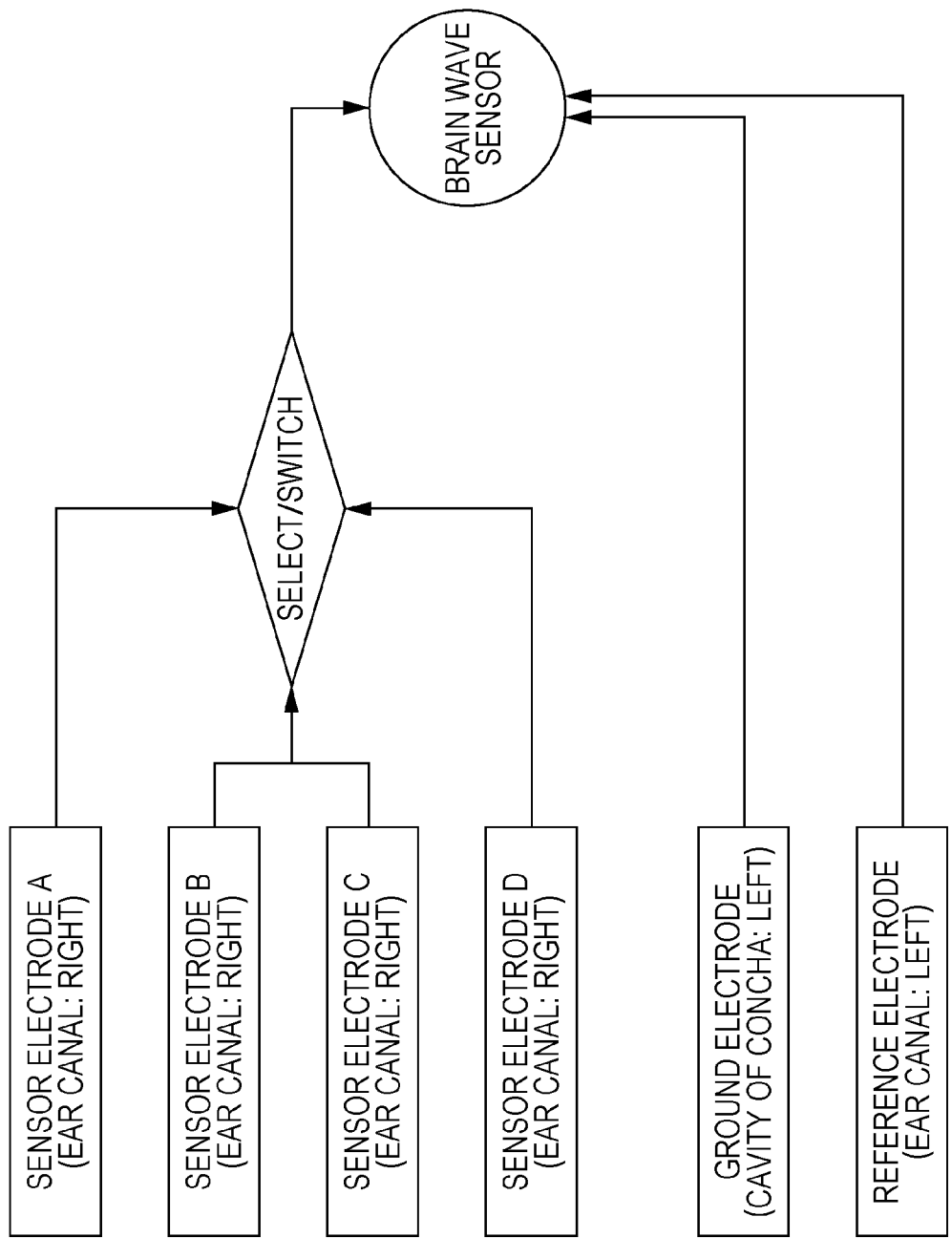
FIG. 62 illustrates an approach to selecting electrodes according to a second example.

A second example of the selection of electrodes will be discussed below with reference to FIG. 62. FIG. 62 is a diagram for explaining how to select electrodes.

Four electrodes (electrodes A, B, C, and D, for example) are placed in the ear canal of the right ear and are used as sensor electrodes. The electrode placed in the ear canal of the left ear is used as a reference electrode. The electrode placed in the cavity of concha of the left ear is used as a ground electrode.

A potential signal indicating potentials detected by the reference electrode and a potential signal indicating potentials detected by the ground electrode are output to the brain wave sensor.

A potential signal indicating potentials detected by one of the electrodes A, B, C, and D is output to the brain wave sensor. Among the electrodes A, B, C, and D, the electrode which detects more stable potentials is selected, and a potential signal indicating potentials detected by the selected electrode is output to the brain wave sensor. For example, a potential signal having a smaller amplitude of noise is selected as a signal indicating more stable potentials. The controller 16R7, for example, selects which one of the potential signals is output to the brain wave sensor.

Third Example of Selection of Electrodes

Figure 63:
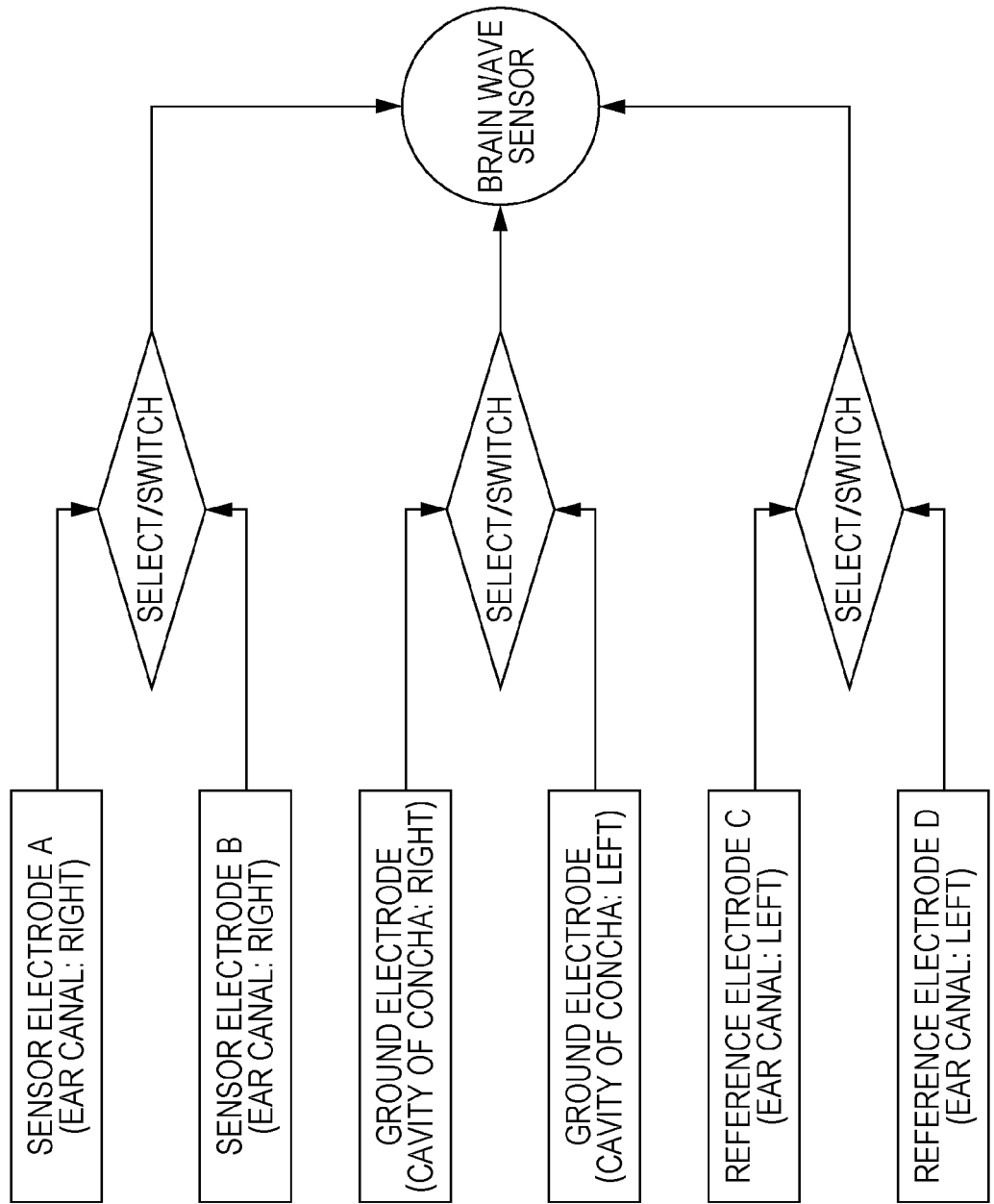
FIG. 63 illustrates an approach to selecting electrodes according to a third example.

A third example of the selection of electrodes will be discussed below with reference to FIG. 63. FIG. 63 is a diagram for explaining how to select electrodes.

Two electrodes (electrodes A and B, for example) are placed in the ear canal of the right ear and are used as sensor electrodes. Two electrodes (electrodes C and D, for example) are placed in the ear canal of the left ear and are used as reference electrodes. The electrode placed in the cavity of concha of each of the left and right ears is used as a ground electrode.

Out of the electrodes A and B, the electrode which detects more stable potentials is selected, and a potential signal indicating potentials detected by the selected electrode is output to the brain wave sensor. For example, a potential signal having a smaller amplitude of noise is selected as a signal indicating more stable potentials.

Out of the electrodes C and D, the electrode which detects more stable potentials is selected, and a potential signal indicating potentials detected by the selected electrode is output to the brain wave sensor. For example, a potential signal having a smaller amplitude of noise is selected as a signal indicating more stable potentials.

Out of the left-side ground electrode and the right-side ground electrode, the electrode which detects more stable potentials is selected, and a potential signal indicating potentials detected by the selected ground electrode is output to the brain wave sensor. For example, a potential signal having a smaller amplitude and a smaller change in the amplitude is selected as a signal indicating more stable potentials.

[Multiple Channels]

Plural items of the same type of biological information may be monitored. One item of biological information corresponds to one channel and multiple channels are formed in accordance with plural items of biological information. Processing for multiple channels of biological information will be described below with reference to the block diagram of FIG. 64.

Figure 64:
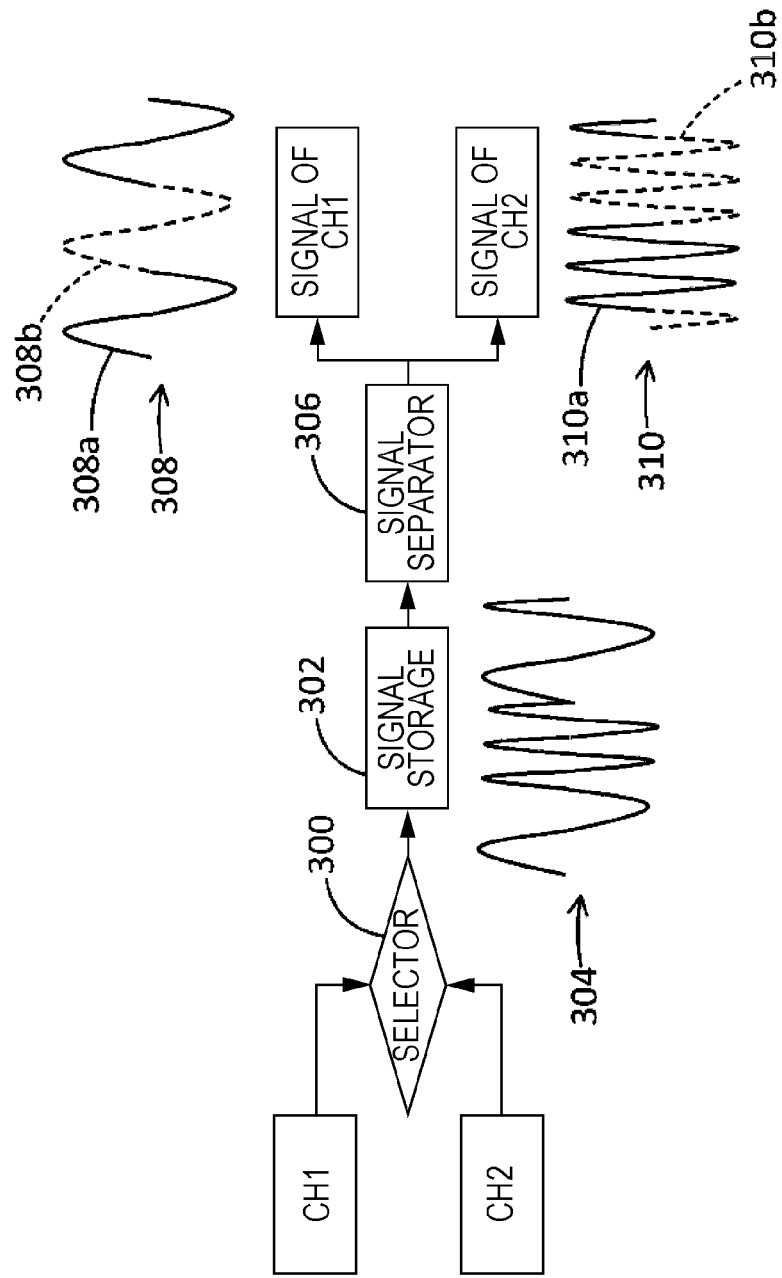
FIG. 64 is a block diagram illustrating the configuration of a device for processing multiple channels of biological information.

The functions shown in FIG. 64 are implemented by the brain wave sensor 3410 (see FIG. 16) or the processing unit 16R5. Another device or another processor may be used to implement the functions. It is assumed that the functions are implemented by the brain wave sensor 3410.

For example, a sensor electrode, a reference electrode, and a ground electrode are placed in the right ear. Biological information indicating brain waves is monitored by these electrodes and is processed by the brain wave sensor 3410 as a signal of channel CH1.

Additionally, a sensor electrode, a reference electrode, and a ground electrode are placed in the left ear. Biological information indicating brain waves is monitored by these electrodes and is processed by the brain wave sensor 3410 as a signal of channel CH2.

The above-described items of biological information allocated to channels CH1 and CH2 are only examples. Biological information monitored by an electrode placed in another part may be allocated to channel CH1 or channel CH2.

A selector 300 receives biological information of channel CH1 and that of channel CH2. The selector 300 switches between channels CH1 and CH2 at predetermined intervals and outputs one of biological information of channel CH1 and that of channel CH2 to a signal storage 302.

The signal storage 302 stores biological information output from the selector 300. For example, biological information of channel CH1 is stored in the signal storage 302 in association with channel information indicating channel CH1. Biological information of channel CH2 is stored in the signal storage 302 in association with channel information indicating channel CH2. A signal 304, which is an example of biological information, is stored in the signal storage 302.

A signal separator 306 extracts biological information stored in the signal storage 302, separates it into biological information of channel CH1 and that of channel CH2, and separately outputs these items of biological information.

While channel CH1 is being selected by the selector 300 and biological information of channel CH1 is being output to the signal storage 302, biological information of channel CH2 is not output to the signal storage 302. Likewise, while channel CH2 is being selected by the selector 300 and biological information of channel CH2 is being output to the signal storage 302, biological information of channel CH1 is not output to the signal storage 302. In this manner, as a result of the selector 300 switching between the channels, while one channel is not being selected, biological information of this channel is not stored in the signal storage 302.

For each channel, the signal separator 306 estimates biological information of a channel which is not being selected (that is, biological information of the channel which is not stored in the signal storage 302), based on biological information of this channel obtained during another period for which the channel is selected, thereby interpolating biological information during the period for which the channel is not selected.

For example, the signal separator 306 interpolates biological information of channel CH1 which is not being selected, based on biological information of channel CH1 obtained during the preceding and following periods for which channel CH1 is selected. Likewise, the signal separator 306 interpolates biological information of channel CH2 which is not being selected, based on biological information of channel CH2 obtained during the preceding and following periods for which channel CH2 is selected.

A signal 308 shown in FIG. 64 is an example of biological information of channel CH1. The signal 308 includes signal components 308a and 308b. The signal component 308a indicated by the solid line represents biological information of channel CH1 which is selected by the selector 300. The signal component 308b indicated by the broken line represents biological information of channel CH1 which is not selected by the selector 300, and this biological information is interpolated based on the signal component 308a during the preceding and following periods for which channel CH1 is selected.

A signal 310 shown in FIG. 64 is an example of biological information of channel CH2. The signal 310 includes signal components 310a and 310b. The signal component 310a indicated by the solid line represents biological information of channel 2 which is selected by the selector 300. The signal component 310b indicated by the broken line represents biological information of channel CH2 which is not selected by the selector 300, and this biological information is interpolated based on the signal component 310a during the preceding and following periods for which channel CH2 is selected.

In addition to or instead of switching between the channels at predetermined intervals, the selector 300 may switch between the channels based on the factor other than the time. That is, the time may not necessarily be used for switching between the channels.

For example, the selector 300 may switch between the channels in accordance with the magnitude of noise of each channel. More specifically, the selector 300 may select a channel having a smaller amplitude of noise and output biological information of the selected channel to the signal storage 302.

In another example, when executing an operation or processing using a right brain signal, the selector 300 selects channel CH1 and outputs biological information of channel CH1 to the signal storage 302. For example, in response to an instruction to operate a device by using a right brain signal, the selector 300 selects channel CH1. Likewise, when executing an operation or processing using a left brain signal, the selector 300 selects channel CH2 and outputs biological information of channel CH2 to the signal storage 302.

In another example, the selector 300 may select a channel in accordance with an instruction from a user.

[Noise Cancelling]

Processing for eliminating noise from biological information, that is, noise cancelling processing, will be discussed below. Noise cancelling processing is executed by the processing unit 16R5, for example. Noise refers to potential signal information other than that of a target subject to be monitored.

For example, from biological information monitored by electrodes and sensors for monitoring biological information of a target subject, the processing unit 16R5 eliminates biological information monitored by the other electrodes and sensors, thereby generating noise-free biological information of the target subject. That is, the processing unit 16R5 handles biological information monitored by the other electrodes and sensors as noise and eliminates the noise from biological information monitored by the electrodes and sensors for monitoring biological information of the target subject, thereby generating noise-free biological information of the target subject.

This will be explained below, assuming that brain waves are the target subject to be monitored. From biological information including information indicating brain waves (differential output shown in FIG. 60, for example) monitored by the above-described sensor electrode, reference electrode, and ground electrode, the processing unit 16R5 eliminates biological signals (also called biosignals) obtained from the other electrodes and sensors, such as a pulse sensor and an acceleration sensor, thereby generating noise-free biological information of the target subject. For example, from biological information including information indicating brain waves, the processing unit 16R5 eliminates the periods and the impulses of biological signals obtained from the other electrodes and sensors, such as a pulse sensor and an acceleration sensor, as noise. Noise refers to a signal transmitted through an organism and a signal transmitted from the outside of an organism, for example.

For example, the processing unit 16R5 handles as noise biological information monitored by electrodes and sensors placed in parts other than the parts on which a sensor electrode, a reference electrode, and a ground electrode are disposed. For example, when brain waves are monitored by using electrodes disposed in the ear canal, a myoelectric signal generated by pulsation (the blood flow cycle of blood vessels, for example), the motion of jaws, and blinking is treated as noise. The processing unit 16R5 eliminates this myoelectric signal from a biological signal obtained by the sensor electrode, reference electrode, and ground electrode, thereby generating a noise-free brain wave signal indicating brain waves.

This will be explained more specifically. In the ear canal, electrode A is placed at a top position (that is, a position close to the head), electrode B is placed at a bottom position (that is, a position close to the jaws), electrode C is placed at a front position (that is, a position close to the face), and electrode D is placed at a back position (that is, a position close to the body). The potential detected by the electrode C at a front position is likely to reflect myoelectric potentials caused by the motion of the face, such as blinking. The potential detected by the electrode B at a bottom position is likely to reflect myoelectric potentials caused by the motion of jaws and swallowing. In this case, the processing unit 16R5 handles the potentials detected by the electrodes B and C as noise and eliminates such potentials from biological information obtained from potentials detected by the other electrodes (differential output in FIG. 60, for example). As a result, a brain wave signal representing brain waves, free from noise caused by the motion of the face, jaws, and swallowing, can be obtained.

Noise cancelling processing has been discussed through illustration of brain waves. When another biological information is monitored, noise is eliminated similarly to that from brain waves.

Modified Examples of User Interface

The biological information monitoring apparatus 12 may display various items of information (such as biological information and other information) at a place other than the biological information monitoring apparatus 12. For example, the biological information monitoring apparatus 12 may display various items of information on an organism or an object, such as a desk or a wall.

If the biological information monitoring apparatus 12 is a watch-type wearable device worn on the arm of a user, it may display various items of information on the arm or the back of the hand of the user.

If the biological information monitoring apparatus 12 is a pair-of-glasses-type wearable device, it may display various items of information on the glasses.

Example of Sharing of Biological Information Monitoring Apparatus 12

The biological information monitoring apparatus 12 may be shared among multiple users. For example, after user A has used the biological information monitoring apparatus 12, user B may use it.

It is assumed that a contact-type biological information monitoring apparatus 12, which monitors biological information by brining electrodes and sensors into contact with an organism, such as a human, is used. When the organism (user) using the biological information monitoring apparatus 12 is changed by another organism (user), for example, the biological information monitoring apparatus 12 may output information that the user has been changed or an instruction to clean the biological information monitoring apparatus 12. Outputting such information or an instruction is performed by displaying such information or an instruction on a display, emitting it from a speaker as sound, or both operations. For example, if the right-side earphone 16R and the left-side earphone 16L are used, the controller 16R7 performs control to emit such information or an instruction from these earphones as sound. The controller 16R7 may alternatively perform control to display such information or an instruction on a display provided in the biological information monitoring apparatus 12. Alternatively, the controller 14d of the terminal apparatus 14 may perform control to display such information or an instruction on the terminal apparatus 14 or to emit it from a speaker provided in the terminal apparatus 14 as sound.

If a microphone is provided in the biological information monitoring apparatus 12, the controller 16R7 may recognize a user using the biological information monitoring apparatus 12 based on the voice of this user input from the microphone, and judge whether the user has changed. Alternatively, the controller 16R7 may recognize the user based on an image generated by a camera provided in the terminal apparatus 14.

In another example, the accounts of users using the biological information monitoring apparatus 12 are managed by the biological information monitoring apparatus 12, the terminal apparatus 14, or a server. When the account of the user using the biological information monitoring apparatus 12 is switched to another account, the controller 16R7 judges that the user 12 has changed.

Outputting information that the user using the biological information monitoring apparatus 12 has changed allows a new user to recognize that the biological information monitoring apparatus 12 has been used by another user and needs cleaning. Outputting an instruction to clean the biological information monitoring apparatus 12 also gives this information to a new user.

A sensor for sensing that the biological information monitoring apparatus 12 is cleaned may be used. For example, a sensor for sensing that electrodes and sensors are cleaned with alcohol (a sensor for sensing alcohol, for example) is used. When a user is trying to use the biological information monitoring apparatus 12 with electrodes and sensors uncleaned (when the uncleaned biological information monitoring apparatus 12 is powered ON, for example), the controller 16R7 outputs information that the biological information monitoring apparatus 12 has not been cleaned. The controller 16R7 may prevent the biological information monitoring apparatus 12 from being powered ON. When the user is trying to use the biological information monitoring apparatus 12 with the electrodes and sensors cleaned, the controller 16R7 may output information that the biological information monitoring apparatus 12 has been cleaned or may not output such information.

In the embodiments above, the term "processor" refers to hardware in a broad sense. Examples of the processor include general processors (e.g., CPU: Central Processing Unit) and dedicated processors (e.g., GPU: Graphics Processing Unit, ASIC: Application Specific Integrated Circuit, FPGA: Field Programmable Gate Array, and programmable logic device). In the embodiments above, the term "processor" is broad enough to encompass one processor or plural processors in collaboration which are located physically apart from each other but may work cooperatively. The order of operations of the processor is not limited to one described in the embodiments above, and may be changed.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. A biological information monitoring system comprising:
    a biological information monitoring apparatus that monitors biological information of an organism wearing the biological information monitoring apparatus on an ear; and a charger that charges the biological information monitoring apparatus in a non-contact manner,
one or more electronic circuits adapted for:
monitoring movement of the organism, and
controlling timing of charging of the biological information monitoring apparatus by the charger according to the movement of the organism.

2. The biological information monitoring system according to claim 1, wherein the biological information monitoring apparatus is a hearable device.

3. The biological information monitoring system according to claim 1, wherein the charger charges the biological information monitoring apparatus when the biological information monitoring apparatus is not monitoring the biological information.

4. The biological information monitoring system according to claim 1 further comprising a sensor that is configured to detect the movement of the organism.

5. The biological information monitoring system according to claim 4, wherein the sensor is a 6-axis sensor or a camera.

6. The biological information monitoring system according to claim 1, wherein the biological information monitoring apparatus determines when the organism is asleep or not based on the monitored biological information; wherein the charger charges the biological information monitoring apparatus when the biological information monitoring apparatus determines that the organism is asleep.

7. The biological information monitoring system according to claim 1, wherein the charger charges the biological information monitoring apparatus when the movement of the organism is smaller than or equal to a predetermined threshold.

8. The biological information monitoring system according to claim 1, wherein the charger charges the biological information monitoring apparatus when the movement of the organism is of a first type of movements and stops charging the biological information monitoring apparatus when the movement of the organism is of a second type of movement.

9. A method of charging a biological information monitoring system comprising:
using at least one sensor or electrode for monitoring biological information of an organism wearing the monitoring means on an ear;
monitoring movement of the organism, and
controlling timing of charging of the biological information monitoring apparatus by a charger according to the movement of the organism;
where in the charger
is a non-contact charger.

* * * * *